(12) United States Patent
Komlos et al.

(10) Patent No.: US 8,961,544 B2
(45) Date of Patent: Feb. 24, 2015

(54) DRY COMPOSITION WOUND DRESSINGS AND ADHESIVES COMPRISING GELATIN AND TRANSGLUTAMINASE IN A CROSS-LINKED MATRIX

(75) Inventors: Chagai Komlos, Haifa (IL); Guy Tomer, Modi'in (IL); Maria Ziv, Karmiel (IL); Orahn Preiss-Bloom, Zichron Yakov (IL); Thomas Bayer, Tel Aviv-Jaffa (IL)

(73) Assignee: Lifebond Ltd., Caesarea (IL)

( * ) Notice: Subject to any disclaimer, the term of this patent is extended or adjusted under 35 U.S.C. 154(b) by 102 days.

(21) Appl. No.: 13/813,814

(22) PCT Filed: Aug. 5, 2011

(86) PCT No.: PCT/IB2011/053505
§ 371 (c)(1),
(2), (4) Date: Feb. 5, 2013

(87) PCT Pub. No.: WO2012/017415
PCT Pub. Date: Feb. 9, 2012

(65) Prior Publication Data
US 2013/0131701 A1    May 23, 2013

Related U.S. Application Data

(60) Provisional application No. 61/370,821, filed on Aug. 5, 2010.

(51) Int. Cl.
*A61B 17/08*    (2006.01)

(52) U.S. Cl.
USPC .......................................................... 606/151

(58) Field of Classification Search
USPC ............................. 606/151; 424/443; 435/177
See application file for complete search history.

(56) References Cited

U.S. PATENT DOCUMENTS

| | | | |
|---|---|---|---|
| 1,394,654 A | 10/1921 | Tressler |
| 1,844,679 A | 2/1932 | Price |
| 1,873,580 A | 8/1932 | Hailwood |
| 1,950,483 A | 5/1934 | Christopher et al. |
| 2,048,499 A | 7/1936 | Gellednien |
| 2,126,305 A | 8/1938 | Babcock |
| 2,166,074 A | 7/1939 | Reichel |
| 2,398,004 A | 5/1946 | Houck et al. |
| 2,417,713 A | 3/1947 | Stein |
| 2,558,065 A | 6/1951 | Tice |
| 2,658,001 A | 11/1953 | Young |
| 2,719,145 A | 9/1955 | Skelton et al. |
| 2,803,548 A | 8/1957 | Hagetry |
| 3,220,845 A | 11/1965 | Lee |
| 3,600,482 A | 8/1971 | Salyer et al. |
| 3,939,001 A | 2/1976 | Clausi et al. |
| 3,988,479 A | 10/1976 | Stephan |
| 4,188,373 A | 2/1980 | Krezanoski |
| 4,188,465 A | 2/1980 | Schneider et al. |
| 4,224,348 A | 9/1980 | Hayashi |
| 4,344,181 A | 8/1982 | Baecklund |
| 4,426,443 A | 1/1984 | Shank |
| 4,478,822 A | 10/1984 | Haslam |
| 4,527,906 A | 7/1985 | Jezbera |
| 4,572,906 A | 2/1986 | Sparkes |
| 4,605,513 A | 8/1986 | DiMarchi |
| 4,651,725 A | 3/1987 | Kifune |
| 4,711,848 A | 12/1987 | Insley |
| 4,729,897 A | 3/1988 | Poppe |
| 4,837,379 A | 6/1989 | Weinberg |
| 4,891,319 A | 1/1990 | Roser |
| 4,931,501 A | 6/1990 | Lai et al. |
| 4,948,540 A | 8/1990 | Nigam |
| 4,952,618 A | 8/1990 | Olsen |
| 4,985,250 A | 1/1991 | Bee et al. |
| 5,015,677 A | 5/1991 | Benedict et al. |
| 5,059,636 A | 10/1991 | Grenga |
| 5,147,344 A | 9/1992 | Sachau |
| 5,209,776 A | 5/1993 | Bass |
| 5,399,361 A | 3/1995 | Song |
| 5,428,014 A | 6/1995 | Labroo |
| 5,433,943 A | 7/1995 | Osipow |
| 5,441,193 A | 8/1995 | Gravener |
| 5,480,644 A | 1/1996 | Freed |
| 5,487,889 A | 1/1996 | Eckert et al. |
| 5,487,895 A | 1/1996 | Dapper |
| 5,490,984 A | 2/1996 | Freed |
| 5,503,638 A | 4/1996 | Cooper et al. |
| 5,525,335 A | 6/1996 | Kitahara et al. |
| 5,549,628 A | 8/1996 | Cooper et al. |
| 5,549,904 A | 8/1996 | Juergensen |

(Continued)

FOREIGN PATENT DOCUMENTS

| | | |
|---|---|---|
| EP | 0073908 A1 | 3/1983 |
| EP | 0302953 | 2/1989 |

(Continued)

OTHER PUBLICATIONS

Fernandez-Diaz, M.D. et al., "Gel Properties of Collagens from Skins of Cod (*Gadus morhua*) and Hake (*Merluccius merluccius*) and Their Modification by the Coenhancers Magnesium sulphate, Glycerol and Transglutaminase", Food Chemistry, 2001, vol. 74, pp. 161-167.

Examination report for corresponding Australian Application No. 2007334394, mailed Jul. 20, 2012.

Wichman et al, "Kinetics of Refolding of Completely Reduced Human-Serum Albumin", European Journal of Biochemistry, vol. 79, 1977, pp. 339-344.

Office action issued for corresponding Chinese Application No. 200780051215.4, mailed Aug. 31, 2012.

(Continued)

*Primary Examiner* — Ralph Gitomer

(74) *Attorney, Agent, or Firm* — Graeser Associates International Inc; Dvorah Graeser

(57) ABSTRACT

Patches comprising dry gelatin compositions.

21 Claims, 12 Drawing Sheets

(56) References Cited

U.S. PATENT DOCUMENTS

| | | | |
|---|---|---|---|
| 5,575,803 | A | 11/1996 | Cooper et al. |
| 5,618,312 | A | 4/1997 | Yui |
| 5,702,409 | A | 12/1997 | Rayburn et al. |
| 5,736,132 | A | 4/1998 | Juergensen |
| 5,752,965 | A | 5/1998 | Francis et al. |
| 5,752,974 | A | 5/1998 | Rhee |
| 5,810,855 | A | 9/1998 | Rayburn |
| 5,834,232 | A | 11/1998 | Bishop |
| 5,895,412 | A | 4/1999 | Tucker |
| 5,931,165 | A | 8/1999 | Reich |
| 5,939,385 | A | 8/1999 | Labroo |
| 5,948,662 | A | 9/1999 | Kobayashi |
| 6,007,613 | A | 12/1999 | Izoret |
| 6,030,821 | A | 2/2000 | Soeda |
| 6,054,122 | A | 4/2000 | MacPhee et al. |
| 6,063,061 | A | 5/2000 | Wallace |
| 6,066,325 | A | 5/2000 | Wallace |
| 6,083,524 | A | 7/2000 | Sawhney |
| 6,100,053 | A | 8/2000 | Bech |
| 6,107,401 | A | 8/2000 | Dado et al. |
| 6,117,425 | A | 9/2000 | MacPhee et al. |
| 6,121,013 | A | 9/2000 | Yamaguchi |
| 6,132,759 | A | 10/2000 | Schacht |
| 6,136,341 | A | 10/2000 | Petito |
| 6,156,330 | A | 12/2000 | Tsukada |
| 6,162,241 | A | 12/2000 | Coury |
| 6,190,896 | B1 | 2/2001 | Fraij |
| 6,197,325 | B1 | 3/2001 | MacPhee et al. |
| 6,228,393 | B1 | 5/2001 | DiCosmo |
| 6,267,957 | B1 | 7/2001 | Green |
| 6,303,752 | B1 | 10/2001 | Olsen |
| 6,371,975 | B2 | 4/2002 | Cruise |
| 6,413,742 | B1 | 7/2002 | Olsen |
| 6,420,148 | B2 | 7/2002 | Yamaguchi |
| 6,454,787 | B1 | 9/2002 | Maddalo |
| 6,458,386 | B1 | 10/2002 | Schacht |
| 6,465,001 | B1 | 10/2002 | Hubbell |
| 6,475,516 | B2 | 11/2002 | DiCosmo |
| 6,509,039 | B1 | 1/2003 | Nies |
| 6,527,751 | B2 | 3/2003 | Fischer et al. |
| 6,531,147 | B2 | 3/2003 | Sawhney |
| 6,544,227 | B2 | 4/2003 | Sahatjian |
| 6,559,119 | B1 | 5/2003 | Burgess et al. |
| 6,576,685 | B2 | 6/2003 | Stedronsky |
| 6,605,066 | B1 | 8/2003 | Gravagna et al. |
| 6,610,043 | B1 | 8/2003 | Ingenito |
| 6,656,193 | B2 | 12/2003 | Grant et al. |
| 6,663,594 | B2 | 12/2003 | Sahatjian |
| 6,682,760 | B2 | 1/2004 | Noff |
| 6,704,210 | B1 | 3/2004 | Myers |
| 6,706,690 | B2 | 3/2004 | Reich |
| 6,762,336 | B1 | 7/2004 | Macphee |
| 6,773,156 | B2 | 8/2004 | Henning |
| 6,833,258 | B2 | 12/2004 | Yokoyama |
| 6,863,783 | B2 | 3/2005 | Lin |
| 6,875,796 | B2 | 4/2005 | Stedronsky |
| 6,939,358 | B2 | 9/2005 | Palacios et al. |
| 6,992,172 | B1 | 1/2006 | Chang |
| 7,019,191 | B2 | 3/2006 | Looney |
| 7,045,601 | B2 | 5/2006 | Metzner |
| 7,074,981 | B2 | 7/2006 | Chalmers |
| 7,108,876 | B2 | 9/2006 | Grindstaff |
| 7,109,163 | B2 | 9/2006 | Pendharkar |
| 7,129,210 | B2 | 10/2006 | Lowinger |
| 7,186,684 | B2 | 3/2007 | Pendharkar |
| 7,189,410 | B1 | 3/2007 | Drohan et al. |
| 7,196,054 | B1 | 3/2007 | Drohan et al. |
| 7,208,171 | B2 | 4/2007 | Messersmith et al. |
| 7,208,179 | B1 | 4/2007 | Drohan et al. |
| 7,229,959 | B1 | 6/2007 | Drohan et al. |
| 7,241,730 | B2 | 7/2007 | Hubbell |
| 7,285,580 | B2 | 10/2007 | Stedronsky |
| 7,320,962 | B2 | 1/2008 | Reich |
| 7,435,425 | B2 | 10/2008 | Qian |
| 7,459,425 | B2 | 12/2008 | Wan et al. |
| 7,468,350 | B2 | 12/2008 | Gong |
| 7,766,891 | B2 | 8/2010 | McGurk |
| 7,998,466 | B2 | 8/2011 | Hadba |
| 8,133,484 | B2* | 3/2012 | Preiss-Bloom et al. ... 424/94.63 |
| 8,367,388 | B2 | 2/2013 | Bloom et al. |
| 8,475,812 | B2* | 7/2013 | Nur et al. ........ 424/400 |
| 8,722,039 | B2* | 5/2014 | Preiss-Bloom et al. ..... 424/94.1 |
| 2001/0018598 | A1 | 8/2001 | Cruise |
| 2002/0015724 | A1 | 2/2002 | Yang |
| 2003/0008831 | A1 | 1/2003 | Yang |
| 2003/0035786 | A1 | 2/2003 | Hendriks |
| 2003/0120284 | A1 | 6/2003 | Palacios et al. |
| 2003/0135238 | A1 | 7/2003 | Milbocker |
| 2003/0219857 | A1 | 11/2003 | Chou |
| 2003/0232944 | A1 | 12/2003 | Molenberg |
| 2004/0093029 | A1 | 5/2004 | Zubik et al. |
| 2004/0106344 | A1 | 6/2004 | Looney |
| 2004/0131728 | A1 | 7/2004 | Ootsuka |
| 2005/0129733 | A1 | 6/2005 | Milbocker |
| 2005/0147646 | A1 | 7/2005 | Nilsson |
| 2005/0209441 | A1 | 9/2005 | Lile |
| 2005/0238683 | A1 | 10/2005 | Adhikari et al. |
| 2005/0249839 | A1 | 11/2005 | Ishida |
| 2005/0271727 | A1 | 12/2005 | Yao |
| 2006/0078962 | A1 | 4/2006 | Chen et al. |
| 2006/0100138 | A1 | 5/2006 | Olsen |
| 2006/0155234 | A1 | 7/2006 | Macphee |
| 2006/0258560 | A1 | 11/2006 | Yang et al. |
| 2006/0269590 | A1 | 11/2006 | Trotter |
| 2007/0021703 | A1 | 1/2007 | McCarthy |
| 2007/0082023 | A1 | 4/2007 | Hopman |
| 2007/0128152 | A1 | 6/2007 | Hadba |
| 2007/0172432 | A1 | 7/2007 | Stopek |
| 2007/0246505 | A1 | 10/2007 | Pace-Floridia et al. |
| 2008/0187591 | A1 | 8/2008 | Rhee |
| 2008/0195037 | A1 | 8/2008 | Hissong |
| 2008/0213243 | A1 | 9/2008 | Preiss-Bloom |
| 2008/0260801 | A1 | 10/2008 | Ahlers et al. |
| 2008/0286376 | A1 | 11/2008 | Qian |
| 2009/0175946 | A1 | 7/2009 | Gaissmaier |
| 2009/0191269 | A1 | 7/2009 | Gaissmaier et al. |
| 2010/0008989 | A1 | 1/2010 | Attar et al. |
| 2010/0063459 | A1* | 3/2010 | Preiss-Bloom et al. ...... 604/265 |
| 2012/0209319 | A1* | 8/2012 | Bianco-Peled et al. ....... 606/213 |
| 2012/0226211 | A1* | 9/2012 | Preiss-Bloom et al. ........ 602/43 |

FOREIGN PATENT DOCUMENTS

| | | |
|---|---|---|
| EP | 0707474 | 4/1996 |
| EP | 0726317 | 8/1996 |
| EP | 0745670 | 12/1996 |
| EP | 0777726 | 6/1997 |
| EP | 0815742 | 1/1998 |
| EP | 0871712 | 10/1998 |
| EP | 0876166 | 11/1998 |
| EP | 0927053 | 7/1999 |
| EP | 0947142 | 10/1999 |
| EP | 0982038 | 3/2000 |
| EP | 1124590 | 8/2001 |
| EP | 1263327 | 12/2002 |
| EP | 1267826 | 1/2003 |
| EP | 1267876 | 1/2003 |
| EP | 1288264 | 3/2003 |
| EP | 1372492 | 1/2004 |
| EP | 1494730 | 1/2005 |
| EP | 1574229 | 9/2005 |
| EP | 1857494 | 11/2007 |
| EP | 1948260 | 7/2008 |
| EP | 2133069 | 12/2009 |
| JP | 2204407 | 8/1990 |
| JP | 2255888 | 10/1990 |
| JP | 7328108 | 12/1995 |
| JP | 10510183 | 10/1998 |
| JP | 2002515300 A | 5/2002 |
| JP | 2004283371 A | 10/2004 |
| JP | 2006503612 A | 2/2006 |
| JP | 07227228 | 9/2007 |
| WO | WO9617929 | 6/1996 |
| WO | WO/96/40791 | 12/1996 |

(56) References Cited

FOREIGN PATENT DOCUMENTS

| | | |
|---|---|---|
| WO | WO/97/22372 | 6/1997 |
| WO | 9729715 A1 | 8/1997 |
| WO | WO9729715 | 8/1997 |
| WO | 9737694 A1 | 10/1997 |
| WO | 9740701 | 11/1997 |
| WO | 9741899 | 11/1997 |
| WO | WO/98/35026 | 8/1998 |
| WO | WO/00/22103 | 4/2000 |
| WO | WO/00/76533 | 12/2000 |
| WO | WO/01/15750 | 3/2001 |
| WO | 02098937 A1 | 12/2002 |
| WO | WO/03/011352 | 2/2003 |
| WO | WO/03/072155 | 9/2003 |
| WO | WO/03/072157 | 9/2003 |
| WO | WO/03/074004 | 9/2003 |
| WO | WO03/086493 | 10/2003 |
| WO | WO03080144 | 10/2003 |
| WO | WO2004004875 | 1/2004 |
| WO | WO/2004/014969 | 2/2004 |
| WO | 2004024195 A1 | 3/2004 |
| WO | WO2004/028404 | 4/2004 |
| WO | WO/2004/029096 | 4/2004 |
| WO | WO/2004/098671 | 11/2004 |
| WO | WO/2004/105485 | 12/2004 |
| WO | WO/2005/061701 | 7/2005 |
| WO | WO/2006/014567 | 2/2006 |
| WO | WO/2006/014568 | 2/2006 |
| WO | WO2006016809 | 2/2006 |
| WO | WO2006027622 | 3/2006 |
| WO | WO2006056700 | 6/2006 |
| WO | 2006086479 A2 | 8/2006 |
| WO | 2006128685 | 12/2006 |
| WO | WO/2006/134148 | 12/2006 |
| WO | WO/2007/008229 | 1/2007 |
| WO | 2007057175 A2 | 5/2007 |
| WO | WO2007057175 | 5/2007 |
| WO | WO/2007/122232 | 11/2007 |
| WO | WO/2007/123350 | 11/2007 |
| WO | WO/2007/126411 | 11/2007 |
| WO | WO/2007/134118 | 11/2007 |
| WO | WO/2008/006545 | 1/2008 |
| WO | WO2008006544 | 1/2008 |
| WO | WO/2008/016983 | 2/2008 |
| WO | 2008076407 | 6/2008 |
| WO | 2008076407 A2 | 6/2008 |
| WO | WO/2008/073938 | 6/2008 |
| WO | WO/2008/103891 | 8/2008 |
| WO | WO/2009/012882 | 1/2009 |
| WO | WO/2009/026158 | 2/2009 |
| WO | WO/2009/036014 | 3/2009 |
| WO | WO/2009/073193 | 6/2009 |
| WO | WO/2009/105614 | 8/2009 |
| WO | 2009153748 A2 | 12/2009 |
| WO | 2009153750 | 12/2009 |
| WO | 2009153751 A2 | 12/2009 |
| WO | WO/2010/027471 | 3/2010 |

OTHER PUBLICATIONS

Office action issued for corresponding Canadian Application No. 2672651, mailed Feb. 1, 2013.
Office action issued for corresponding Australian Application No. 2007334394, mailed Jan. 4, 2013.
Office action issued for corresponding Japanese Application No. 2009-541417, mailed Jan. 8, 2013.
Office action issued for corresponding European Application No. 7867783.8, mailed Jun. 27, 2012.
Office action issued for corresponding Chinese Application No. 200980131973.6, mailed Sep. 24, 2012.
Office action issued for corresponding European Application No. 9766287.8, mailed Mar. 12, 2013.
Office action issued for corresponding European Application No. 9766288.6, mailed Jun. 6, 2012.
Office action issued for corresponding European Application No. 12187110, mailed Nov. 21, 2012.
Office action issued for corresponding European Application No. 12155067, mailed Jul. 3, 2012.
Search report issued for corresponding PCT Application No. PCT/IB2010/056008, mailed Apr. 19, 2011.
Drury et al, "Hydrogels for tissue engineering: scaffold design variables and applications", Biomaterials, vol. 24, Nov. 2003, pp. 4337-4351.
Search report issued for corresponding PCT Application No. PCT/IB2011/051714, mailed Nov. 30, 2011.
Search report issued for corresponding PCT Application No. PCT/IB2011/053505, mailed Mar. 9, 2012.
Otani Y et al : "Effect of additives on gelation and tissue adhesion of gelatin-poly (L-glutamic acid) mixture" Dec. 1, 1998, Biomaterials, Elsevier Science Publishers BV., Barking, GB,pp. 2167-2173.
Nio N et al: "Gelation Mechanism of Protein Solution by Transglutaminase" and Biological Chemistry, Japan Soc. for Bioscience, Biotechnology and Agrochem, Tokyo, JP pp. 851-855, 1985.
Xie Z-P et al: "A novel casting forming for cermics by gelatine and enzyme catalysis" Mar. 1, 2000, Journal of the European CERAMIc Society, Elsevier Science Publishers, Barking, Essex, GB, pp. 253-257, XP004185604.
M. Gage Ochsner et al. Fibrin Glue as a Hemostatic Agent in Hepatic and Splenic Trauma. The Journal of Trauma. vol. 30, No. 7 1990. 884-887.
SAS_SAT 9_2 Users Guide.
Kozlov P V et al: "The structure and properties of solid gelatin and the principles of thier modification" Jun. 1, 1983, Polymer, Elsevier Science Publishers B.V, GB, pp. 651-666.
Holcomb, J. B., et al. (1997). Surgical Clinics of North America. 77:943-952).
HemCon™ bandage (HemCon, Portland.
QuikClot® ACS™ (Z-Medica, Wallington, CT).
OA for EP patent application 07867783.8 dated: Aug. 26, 2011.
Blood Weekly Editors. Gelatin-based adhesive has fibrin sealant benefit without use of blood products, Copyright 2004, Blood Weekly via NewsRx.com.
Hideraka Nagatomo, Gelatin-based adhesive has fibrin sealant benefit without use of blood products. Biosci, Biotechnol. Biochem, 2005, 128-136, 69 (1).
William D. Spotnitz, M.D. Commercial fibrin sealants in surgical care. The American Journal of Surgery (2001), 8S-14S, 182.
Nomura et al, "Improvement of Shark Type I Collagen with Microbial Transglutaminase in Urea", Biosci. Biotech. Biochem, vol. 65, 2001, pp. 982-985.
Chen et al, "Gelatin-Based Biomimetic Tissue Adhesive. Potential for Retinal Reattachment", Published online Nov. 8, 2005 in Wiley InterScience (www.interscience.wiley.com). DOI: 10.1002/jbm.b.30439.
Chen et al, "Enzyme-catalyzed gel formation of gelatin and chitosan: potential for in situ applications", Biomaterials vol. 24 (2003) pp. 2831-2841.
Examination Report for EP2133069 mailed Apr. 4, 2013.
Biomacromolecules, 2004, vol. 5, No. 4, p. 1270-1279.
de Carvalhoet al,; 1997; Physical gelation under shear for gelatin gels. Rheologica Acta 36(6): 591-609.
Examination Report for EP2303344 mailed Jun. 11, 2013.
Examination Report for EP2515957 mailed Jun. 24, 2013.
Extended Search report for EP2586467 mailed Jun. 17, 2013.
Journal of Biomedical Materials Research. Part B, Applied Biomaterials., 2006, 5, vol. 77, No. 2, p. 416-422.
Kwon, j. 2010; Rheological Behaviour of Gelatin at High Shear Rates. Ph.D Dissertation—University of Florida pp. 1-100. specif. pp. 27-28, 46.
Office Action for CA 2,728,187 mailed Apr. 2, 2013.
Office Action for CN 102124058 A mailed May 9, 2013.
Office Action for CN 101854960 A mailed Apr. 3, 2013.
Office Action for JP 2011-525128 mailed Aug. 6, 2013.
Office Action for JP2011-267107 mailed Jul. 23, 2013.
Orthodontics and Craniofacial Research, 2005, vol. 8, No. 3, p. 145-149.

(56) References Cited

OTHER PUBLICATIONS

Viscosity. Encyclopedia entry (online). Wikipedia, the free encyclopedia. "Dynamic Viscosity", p. 6 line 10; "Liquids", p. 9 line 7-8 [URL: http://en.wikipedia.org/wiki/viscosity].
Translation of office action from corresponding Chinese application No. 201110365186.7, received Mar. 27, 2014.
Office action from corresponding Chinese application No. 201110365186.7, received Mar. 27, 2014 (original Chinese language document).
Werten MWT, et al. Secreted production of a custom-designed, highly hydrophilic gelatine in Pichia pastoris. protein Engineering, vol. 14, No. 6, 447-454, Jun. 2001.
Olsen D et al. Recombinant collagen and gelatin for drug delivery. Adv Drug Deliv Rev. Nov. 28, 2003;55 (12) 1547-67.
Cui L, et al. Purification and characterization of transglutaminase from a newly isolated Streptomyces hygroscopicus. 2007: 105(2). p. 612-618.
Bertoni F, Barbani et al. Transglutaminase reactivity with gelatine: perspective applications in tissue engineering Biotechnol Lett (2006)28:697-702).
Broderick EP, et al. Enzymatic Stabilization of Gelatin-Based Scaffolds J Biomed Mater Res 72B: 37-42, 2005.
Folk JE, et al. Transglutaminase:mechanistic features of the active site as determined by kinetic and inhibitor studies. Biochim Biophys Acta. 1966; 122:244-64.
EP Search report for 11192607.7 dated May 10, 2012.
Chen et al. Biomacromolecules, vol. 4, 1558-1563, No. 6, 2003.
Haug et al. Food Hydrocolloids 18 (2004) 203-213.
D'Cruz NM, et al. Thermal Unfolding of Gelatin in Solids as Affected by the Glass Transition, J FOOD Science 2005: 70 (2), Kozlov PV, Burdygina GI.
Search Report for EP patent application 09162590.5 dated: Sep. 2, 2009.
Bello J, et al. Mechanism of Gelation of Gelatin. Influence of Certain Electrolytes on the Melting Points of Gels of Gelatin and Chemically Modified Gelatins. Am Chem Soc. Sep. 1956 (60). p. 1299-1306.
Crowe LM,et al. Is Trehalose Special for Preserving Dry Biomaterials? Biophysical Journal 1996 (71): 2087-2093.
Norie N, et al. Factors Affecting the Gelation of a Gelatin Solution in the Presence of Sugar. Journal of Home Economics of Japan. 55(2): p. 159-166 (2004).
J.M. Rocko et al. (1982). J. Trauma 22:635.
Harry B. Kram et al. Techniques of Splenic Preservation Using Fibrin Glue. The Journal of Trauma. vol. 30, No. 1 (97-101) 1990.
A.E. Pusateri et al. (2006). J. Trauma.. 60:674-682.
M.K. McDermott. et al: "Mechanical properties of biomimetic tissue adhesive based on the microbial transglutaminase-catalyzed crosslinking of gelatin" Biomacromolecules, ACS, Washington, DC, US, vol. 5, Jan. 1, 2004, pp. 1270-1279, XP002494450 ISSN: 1525-7797 [Retrieved on Apr. 21, 2004].
OA for EP patent application 09162590.5 dated: Jul. 6, 2010.
Ito A, J Biosci & Bioeng. 2003; 95(2):196-99.
OA for EP patent application 07867783.8 dated: Feb. 9, 2011.
D.B. Kendrick, Blood Program in WW II (Washington, DC: Office of the Surgeon General, Department of Army; 1989), 363-368.
Jackson, M., et al (1996). J. of Surg. Res. 60:15-22.
Jackson, M., et al. (1997) Surg. Forum. XL, VIII:770-772.
OA for EP11192607.7 dated Jan. 2, 2013.
E.M. Acheson. (2005). J. Trauma. 59(4): 865-74.
B.S. Kheirabadi. (2005). J. Trauma. 59(1): 25-34.
A.E. Pusateri. (2004). J Biomed. Mater. Res. B. Appl. Biomater. 15;70(1): 114-21.
J. L. Garza et al. (1990). J. Trauma. 30:512-513.
T.L. Matthew et al. (1990). Ann. Thorac. Surg. 50:40-44.
H Jakob et al (1984). J. Vasc. Surg. 1:171-180.
R. Lerner et ak. (1990). J. Durge. Res 48:165-181.
MSabel et al. (2004). Eur. Spine J. 13 (I): S97-101.
MG Tucci. (2001). J. Bioactive & Comp Polymers. 1692): 145-157.
B Balakrishnan et al. (2005). Biomaterials. 26932): 6335-42.
FA Weaver et al. (2002). Ann. Vasc. Surg. 16(3): 286-93.

OA for EP patent application 07867783.8 dated: Jan. 28, 2010.
Crescenzi V, et al (2002). Biomacromolecules. 3:1384-1391.
Gorman, J.J; J Bio. Chem. 1980, 255, 419-427.
Kahlem, P.; Acad. Sci U.S.A. 1996, 93, 14580-14585.
Etoh, Y.; Biochem, Biophys. Res Commun. 1986, 136, 51-56.
Hohenadi, C.; J. Biol. Chem. 1955, 270, 23415-23420.
Gross, M.; J. Biol. Chem. 1975, 250, 4648-4655.
Groenen, P.; Eur. J. Biochem. 1994, 220, 795-799.
Grootjans, J. J. Biol. Chem. 1995, 270, 22855-22858.
Owen et al. N. Engl. J. Med. 309:694-698, 1983.
PCT Search Report for corresponding PCT application PCT/US07/025726.
International Search Report for PCT/IB2009/052600.
International Search Report for PCT/IB2009/052605.
International Search Report for PCT/IB2009/052607.
EP Application 09766288.6 Office Action dated Jun. 6, 2012.
Abrams GW et al. The incidence of corneal abnormalities in the Silicone Study. Silicone Study Report 7. Arch Ophthalmol 1995;113:764-769.
Alio JL et al. A new acrylic tissue adhesive for conjunctival surgery: experimental study. Ophthalmic Res 2003, 35:306-312.
Bloom JN et al. A Light-activated surgical adhesive for sutureless ophthalmic surgery, Arch Ophthamol 2003; 121: 1591-1595.
Cooper et al. J. Thorac. Cardiovasc. Surg. 109106-116, 1995.
Cooper et al. J. Thorac. Cardiovasc. Surg. 1121319-1329, 1996.
Eidt et al. Am J Surg 1999:178:511-516.
Ghazi NG et al. Pathology and pathogenesis of retinal detachment. Eye 2002;16:411-421.
Grotenhuis Andre J. Healthcare Economics Costs of postoperative cerebrospinal fluid leakage: 1-year, retrospective analysis of 412 consecutive nontrauma cases, Surgical Neurology 64 (2005) 490-494.
Johanning JM et al. Femoral artery infections associated with percutaneous arterial closure devices, J Vasc Surg 2001;34:983-985.
Katloff et al. A Comparison of Median Sternotomy and Thoracoscopic Approaches, Chest 110:1399-1406,1996.
Ninan L et al. Adhesive strength of marine mussel extracts of procine skin. Biomaterials 2003;24:4091-4099.
Olivieri MP et al. Surface properties of mussel adhesive protein component films. Biomaterials 1992,13:1000-1008.
Shahidi M et al. Retinal topography and thickness mapping in atrophic age related macular degeneration. Br J Ophthalmol 2002;86:623-626.
Smith TP et al. Infectious complications resulting from use of hemostatic puncture closure devices, Am J Surg 2001;182:658-662.
Swanson et al. J Am. Coll Surg: 185:25-32, 1997.
Toursarkissian B et al. Changing Pattern of Access Site Complications with the Use of Percutaneous Closure Devices, Vasc Endovasc Surg 2001;35:203-206.
Velazquez AJ at el., New dendritic adhesives for sutureless ophthalmic surgical procedures: in viro studies of corneal laceration repair. Arch Ophthamol 2004;122:867-870.
Japanese Application 2011-514184 Office Action.
Agricultural and Biological Chemistry, 1989 (53,10), 2619-2623.
De Joung et al. J. Agric.Food.Chem, 2001(49), 3389-3393.
Gan et al. Food Hydrocolloids 2009 (23), 1398-1405.
Hirose at al. Gelation of Bovine Serum Albumin by Glutathione, J Food Sci, 1990 (55,4) 915-917.
Kang et al. Effect of Disulfide Bond Reduction on Bovine Serum Albumin-Stabilized Emulsion Gel Formed by Microbial Transglutaminase, J Food Sci, 2003 (68,7), 2215-2220.
Lee et al. Agricultural and Biological Chemistry, vol. 55, No. 8 (1991) 2057-2062.
Tobitani et al, Heat-Induced Gelation of Globular Proteins. 1. Model for the Effects of Time and Temperature on the Gelation Time of BSA Gels, Macromolecules, 1997 (30,17), 4845-4854.
Alur HH et al. Transmucosal sustained-delivery of chlorpheniramine maleate in rabbits using a novel, natural mucoadhesive gum as an excipient in buccal tablets, Int. J. Pharm., 1999, 88(1), 1-10.
Babin H et al. Food Hydrocolloids 2001, 15, 271-276.
Bernkop-Schnurch A et al. Pharm. Res., 1999, 16, 6, 876-81.32.

(56) References Cited

OTHER PUBLICATIONS

Buchta C et al. Biochemical characterization of autologous fibrin sealants produced by CryoSeal and Vivostat in comparison to the homologous fibrin sealant product Tissucol/Tisseel, Biomaterials 2005, 26, 6233-41.27-30.
Pusateri, 2004 J Biomed Mater Res B, 15; 70(1): 114-121.
Burzio LA et al. Cross-Linking in Adhesive Quinoproteins: Studies with Model Decapeptides, Biochemistry 2000, 39, 11147-53.
Deacon MP et al. Structure and Mucoadhesion of Mussel Glue Protein in Dilute Solution, Biochemistry 1998, 37, 14108-12.
Ehrbar M et al. Enzymatic formation of modular cell-instructive fibrin analogs for tissue engineering, Biomaterials 2007, 28, 3856-66.
Fisher MT et al, PNAS 103, 2006: p. 13265-6.
Garcia Y et al. Assessment of cell viability in a three-dimensional enzymatically cross-linked collagen scaffold. J Mater Sci Mater Med. Oct. 2007;18(10):1991-2001.
Ghebremeskel et al 2007, International Journal of Pharmaceutics 328: 119-129.
Yokoyama K et al. Protein Exp & Purif 26, 2002: p. 329-335 2002.
Rajagopalan et al. J Biologica Chem 236(4), 1960.
Glickman M et al. Arch Surg 2002, 137, 326-31.
Gutowska A et al. Anat Rec 2001, 263, 342-349.
Haines-Butterick L et al. Controlling hydrogelation kinetics by peptide design for three-dimensional encapsulation and injectable delivery of cells, Proc Natl Acad Sci U S A 2007, 104, 7791-6.
Hussain I et al, Animal Feed science and Technology, 1996;62 (2), p. 121-129.
Ikura K et al. Biosci Biotechnol Biochem. 66(6), 2002, p. 1412-1414.
Iwata H et al. A novel surgical glue composed of gelatin and N-hydroxysuccinimide activated poly(L-glutamic acid): Part 1. Synthesis of activated poly(L-glutamic acid) and its gelation with gelatin; Biomaterials 1998, 19, 1869-76.
Jackson M. Fibrin sealants in surgical practice: An overview, Am J Surg 2001, 182, 1S-7S.
Akira et al, Activity and Stability of Microbial Transglutaminase Modified with a Water-Soluble Polymer, JapaneseJournal of Polymer Science and Technology (Kobunshi Ronbunshu), vol. 58, No. 2, pp. 73-77 (Feb. 2001).
Notice of Opposition for corresponding EP application 07867783.8, mailed Dec. 3, 2013.
Office action issued for related EP 11768111.4 Mailed Feb. 27, 2014.
Office action from corresponding Chinese application No. CN 201080057151.0, mailed Nov. 27, 2013 (original Chinese language document).
Office action issued for related Chinese Application 201180044965.5 Mailed Feb. 7, 2014.
Translation of office action from corresponding Japanese application No. 2009-541417, mailed Dec. 3, 2013.
Translation of summary of office action from corresponding Chinese application No. CN 201080057151.0. mailed Nov. 2013.
W.O. Spotniz (1995). Thromb. Haemost 74:482-485.
Office action issued for corresponding Japanese Application No. 2011-267107, mailed Feb. 4, 2014—Translation.
Office action issued for related Chinese Application 201180044965.5 Mailed Feb. 7, 2014—Translation.
Office action issued for corresponding EP Application No. 11192607.7 on Jan. 2, 2013.
Search report issued for corresponding EP Application No. 11192607.7 on May 10, 2012.
Juggi JS et al., In-Vivo Studies with a cation Exchange Resin Mixture in the Removal of Excessive Ammonium from the Extracorporeal Circulation System. ANZ J Surg 1968;38 (2) p. 194-201.
O'Halloran DM et al. Characterization of a microbial transglutaminase cross-linked type II collagen scaffold. Tissue Eng. Jun. 2006; 12(6): 1467-74.
Ohtake Y et al. Transglutaminase catalyzed dissociation and association of protein-polyamine complex; Life Sciences 2007; 81,7: p. 577-584.
Otani Y et al. Sealing Effect of Rapidly Curable Gelatin-Poly (L-Glutamic Acid) Hydrogel Glue on Lung Air Leak; Ann Thorac Surg 1999, 67, 922-6.
Rodriguez et al. Combined effect of plasticizers and surfactants on the physical properties of starch based edible films; Food Research International 39 (2006) 840-6.
Sanbom TJ et al. In situ crosslinking of a biomimetic peptide-PEGhydrogel via thermally triggered activation of factor XIII; Biomaterials 2002, 23, 2703-10.
Serafini-Fracassini D et al. First Evidence for Polyamine Conjugation Mediated by an Enzymic Activity in Plants; Plant Physiol. (1988) 87, 757-761.
Shojaei AM et al. Mechanisms of buccal mucoadhesion of novel copolymers of acrylic acid and polyethylene glycol monomethylether monomethacrylate; Journal of Control Release, 1997, 47, 151-61.27.
Silva EA et al. Spatiotemporal control of vascular endothelial growth factor delivery from injectable hydrogels enhances angiogenesis; J Thromb Haemost 2007, 5, 590-8.
Silverman HG et al. Understanding Marine Mussel Adhesion; Mar Biotechnol (NY) 2007, 9, 661-81.
Sperinde J et al. Control and Prediction of Gelation Kinetics in Enzymatically Cross-Linked Poly(ethylene glycol) Hydrogels; Macromolecules 2000, 33, 5476-5480.
Strausberg RL et al, Protein-based medical adhesives, Trends Biotechnol 1990;8:53-5.
Sung HW et al. Evaluation of gelatin hydrogel crosslinked with various crosslinking agents as bioadhesives: In vitro study; J Biomed Mater Res 1998, 46, 520-30.
Ulijn RV et al. Designing peptide based nanomaterials; Chem Soc Rev 2008, 37, 664-75.
Langoth N et al. Development of buccal drug delivery systems based on a thiolated polymer, Int. J. Pharm., 2003, 252, 141-48.
Lehr C et al. Pharma Res., 1992, 9(4), 547-53.
Lim DW et al. In Situ Cross-Linking of Elastin-like Polypeptide Block Copolymers for Tissue Repair; Biomacromolecules 2008, 9, 222-30.
Ma et al. Enhanced biological stability of collagen porous scaffolds by using amino acids as novel cross-linking bridges; Biomaterials. 2004, 25(15): p. 2997-3004.
Mahoney MJ et al. Contrasting effects of collagen and bFGF-2 on neural cell function in degradable synthetic PEG hydrogels; J Biomed Mater Res A 2007, 81, 269-78.
McDowell et al. Rotational Echo Double Resonance Detection of Cross-links Formed in Mussel Byssus under High-Flow Stress; Biol Chem 1999, 274,20293-5.
Motoki M et al. Transglutaminase and its use for food processing; Trends in Food Science & Technology 1998, 9, 204-210.
Nakamura E et al. Role of glutamine and arginase in protection against ammonia-induced cell death in gastric epithelial cells, Am J of Phys. GI and Liver Phys, 2002; 46(6), p. G1264-G1275.
Jakob H. et al. (1984). J. Vasc. Surg. 1:171-180.
Japanese office action for corresponding Japanese application No. 2009-541417, mailed on Apr. 2, 2013.
De Carvalho & Grosso, "Characterization of gelatin based films modified with transglutaminase, glyoxal and formaldehyde", Food Hydrocolloids 18 (2004) 717-726.
Dong et al., "Optimization of cross-linking parameters during production of transglutaminase-hardened spherical multinuclearmicrocapsules by complex coacervation" Colloids and Surfaces B: Biointerfaces 63 (2008) 41-47.

\* cited by examiner

Figure 3
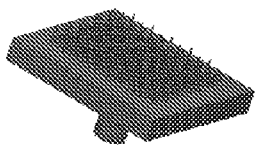
The perforator used in example #4
Figure 4 - Flowchart for example #4
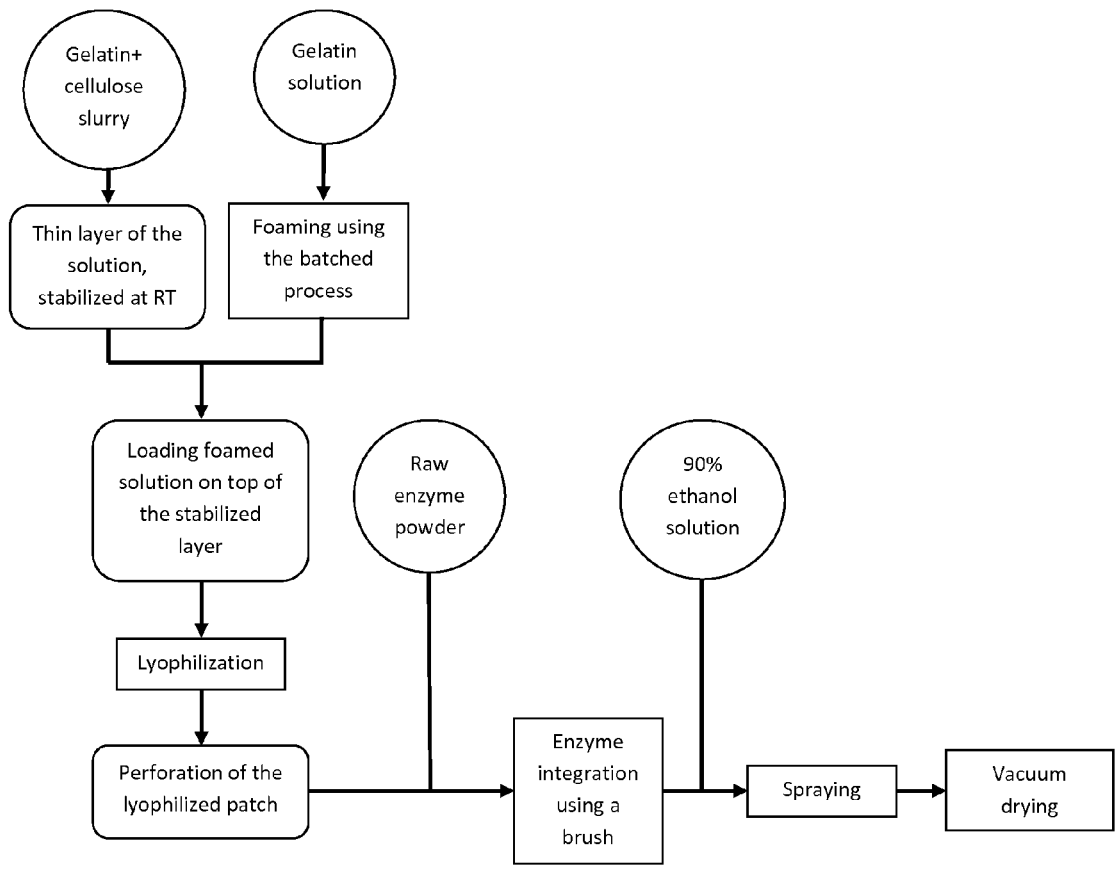

DRY COMPOSITION WOUND DRESSINGS AND ADHESIVES COMPRISING GELATIN AND TRANSGLUTAMINASE IN A CROSS-LINKED MATRIX

FIELD OF THE INVENTION

The present invention relates to wound dressings, devices, sealants, and adhesive agents that contain resorbable or non-resorbable materials and/or proteins, and in particular, but not exclusively, to such devices and agents that are useful for the treatment of wounded tissue, coating of implantable devices, or adhesion of implantable devices to tissue.

BACKGROUND OF THE INVENTION

Surgical wound closure is currently achieved by sutures and staples that facilitate healing by pulling tissues together. However, very often they fail to produce the complete seal necessary to prevent bleeding and fluid leakage. Thus, there is a large, unmet medical need for devices and methods to prevent bleeding and leakage during and following surgery, including leaks that frequently occur along staple and suture lines. Such devices and methods are needed as an adjunct to sutures or staples to achieve hemostasis or other fluid-stasis in peripheral vascular reconstructions, dura reconstructions, thoracic, cardiovascular, lung, neurological, and gastrointestinal surgeries.

In addition to surgery, the control of hemorrhage (bleeding) is a critical step in first aid and field trauma care.

A wide range of products have been suggested as solutions for hemostasis and fluid stasis both as first aid and as surgical devices. However, existing products comprise limited or partial solutions that frequently have significant drawbacks.

As an example of non-optimal hemostasis products: currently no commercially available device involving cross-linked gelatin networks has been able to independently induce hemostasis for brisk internal bleeding, even with the addition of thrombin. A study was done comparing the hemostatic capacity of FloSeal gelatin matrix (BioSurgery, Fremont, Calif.) and GelFoam gelatin matrix soaked in active thrombin solution. Neither enhanced hemostatic device was able to stop flow characterized bleed in more than ⅔ of patients after 5 minutes. Pulsatile arterial bleeding is far more brisk than flow bleeding and would most certainly present a problem for these thrombin-soaked matrices (F A Weaver et al. (2002). *Ann Vasc Surg* 16(3):286-93).

In any case, there remains a distinct deficiency in trauma and surgical care, in that there is no novel, active hemostatic field dressing or surgical dressing that is commercially available which can control hemorrhage and fluid leakage without significant side effects. Similarly, there remains a distinct deficiency in surgical care, in that there is no commercially available non-toxic sealant that is capable of withstanding brisk bleeding and able to seal wound sites leaking non-blood body fluids.

SUMMARY OF THE INVENTION

There is a need for, and it would be useful to have, a non-toxic adhesive material which could be used for a wide variety of applications, including but not limited to surgical applications, control of hemorrhage and control of bleeding from a wound. There is also a need for, and it would be useful to have, a non-toxic adhesive material which could be used as part of a hemostatic bandage. There is also a need for, and it would be useful to have, a non-toxic adhesive material which could be used as a surgical sealant and which is available as a dry composition.

The present invention overcomes the drawbacks of the background art by providing, in at least some embodiments, an adhesive material which comprises a cross-linkable protein and a non-toxic material which induces cross-linking of the cross-linkable protein. Preferably, the cross-linkable protein includes gelatin and any gelatin variant or variant protein as described herein. Optionally and preferably, the non-toxic material comprises transglutaminase (TG), which may optionally comprise a microbial transglutaminase (mTG). According to some embodiments of the present invention, the adhesive material is provided in a bandage, which is preferably adapted for use as a hemostatic bandage. According to other embodiments, it is provided as a sealant, which is preferably adapted for use as a surgical sealant.

When acted upon by a transglutaminase, gelatin, which is a denatured form of the protein collagen, undergoes rapid crosslinking to form a vibrant gel. PCT Application No. PCT/US07/25726, filed on Dec. 17, 2007, owned in common with the present application and having at least some inventors in common with the present application, describes some embodiments of an adhesive material based on this mechanism.

Also, as discussed in depth in PCT Application No. PCT/US07/25726, a variety of fibrin-thrombin products have been suggested for applications similar to the surgical and medical indications suggested herein (i.e. controlling hemorrhage and sealing leaks). However, the described embodiments of the present invention avoid the significant drawbacks inherent products, like fibrin and thrombin, which are either directly blood-derived or modeled on blood derived proteins. Such drawbacks include high cost, insufficient stability, viral risk, and insufficient availability.

Unlike a clotted fibrin network, the gelatin-TG network has an additional benefit in that it can be dissolved specifically using a specified protease that is not otherwise physiologically reactive (T. Chen, Biomacromolecules. 2003 November-December; 4(6):1558-63). Thus, while a gelatin-mTG hemostatic dressing or sealant improves upon the performance of a fibrin-thrombin hemostatic dressing or sealant, it also can be removed as desired without complication.

The present invention, in at least some embodiments comprising a gelatin-TG based hemostatic device, has great potential as a hemostatic field dressing for trauma care, in addition to utility in controlling brisk, arterial bleeding during surgery, bleeding after endo-vascular catherization, or leakage of other bodily fluids after injuries or during surgery.

The term "device", as referred to herein, may include any material or plurality of materials suitable for use in medical care, for example, in treating trauma to the body, bleeding and/or leakage of bodily fluids from an injury and/or during surgery. The device may include, for example, one or more of a bandage, a patch, a dressing, a plaster, an adhesive or elastic wound covering and the like. As described herein, the term "patch" may optionally relate to any type of reinforcement and/or fixation device, as well as optionally to a device for wound closure and/or management, without limitation in geometry, shape and of any suitable dimensions.

These compositions, methods of treatment and devices overcome the drawbacks of the background art, some aspects of which are described below without wishing to be limited to a closed list. Prior attempted solutions used many forms of modified and unmodified gelatin networks for mild to moderate hemostasis. However, a method of forming, in situ, a strongly cross-linked gelatin network that can control brisk bleeding arterial hemorrhage or other significant bodily fluid leakages has been lacking.

In some demonstrative embodiments, there is provided a method and/or a device, which may include gelatin-TG cross-linking, e.g., in order to form a strong gelatin network in vivo, for example, by increasing the mechanical strength of a gelatin matrix and/or by making it suitable for controlling high-pressure arterial bleeding and/or other bodily fluid leakages.

According to some demonstrative embodiments, the methods and/or devices described herein may include In-situ cross-linking between gelatin chains and endogenous collagen of tissue ECM (extra cellular matrix), for example, to create a strong, hemostatic barrier for fluids.

In some demonstrative embodiments, the methods and/or devices described herein may include effectively affecting hemostasis and/or fluid-stasis, for example, by having Gelatin and TG applied in a lyophilized form, e.g., wherein the Gelatin and TG may be reconstituted by the blood or other body fluid. As used herein, the term "lyophilization" may optionally relate to any type of drying, including but not limited to vacuum drying. Optionally and preferably, drying is performed at a temperature that is lower than the sol-gel transition temperature (the physical gelation point) of the composition's protein matrix.

In some demonstrative embodiments, the methods and/or devices described herein may include a gelatin-TG mixture in lyophilized form, characterized, for example, by having an increased shelf life.

In some demonstrative embodiments, the methods and/or devices described herein may include Gelatin and TG in layered, lyophilized form, for example, to provide more rapid reconstitution, which, in accordance with some embodiments, may be helpful for a high pressure fluid flow environment.

In some demonstrative embodiments, the methods and/or devices described herein may include a dry composition based on gelatin cross-linking technology that may mimic the natural blood-clotting cascade and/or can be used to effect hemostasis, closing and/or sealing wounds and/or incisions, reinforce staple and/or suture lines, buttress natural tissue, and/or for any other suitable medical and/or surgical applications.

In some demonstrative embodiments, the composition may comprise a gelatin or collagen matrix with an enzymatic cross-linker, preferably microbial transglutaminase, e.g., integrated into the matrix.

In some demonstrative embodiments, the methods and/or devices described herein may include dry Gelatin-enzyme composition, for example, wherein the composition may form a patch.

In some demonstrative embodiments, the methods and/or devices described herein may include the addition of a mechanical backing layer to the basic gelatin-TG mixture, for example, to increase the hemostatic and/or fluid control capacity of the mixture, e.g., by slowing the fluid and/or allowing the gelatin-TG more time to cross-link and/or block the fluid leakage.

In some demonstrative embodiments, the methods and/or devices described herein may include dry Gelatin-enzyme composition that may include a degradable and/or non-degradable device incorporated into the gelatin matrix, for example, such that when the composition comes into contact with fluid, the device may be adhered to a tissue surface.

In some demonstrative embodiments, the methods and/or devices described herein may include dry gelatin-enzyme composition that may include a degradable and/or non-degradable device where the device may be a surgical mesh, for example, for the reinforcement of damaged tissue.

According to some preferred embodiments of the present invention, the gelatin-mTG mixture may be partially cross-linked prior to application to a wound site or prior to lyophilization. In another embodiment, non-cross-linked gelatin or mTG may be present together with partially cross-linked gelatin-mTG. In another embodiment, a non-cross-linked gelatin is present together with a mTG.

While a number of absorbable surgical hemostats are currently used in the surgical arena, no existing commercially available product is sufficiently strong to provide the mechanical and biological support necessary to control severe hemorrhage or vigorous flow of other biological fluids. Furthermore, no existing commercially available product can provide sufficient adhesive strength to strongly adhere implantable medical devices to tissue sites.

Though gelatin has been used in a variety of wound dressings, gelatin networks alone do not provide the mechanical properties necessary for controlling brisk bleeding.

Examples of gelatin dressings for hemostasis are disclosed in US Patent Applications 20110045034 and 20110021964 wherein the gelatin dressing absorbs fluids and a biologically active ingredient (preferably thrombin) is added to further promote hemostasis. As taught by these references, the gelatin matrix itself is insufficient to control brisk bleeding and the biologically active ingredient does not have any mechanical effect on the gelatin dressing, such that the gelatin matrix does not provide any structural or mechanical support to hemostasis, sealing and/or wound closure.

According to some embodiments of the present invention, there is provided a method of treating a wounded tissue, comprising applying to the tissue a composition comprising collagen or a collagen derivative and a non-toxic cross-linking agent.

Optionally, the non-toxic cross-linking agent may include one or more enzymes and/or an enzymatic composition. In some demonstrative embodiments, the one or more enzymes may include transglutaminase or a transglutaminase composition. Preferably, the weight ratio of gelatin to transglutaminase is in a range of from about 50:1 to about 500:1. More preferably, the transglutaminase composition has a specific activity level (enzyme units/protein content) of about at least 15 U/mg. Most preferably, the transglutaminase has a specific activity level of at least about 25 U/mg.

Optionally and preferably, the activity level of the transglutaminase in the gelatin-transglutaminase composition is from about 25 to about 1000 U/g of gelatin. More preferably, the activity level is from about 50 to about 400 U/g of gelatin.

Optionally, the transglutaminase composition may comprise a plant, recombinant animal, and/or microbe derived transglutaminase other than blood derived Factor XIII. Preferably, the composition has a pH in a range of from about 5 to about 8.

Optionally, the collagen and/or collagen-derivative may be produced from animal origin, recombinant origin or a combination thereof. Preferably, the animal origin is selected from the group consisting of fish and mammals. More preferably, the mammal is selected from the group consisting of pigs and cows.

Optionally, the collagen-derivative is a gelatin.

Optionally, the gelatin is of type A (Acid Treated) or of type B (Alkaline Treated). More preferably, the gelatin comprises high molecular weight gelatin.

Optionally, wounded tissue is selected from the group consisting of surgically cut tissue, surgically repaired tissue, and traumatized tissue.

Optionally, the method may further comprise reducing bleeding and/or leakage of other bodily fluids from the tissue. Optionally a bodily fluid is selected from the group consisting of cerebral spinal fluid, intestinal fluid, air, bile, and urine. Preferably, the method further comprises inducing hemostasis or stasis of other leaking bodily fluids in the tissue.

Optionally, the wound is bleeding or leaking another bodily fluid and treating the wounded tissue comprises applying the composition to the wound site to encourage in situ cross-linking between gelatin chains and the endogenous collagen of tissue extra-cellular matrix to create a barrier to fluid leakage or bleeding.

Optionally, the method further comprises forming an adhesive gel.

Optionally, applying the composition comprises: Mixing the gelatin and the transglutaminase to form a mixture; and applying the mixture to the tissue.

According to other embodiments of the present invention, there is provided a method for inducing hemostasis in a wound of a mammal, the method comprising applying to the wound a composition comprising gelatin and transglutaminase.

According to still other embodiments of the present invention, there is provided a method for inducing formation of a sealing matrix at a site of a damaged blood vessel, comprising applying to the wound a composition comprising gelatin and transglutaminase.

According to still other embodiments of the present invention, there is provided a composition comprising a combination of gelatin and transglutaminase, wherein a ratio of an amount of the gelatin and an amount of the transglutaminase is selected to induce formation of a sealing adhesive in a mammal.

According to still other embodiments of the present invention, there is provided a composition comprising a combination of gelatin and non-toxic cross-linking agent, wherein a ratio of an amount of the gelatin and an amount of the non-toxic cross-linking agent is sufficient to reduce bleeding in a wound of a mammal.

Preferably, the non-toxic cross-linking agent comprises transglutaminase. More preferably the weight ratio of gelatin to transglutaminase is in a range of from about 50:1 to about 500:1. Even more preferably, the transglutaminase composition has a specific activity level (enzyme units/protein content) of about at least 15 U/mg. Most preferably, the transglutaminase has a specific activity level of at least about 25 U/gm.

Optionally activity of the transglutaminase in the gelatin-transglutaminase composition is from about 25 to about 1000 U/g of gelatin. Preferably, the activity is from about 50 to about 400 U/g of gelatin.

Optionally, the transglutaminase comprises a plant, recombinant, animal, or microbe derived transglutaminase other than blood derived Factor XIII. Preferably, the composition further comprises a stabilizer or filler. Also preferably, the composition has a pH in a range of from about 5 to about 8.

Optionally, gelatin is produced from animal origin, recombinant origin or a combination thereof. Preferably, the animal origin is selected from the group consisting of fish and mammals. More preferably, the mammal is selected from the group consisting of pigs and cows. Most preferably, the gelatin comprises pig skins or pig bones, or a combination thereof. Also most preferably, the gelatin is of type A (Acid Treated) or of type B (Alkaline Treated). Also most preferably, the gelatin comprises high molecular weight gelatin.

Optionally, the gelatin has a bloom of at least about 250. Preferably, the fish comprises a cold water species of fish.

Optionally, recombinant gelatin is produced using bacterial, yeast, animal, insect, or plant systems or any type of cell culture.

Optionally, gelatin is purified to remove salts.

Optionally, gelatin has at least one adjusted, tailored or predetermined characteristic.

According to still other embodiments of the present invention, there is provided a hemostatic or body fluid sealing agent comprising a combination of gelatin and a non-toxic cross-linking agent. Optionally, the non-toxic cross-linking agent comprises transglutaminase. Preferably, the combination comprises aggregated gelatin and transglutaminase.

As described herein, a method or composition in which the transglutaminase may optionally be extracted from one or more of Streptoverticillium mobaraense, Streptoverticillium Baldaccii, a *Streptomyces Hygroscopicus* strain, or *Escherichia Coli*.

According to still other embodiments of the present invention, there is provided a method of inducing hemostasis in and/or sealing a wounded tissue, comprising applying to the tissue a composition comprising a cross-linking protein substrate and a non-toxic cross-linking agent. Optionally, the non-toxic cross-linking agent comprises transglutaminase.

Optionally the composition further comprises an additional hemostatic agent. Preferably the additional hemostatic agent further comprises one or more of albumin, collagen, fibrin, thrombin, chitosan, ferric sulfate, or other metal sulfates.

According to other embodiments of the present invention there is provided a hemostatic or sealing dressing which comprises: (i) a first gelatin layer; (ii) a transglutaminase layer adjacent to the first gelatin layer; and (iii) a second gelatin layer adjacent to the transglutaminase layer, wherein the transglutaminase layer is coextensive or noncoextensive with the first gelatin layer and/or the second gelatin layer.

According to other embodiments of the present invention there is provided a hemostatic or sealing dressing which comprises: (i) a resorbable or non-resorbable material layer; (ii) a first gelatin layer adjacent to the material layer; (iii) a transglutaminase layer adjacent to the first gelatin layer; and (iv) a second gelatin layer adjacent to the transglutaminase layer, wherein the transglutaminase layer is coextensive or noncoextensive with the first gelatin layer and/or the second gelatin layer.

According to other embodiments of the present invention there is provided a hemostatic or sealing dressing which comprises: (i) a gelatin layer; (ii) a transglutaminase layer adjacent to the gelatin layer; wherein the transglutaminase layer is coextensive or noncoextensive with the gelatin layer.

According to other embodiments of the present invention there is provided a hemostatic or sealing dressing which comprises: (i) a resorbable or non-resorbable material layer; (ii) a gelatin layer adjacent to the material layer; (iii) a transglutaminase layer adjacent to the gelatin layer; wherein the transglutaminase layer is coextensive or noncoextensive with the gelatin layer.

According to other embodiments of the present invention there is provided a hemostatic or sealing dressing which comprises: (i) a gelatin layer; (ii) a resorbable or non-resorbable material layer adjacent to the first gelatin layer; (iii) a transglutaminase layer adjacent to the material layer; wherein the transglutaminase layer is coextensive or noncoextensive with the gelatin layer.

According to other embodiments of the present invention there is provided a hemostatic or sealing device which comprises: (i) a resorbable or non-resorbable matrix; (ii) gelatin;

(iii) a transglutaminase; wherein the gelatin and transglutaminase are incorporated within the matrix.

According to other embodiments of the present invention there is provided a hemostatic or sealing device which comprises: (i) a resorbable gelatin matrix; (ii) a transglutaminase; wherein the transglutaminase is incorporated within the gelatin matrix.

According to other embodiments of the present invention there is provided a hemostatic or sealing device which comprises: (i) a porous resorbable or non-resorbable matrix; (ii) gelatin; (iii) a transglutaminase; wherein the gelatin and transglutaminase are adhered to the matrix.

According to some demonstrative embodiments, the gelatin layer described hereinabove may optionally be foamed, for example, by mixing the gelatin solution with pressurized air and/or other gas prior to drying. In some embodiments, the gelatin foam may be in a density range of 5 to 100 mg/cm$^3$ and preferably in the range of 10 to 50 mg/cm$^3$.

Optionally, the dressing or device further comprises a backing material.

Preferably, the backing material is resorbable.

More preferably, the backing material is a cross-linked collagen or collagen-derivative.

According to other embodiments of the present invention, there is provided a medical device for insertion into a body of a human or lower mammal, comprising a hemostatic or sealing agent or composition as described herein. Preferably the device comprises a vascular catheter.

According to other embodiments of the present invention, there is provided an adhesive surgical mesh for reinforcement of injured tissue in the body of a human or lower mammal, comprising a resorbable or non-resorbable implantable mesh coated with a hemostatic or sealing agent or composition as described herein.

According to some embodiments of the present invention, there is provided a patch comprising an implantable surgical mesh, a cross-linkable protein matrix and a protein cross-linking enzyme in contact with said matrix for cross-linking said cross-linkable protein, wherein said matrix is incorporated into, layered on or surrounding said mesh, with the proviso that said enzyme is not thrombin.

Optionally said cross-linkable protein comprises gelatin. Optionally said cross-linkable protein matrix is porous. Optionally said porous matrix comprises foam. Optionally said enzyme is present in a layer that is co-extensive or non-coextensive with said matrix. Optionally said enzyme is incorporated either homogeneously throughout the matrix or present in the matrix at a depth of at least 0.5 mm from the matrix surface. Optionally said enzyme is present in said matrix at a depth of at least 1 mm. Optionally said enzyme is present in said matrix at a depth of up to 20 mm.

According to at least some embodiments of the present invention, there is provided a dressing comprising a cross-linkable protein layer and a cross-linking enzyme for cross-linking said cross-linkable protein, wherein said enzyme is present at a depth of at least 0.5 mm in said protein layer and wherein said enzyme is a non-blood derived enzyme.

Optionally said enzyme is present in said protein layer at a depth of at least 1 mm. Optionally said enzyme is present in said protein layer at a depth of up to 20 mm. Optionally said protein comprises gelatin, wherein said protein layer is optionally foamed or porous. Optionally the patch or dressing further comprises a reinforcing back layer.

According to at least some embodiments of the present invention, there is provided a patch, comprising a gelatin layer and a reinforcing back layer, wherein said gelatin layer comprises gelatin and an enzyme integrated into a carrier selected from a group consisting of: HPC (hydroxypropyl cellulose), HPMC (hydroxypropyl methylcellulose), carboxymethyl cellulose, hydroxylethyl cellulose, ethylcellulose, PVP (polyvinyl pyrrolidone), PVA (polyvinyl alcohol), PEG (polyethylene glycol), PEI (polyethyleneimine), starch, microcrystalline cellulose, oxidized cellulose.

Optionally said gelatin comprises foamed gelatin. Optionally said foamed gelatin comprises dried or lyophilized foamed gelatin solution. Optionally said enzyme is present in an enzymatic layer and wherein said gelatin is positioned in one or more of the following locations: within said patch or dressing, on said enzymatic layer, in said enzymatic layer, on said reinforcing back layer, in said reinforcing back layer, or between said an enzymatic layer and said reinforcing back layer.

Optionally said gelatin is foamed gelatin and wherein prior to foaming, the concentration of the gelatin solution is between 0.1% and 30% w/w. Optionally prior to foaming, the concentration of the gelatin solution is between 1% and 20% w/w. Optionally prior to foaming, the concentration of the gelatin solution is between 5% and 15% w/w.

Optionally said cross-linkable protein is present in a protein matrix and wherein said matrix has a density in a range of from 5 to 100 mg/cm3. Optionally said density is in a range of from 10 to 50 mg/cm3.

Optionally said foamed gelatin is produced according to a method selected from the group consisting of a batch mixing process, a continuous mixing process, a chemical foaming process, or a Venturi foaming process.

Optionally said protein comprises gelatin and wherein said enzyme comprises transglutaminase (TG). Optionally the gelatin is incorporated into a gelatin matrix with said transglutaminase such that one or more of the following occur: a majority of enzyme activity is preserved throughout a process of preparation; enzyme is equally distributed across the gelatin matrix surface; and/or enzyme is embedded into the depth of the gelatin matrix (gradient or equal distribution). Optionally said transglutaminase is incorporated into said gelatin matrix according to one or more of mixing before drying said matrix or after drying said matrix, optionally wherein said matrix is dried to comprise no more than 10% moisture content. Optionally a density of said matrix is in a range of 5-100 mg/cm3, or transglutaminase is present at a concentration of from 0.05 to 2 mg transglutaminase/cm3 gelatin matrix.

Optionally the patch or dressing further comprises a reinforcing backing layer and wherein a surgical mesh is present, wherein said surgical mesh is located at one or more of between the reinforcement layer and the gelatin matrix; in the middle of the gelatin matrix; or on top of the gelatin matrix; or a combination thereof.

Optionally the cross-linkable protein includes a plurality of moieties, and wherein more than 50% of said moieties are non-cross linked. Optionally the patch or dressing of further comprises a reinforcing back layer, wherein said reinforcing back layer comprises a resorbable material. Optionally said resorbable material is selected from the group consisting of cellulose, oxidized cellulose, proteinaceous substance, such as fibrin, keratin, collagen and/or gelatin, or a carbohydrate substances, such as alginates, chitin, cellulose, proteoglycans (e.g. poly-N-acetyl glucosamine), glycolic acid polymers, lactic acid polymers, or glycolic acid/lactic acid co-polymers.

Optionally said patch can close a tissue wound having burst pressure of at least 200 mmHg.

Optionally the patch or dressing features a mesh and is adapted for surgical mesh fixation where mesh can be adhered to an organ surface, tissue surface, or cavity.

Optionally the patch or dressing is adapted for inguinal, femoral, umbilical or incisional ventral hernia repair, or other types of surgical mesh reconstruction.

Optionally the patch or dressing is adapted for use with a reduced stapling or suturing procedure.

Optionally the patch or dressing is adapted for use with one or more of staples, tacks, or sutures to supplement mesh adhesion.

Optionally the patch or dressing further comprises a medical device integrated with said patch.

Optionally the patch or dressing is adapted for any of large diaphragmatic hernia repair, for rectopexy (rectal prolapsed) mesh fixation, for reconstruction of a prolapsed vaginal vault, or for other pelvic floor mesh reinforcement operations (gynecology procedures).

Optionally said mesh comprises any of a synthetic mesh, a biological mesh, or a combination synthetic-biological mesh.

Optionally the patch or dressing further comprises an additional agent selected from the group consisting of: an antibiotic, an anticoagulant, an steroid, a cardiovascular drug, a local anesthetic, a antiproliferative/antitumor drug, an antiviral, a cytokine, colony stimulating factors; erythropoietin; an antifungal; an antiparasitic agent; anti-inflammatory agents; anesthetics, such as bupivacaine; analgesics; antiseptics; and hormones.

Optionally the patch or dressing further comprises an additional agent selected from the group consisting of vitamins and other nutritional supplements; glycoproteins; fibronectin; peptides and proteins; carbohydrates (both simple and/or complex); proteoglycans; antiangiogenins; antigens; lipids or liposomes; and oligonucleotides (sense and/or antisense DNA and/or RNA).

Optionally said cytokine is selected from the group consisting of alpha- or beta- or gamma-Interferon, alpha- or beta-tumor necrosis factor, and interleukins.

Optionally said antiviral is selected from the group consisting of gangcyclovir, zidovudine, amantidine, vidarabine, ribaravin, trifluridine, acyclovir, dideoxyuridine and antibodies to viral components or gene products. Optionally said anti-tumor drug is selected from the group consisting of 5-fluorouracil (5-FU), taxol and/or taxotere.

Optionally said cardiovascular drug is selected from the group consisting of calcium channel blockers, vasodilators and vasoconstrictors; chemoattractants.

Optionally said steroid is selected from the group consisting of dexamethasone, inhibitors of prostacyclin, prostaglandins, leukotrienes and/or kinins to inhibit inflammation.

Optionally said anticoagulant is selected from the group consisting of activated protein C, heparin, prostracyclin (PGI2), prostaglandins, leukotrienes, antitransglutaminase III, ADPase, and plasminogen activator.

Optionally said antibiotic is selected from the group consisting of tetracycline, ciprofloxacin, amoxicillin, and metronidazole.

Optionally the patch or dressing further comprises a wound healing agent.

Optionally the patch or dressing further comprises a hemostatic agent.

According to at least some embodiments of the present invention, there is provided a method of producing a patch or a dressing, comprising: producing a cross-linkable protein matrix, comprising a cross-linkable protein; depositing an enzymatic composition in said protein matrix at a depth of at least 0.5 mm, wherein said enzymatic composition comprises an enzyme capable of cross-linking said cross-linkable protein; thereby producing the patch or dressing.

Optionally said cross-linkable protein comprises gelatin in the form of a gelatin solution, comprising mixing said gelatin solution in a mixer at a rate to form a foamed solution, drying said foamed solution to form a dried solution and combining said dried solution with said enzyme.

Optionally said mixing said gelatin solution comprises mixing said gelatin solution in a mixer with pressurized air, at a mixing rate and air pressure so as to foam the solution; wherein said method further comprises lyophilizing the foamed gelatin solution to form a lyophilized layer of gelatin solution.

Optionally said rate is from 100 RPM to 10,000 RPM. Optionally said rate is from 1000 RPM to 6000 RPM.

Optionally said rate is from 0.1 cm3/second to 10,000 cm3/second per volume of foam.

Optionally said cross-linkable protein comprises gelatin in the form of a gelatin solution, comprising mixing said gelatin solution with a chemical foaming agent so as to foam the solution; wherein said method further comprises drying the foamed gelatin solution to a dried layer of gelatin solution.

Optionally said chemical foaming agent comprises sodium bicarbonate and wherein the mixture of the gelatin solution and the sodium bicarbonate has a pH below 7.

Optionally said cross-linkable protein comprises gelatin in the form of a gelatin solution, comprising forcing said gelatin solution through a tube having a plurality of holes at a rate and pressure so as to foam the solution; wherein said method further comprises drying the foamed gelatin solution to form a dried layer of gelatin solution.

Optionally the method further comprises producing a gelatin layer by mixing a gelatin solution with said enzyme, said enzyme comprising transglutaminase, to form a foamed gelatin solution; wherein said method further comprises lyophilizing the foamed gelatin solution to form a lyophilized foamed gelatin solution and adding said lyophilized foamed gelatin solution to said patch or dressing.

Optionally said transglutaminase is added to said gelatin solution prior to said mixing or during said mixing. Optionally said transglutaminase is added to said gelatin solution through continuous streaming during mixing.

Optionally the method further comprises cooling said foamed gelatin solution before said lyophilizing is performed. Optionally the method further comprises foaming a gelatin solution to form a foamed gelatin solution; drying the foamed gelatin solution to form said dried foamed gelatin solution; and adding said transglutaminase in a solution to said dried foamed gelatin solution to form an enzyme containing foam.

Optionally said transglutaminase to said dried solution comprises one or more of spraying an enzyme solution onto dry gelatin matrix surface; injecting an enzyme solution into the gelatin matrix through needles or matrix of needles; submersing dry gelatin matrix into an enzyme-containing solvent mixture; and/or dispensing enzyme-containing solvent mixture onto dry gelatin matrix.

Optionally the method further comprises drying said enzyme containing foam.

Optionally said drying said enzyme containing foam comprises one or more of air drying, vacuum drying, lyophilization and/or heat drying.

Optionally said enzyme comprises transglutaminase and said transglutaminase comprises any type of calcium dependent or independent transglutaminase (mTG). Optionally said transglutaminase comprises a microbial transglutaminase.

Optionally drying occurs at a temperature of up to 30 C. Optionally said drying occurs at a temperature of up to 20 C. Optionally said drying occurs at a plurality of temperatures ranging from 0 C to 20 C.

Optionally the patch or dressing comprises a plurality of gelatin layers and wherein optionally each of said gelatin layers has a different percentage concentration of gelatin. Optionally at least one gelatin layer comprises a percentage of gelatin of from about 1% w/w to about 15% w/w. Optionally at least one gelatin layer comprises a percentage of gelatin of from about 2.5% w/w to about 10% w/w. Optionally at least one gelatin layer comprises a percentage of gelatin of at least about 5% w/w.

Optionally at least one gelatin layer comprises a lubricant. Optionally said lubricant comprises glycerol. Optionally said glycerol is present in an amount of from 0.1% to 10%. Optionally said glycerol is present in an amount of from 2% to 6%.

Use of a patch or dressing as described herein, for the treatment of chronic wounds. Optionally said chronic wounds include diabetic skin ulcers According to at least some embodiments of the present invention, there is provided a method of treating chronic wounds in a patient in need thereof comprising adhering to said chronic wounds a patch or dressing according to any of the above claims. Optionally said chronic wounds include diabetic skin ulcers.

According to at least some embodiments of the present invention, there is provided a hemostatic dressing, tissue adhesive or wound closure composition comprising a cross-linkable porous protein matrix and a non blood-derived enzyme which induces cross-linking of the cross-linkable protein, wherein matrix density is in range of 5-100 mg/cm3. Optionally said density is in a range of 40-70 mg/cm3. Optionally the patch or dressing has a total moisture content of less than 30%, a total moisture content of less than 20% or a total moisture content of less than 10%.

Optionally a ratio of enzyme to matrix is from 0.05 to 5 mg/cm3 enzyme/cm3 matrix. Optionally said ratio is 0.5 to 2.5 mg/cm3 enzyme/cm3 matrix.

Optionally the solution comprises an emulsion or suspension.

Optionally the patch or dressing further comprises a reinforcing back layer, wherein said reinforcing back layer comprises a non-resorbable material.

Optionally said non-resorbable material is selected from the group consisting of silicone, latex, polyurethane, polypropylene, polyethylene, silastic, polyethylene tecephtalate (PET), dacron, knitted dacron, velour dacron, polyglacin, nylon, polyvinyl chloride silastic elastomer, PMMA [poly(methyl methacrylate), polyofefin, cellulose, poly vinyl]alcohol (PVA), poly(hydroxyethyl Methacrylate (PHEMA), poly (glycolic acid), poly(acrylonitrile) (PAN), fluoroethylene-cohexa-fluoropropylene (FEP), teflon (PTFE), Co—Cr alloys, copolymers thereof and mixtures thereof.

Optionally said cross-linkable protein is provided as a protein matrix, further comprising a reinforcing back layer, wherein said reinforcing back layer is mechanically modified so as to increase surface area of protein matrix interface with back layer.

Optionally said mechanical modification comprises one r or more of being etched, carved, cut, engraved, or textured.

According to at least some embodiments, there is provided a method of producing a patch or dressing according to any of the above claims, wherein the enzyme solution or enzyme-containing solvent solution comprises enzyme in a solution or suspension incorporating one or more volatile solvents.

Optionally the volatile solvent comprises one or more of ethyl acetate, benzene, methylene chloride, acetone, acetonitrile, chloroform, volatile liquid silicones (hexamethyldisiloxane (HMDS), octamethylcyclotetrasiloxane, decamethylcyclopentasiloxane, octamethyltrisiloxanes), volatile alkanes (n-hexane, isooctane, octane, neopentane), volatile fluorocarbons (pentafluoropropane, perfluoroheptane, perfluoromethylcyclohexane), alcohols (1-propanol, 2-propanol, ethanol) and mixtures thereof.

Optionally the enzyme is encapsulated prior to incorporation in the patch or dressing. Optionally the enzyme is encapsulated in a material selected from the group consisting of: PLA, PGA, PLGA, k-carrageenan, liposomes, gelatin, collagen, fibrinogen, albumin, polyethylene glycol, polyvinyl alcohol, cellulose ethers.

Optionally the enzyme is encapsulated by a technique selected from the group consisting of: vibrational nozzle and spray drying, pan coating, air suspension coating, centrifugal extrusion (co-extrusion), physico-chemical methods (ionotropic gelation or coaceravation), chemical methods (interfacial polycondensation, interfacial cross-linking, in situ polymerization and matrix polymerization).

Optionally the enzyme is chemically modified prior to incorporation in the patch or pressing.

Optionally the patch or dressing is sterilized to a sterility assurance level of 10-6 through exposure to electron beam radiation. Optionally the radiation dosage is in the range of 10-50 kGy. Optionally the radiation dosage is in the range of 20-40 kGy.

Optionally the patch or dressing further comprises a radioprotectant selected from the group consisting of Ascorbate, Benzyl alcohol, Benzyl benzoate, Butylated Hydroxyanisole (BHA), Chlorobutanol, Cysteine, Mannitol, Methyl paraben, Niacinamide, Phenol, Propylene glycol, Propyl gallate, Propyl paraben, Sodium bisulfate, Sodium metabisulfite, Sodium salicylate, Sodium thiosulfate, Tocopherol, Trehalose.

Optionally the patch or dressing further comprises a buffer optionally selected from the group including Sodium Acetate, HEPES, Sodium Citrate, Sodium Benzoate.

Optionally the patch or dressing further comprises one or more plasticizers and/or flexibility enhancers, optionally selected from the group consisting of Glycerol, Polyethylene Glycol (PEG), Polyvinyl Alcohol (PVA), Polysorbate 20, Polysorbate 80;

Optionally the patch or dressing further comprises one or more foaming stabilizers, optionally selected from the group consisting of Ionic surfactants (i.e. SDS), Hydroxyl Propyl Methyl Cellulose, Hyaluronic Acid, Glycine, Dextran.

Optionally a plurality of discrete enzyme-containing protein matrix segments together form a single patch or dressing. Optionally each segment is of diameter in range of 0.1 to 10 cm. Optionally each segment is of diameter in range of 1-5 cm.

It is to be understood that both the foregoing general description and the following detailed description are exemplary and explanatory only and are intended to provide further explanation of the invention as claimed.

Unless defined otherwise, all technical and scientific terms used herein have the same meaning as is commonly understood by one of skill in the art to which this invention belongs. All patents, patent applications, and publications mentioned herein are incorporated herein by reference.

As used herein, a transglutaminase layer that is said to be "noncoextensive" with a gelatin layer is one in which the spatial boundaries of the transglutaminase layer in two dimensions are smaller than the spatial boundaries of one or both gelatin layers such that the transglutaminase layer is coextensive with only about 5% to about 95% of the surface area of the first gelatin layer of the hemostatic dressing and/or coextensive with only about 5% to about 95% of the surface layer of the second gelatin layer of the hemostatic dressing, independently. For example, the transglutaminase layer can be coextensive with about 10, 20, 30, 40, 50, 60, 70, 75, 80, or 90% of the surface area of each of the first and second gelatin layers, independently. A transglutaminase layer that is "coextensive" with a gelatin layer provides full coverage of the gelatin layer and is coextensive with 100% of the surface area of the gelatin layer. A transglutaminase layer can be noncoextensive with the first gelatin layer and yet be coextensive with the second gelatin layer, or vice versa, e.g., by employing gelatin layers having different total surface areas or shapes.

"Patient" as used herein refers to human or animal individuals in need of medical care and/or treatment.

"Wound" as used herein refers to any damage to any tissue of a patient that results in the loss of blood from the circulatory system or the loss of any other bodily fluid from its physiological pathway. The tissue can be an internal tissue, such as an organ or blood vessel, or an external tissue, such as the skin. The loss of blood or bodily fluid can be internal, such as from a ruptured organ, or external, such as from a laceration. A wound can be in a soft tissue, such as an organ, or in hard tissue, such as bone. The damage may have been caused by any agent or source, including traumatic injury, infection or surgical intervention. The damage can be life-threatening or non-life-threatening.

"Resorbable material" as used herein refers to a material that is broken down spontaneously and/or by the mammalian body into components which are consumed or eliminated in such a manner as not to interfere significantly with wound healing and/or tissue regeneration, and without causing any significant metabolic disturbance.

"Stability" as used herein refers to the retention of those characteristics of a material that determine activity and/or function.

"Binding agent" as used herein refers to a compound or mixture of compounds that improves the adherence of one layer of the hemostatic dressing to one or more different layers and/or the adherence of the components of a given layer to other components of that layer.

"Solubilizing agent" as used herein refers to a compound or mixture of compounds that improves the dissolution of a protein or proteins in a (preferably) aqueous solvent.

"Filler" as used herein refers to a compound or mixture of compounds that provide bulk and/or porosity to one or more layers of the hemostatic dressings.

"Release agent" as used herein refers to a compound or mixture of compounds that facilitates removal of an hemostatic dressing from a manufacturing mold.

"Foaming agent" as used herein refers to a compound or mixture of compounds that produces gas when hydrated under suitable conditions.

"TG" refers to transglutaminase of any type; "mTG" may also refer to microbial transglutaminase and/or to any type of transglutaminase, depending upon the context (in the specific experimental Examples below, the term refers to microbial transglutaminase).

The term "mammal", particularly with regard to method of treatment and/or use or application of a device and/or composition, refers to both humans and lower mammals, unless otherwise specified.

As used herein, "about" means plus or minus approximately ten percent of the indicated value.

Other features and advantages of the invention will be apparent from the following detailed description, and from the claims.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3 shows the perforator used in example #4.

FIG. 4 shows the flowchart for example #4.

DETAILED DESCRIPTION OF THE INVENTION

Figure 1:
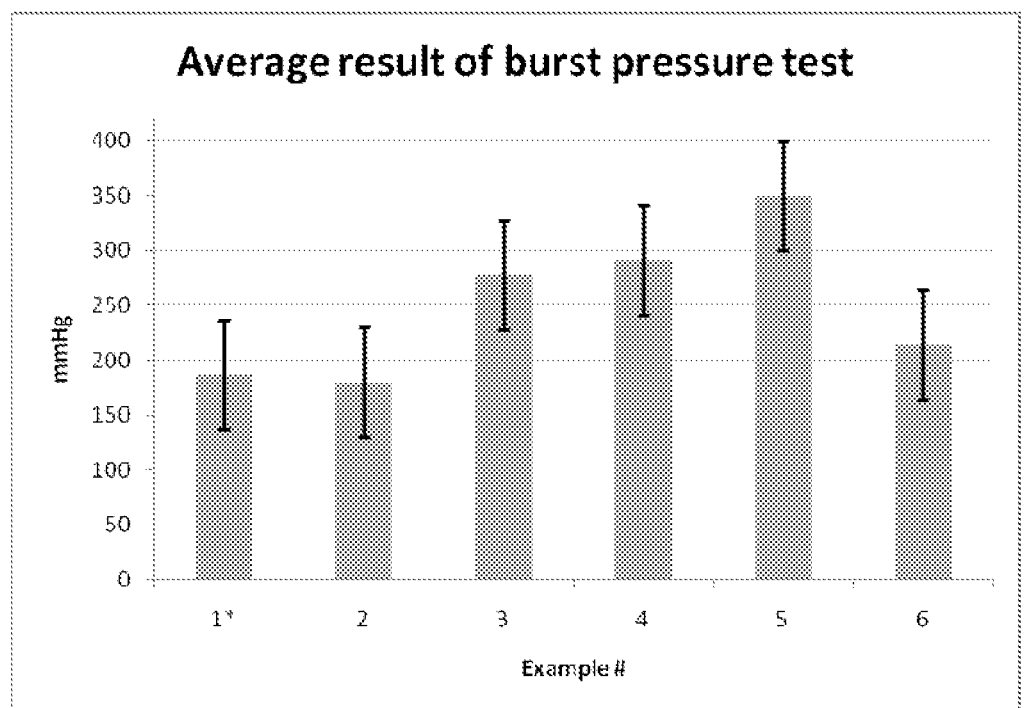
FIG. 1 shows the results of burst pressure tests for the compositions of Examples 1-6; the results of example #1 are according to the basic burst pressure test, while the results of example #2-6 are according to the advanced BP test.

The present invention, in at least some embodiments, is of an adhesive material which comprises a cross-linkable protein and a non-toxic material which induces cross-linking of the cross-linkable protein. Preferably, the cross-linkable protein includes gelatin and any gelatin variant or variant protein as described herein. Optionally and preferably, the non-toxic material comprises an enzyme, more preferably, the non-toxic material comprises transglutaminase (TG), which may optionally comprise any type of calcium dependent or independent transglutaminase (mTG), which may for example optionally be a microbial transglutaminase. According to some embodiments of the present invention, the adhesive material is provided in a bandage, which is preferably adapted for use as a hemostatic bandage. Various embodiments of the present invention are described in greater detail below, under section headings which are provided for the sake of clarity only and without any intention of being limiting in any way.

Gelatin and Transglutaminase

According to preferred embodiments of the present invention, there is provided a composition for hemostasis and tissue sealing in which the cross-linking material comprises transglutaminase and the cross-linkable protein comprises gelatin.

According to a preferred embodiment, transglutaminase is present at a specific activity level of at least about 15 U/mg.

Suitable gelatin and transglutaminase can be obtained by any of the methods known and available to those skilled in the art. Gelatin may optionally comprise any type of gelatin which comprises protein that is known in the art, preferably including but not limited to gelatin obtained by partial hydrolysis of animal tissue and/or collagen obtained from animal tissue, including but not limited to animal skin, connective tissue (including but not limited to ligaments, cartilage and the like), antlers or horns and the like, and/or bones, and/or fish scales and/or bones or other components; and/or a recombinant gelatin produced using bacterial, yeast, animal, insect, or plant systems or any type of cell culture.

According to preferred embodiments of the present invention, gelatin from animal origins preferably comprises gelatin from mammalian origins and more preferably comprises one or more of pork skins, pork and cattle bones, or split cattle hides, or any other pig or bovine source. More preferably, such gelatin comprises porcine gelatin since it has a lower rate of anaphylaxis. Gelatin from animal origins may optionally be of type A (Acid Treated) or of type B (Alkaline Treated), though it is preferably type A.

Preferably, gelatin from animal origins comprises gelatin obtained during the first extraction, which is generally performed at lower temperatures (50-60° C., although this exact temperature range is not necessarily a limitation). Gelatin produced in this manner will be in the range of 250-300 bloom and has a high molecular weight of at least about 95-100 kDa. Preferably, 275-300 bloom gelatin is used.

A non-limiting example of a producer of such gelatins is PB Gelatins (Tessenderlo Group, Belgium).

According to some embodiments of the present invention, gelatin from animal origins optionally comprises gelatin from fish. Optionally any type of fish may be used, preferably a cold water variety of fish such as carp, cod, or pike, or tuna. The pH of this gelatin (measured in a 10% solution) preferably ranges from 4-6.

Cold water fish gelatin forms a solution in water at 10° C. and thus all cold water fish gelatin are considered to be 0 bloom. For the current invention, a high molecular weight cold water fish gelatin is preferably used, more preferably including a molecular weight of at least about 95-100 kDa. This is equivalent to the molecular weight of a 250-300 bloom animal gelatin. A non-limiting example of a producer of such a gelatin is Norland Products (Cranbury, N.J.).

In a preferred embodiment of the invention, the gelatin is purified to remove salts. This can be accomplished according to previously described techniques. One such technique involves forming a 20% w/v solution of gelatin in water and heating it to 60° C. under stirring. The mixture is then let to stand still overnight. The gel obtained is dialysed against repeated changes of deionized water to eliminate salts, stirred and heated to 50° C. to disaggregate the physical network. The final solution was filtered and freeze-dried. (Crescenzi V, Francescangeli A, Taglienti A. (2002). Biomacromolecules. 3:1384-1391). Alternatively, the gelatin can be desalted by size exclusion column.

According to some embodiments of the present invention, a recombinant gelatin is used. Recombinant gelatins are currently commercially produced by FibroGen (San Francisco, Calif.). The currently preferred method is using a recombinant yeast system (*Pichia Pastoris*) to express specified fragments of Type I, alpha1 human sequence collagen.

In an optional but preferred embodiment of the present invention, recombinant gelatins are fully synthetic molecules, containing no contaminating components from humans or any animals. By "synthetic" it is meant that the gelatin is preferably produced according to a method selected from chemical synthesis, cell free protein synthesis, cell tissue culture, any type of bacterial, insect or yeast culture, or in plants. The use of synthetic gelatins eliminates many of the variables and drawbacks associated with tissue-derived materials, including provoking unwanted immune responses. For example, fish gelatins demonstrate high allergenicity and animal gelatins demonstrate low-moderate allergencity, while recombinant gelatins can have zero allergenicity. In human safety studies, no adverse events related to recombinant gelatin were found.

Methods of creating recombinant gelatins and the benefits of their use are fully described in U.S. Pat. Nos. 6,413,742 and 6,992,172, which are hereby incorporated by reference as if fully set forth herein.

Recombinant gelatins can be produced to be highly (99%) purified. Recombinant gelatin production allows for the optional production of gelatins with at least one defined and predetermined characteristic, including but not limited to defined molecular weights, pI (isoelectric point), guaranteed lot-to-lot reproducibility, and the ability to tailor the molecule to match a specific application.

An example of tailoring a molecule to match a specific application has been previously described wherein a gelatin was created to be highly hydrophilic (Werten M W T, et al. (2001). *Protein Engineering*. 14 (6): 447-454). Optionally and preferably a gelatin according to the present invention comprises a gelatin having at least one adjusted, tailored or predetermined characteristic.

The gelatin employed in the hemostatic dressing can be a gelatin complex or any gelatin, or a derivative or metabolite thereof, or a gelatin produced according to a single process or a plurality of processes. For example, the gelatin may optionally comprise gelatin type A or gelatin type B, or a combination thereof.

The transglutaminase may optionally comprise any plant, animal, or microbe derived transglutaminase, preferably other than blood derived Factor XIII. Preferably, microbial transglutaminase derived from Streptoverticillium mobaraensis is used.

The transglutaminase may optionally be in a composition comprising at least one other substance, such as a stabilizer or filler for example. Non-limiting examples of such materials include maltodextrin, hydrolyzed skim milk protein or any other protein substance, sodium chloride, safflower oil, trisodium phosphate, sodium caseinate or lactose, or a combination thereof.

Although the optimal pH for activity of crude transglutaminase is 6.0, it also functions with high activity in the range of pH 5.0 to pH 8.0. Therefore, a composition according to the present invention for hemostasis preferably has a pH value in a range of from about 5 to about 8.

Transglutaminase features a negative temperature coefficient. Over the temperature range of the transglutaminase activity, it takes a shorter time to react at higher temperatures and longer amount of time to start functioning at lower temperatures. The following table shows different reaction times at different temperatures comparing the same reaction grade as the reaction at 50° C., pH 6.0 that occurs in 10 minutes:

TABLE 1 reaction temperature of transglutaminase

| | Temperature | | | | |
|---|---|---|---|---|---|
| | 5° C. | 15° C. | 20° C. | 30° C. | 40° C. |
| Time (minutes) | 240 | 105 | 70 | 35 | 20 |

Non-limiting examples of commercially available transglutaminase products include those produced by Ajinomoto Co. (Kawasaki, Japan). A preferred example of such a product from this company is the Activa TG-TI (In Europe: Activa WM)—Ingredients: mTG and maltodextrin; Activity: 81-135 U/g of Activa. Other non-limiting examples of suitable products from this company include Activa TG-FP (ingredients: hydrolyzed skim milk protein, mTG; activity: 34-65 U/g of Activa TG-FP); Activa TG-GS (ingredients: sodium chloride, gelatin, trisodium phosphate, maltodextrin, mTG, and safflower oil (processing aid); activity: 47-82 U/g of Activa TG-GS); Active TG-RM (In Europe: Activa EB)—ingredients: sodium caseinate, maltodextrin, and mTG; activity: 34-65 U/g of Activa; Activa MP (ingredients: mTG, Lactose and Maltodextrin; activity: 78-126 U/g of Activa).

Other non-limiting examples of commercially available transglutaminase products include those produced by Yiming Biological Products Co. (Jiangsu, China). A preferred example of such a product from this company is the TG-B (ingredients: 1% mTG, 99% co-protein; activity: 80-130 U/g of TG-B). Other non-limiting examples of suitable products from this company include TG-A (ingredients: 0.5% mTG, 99.5% co-protein; activity: 40-65 U/g of TG-A).

For both examples, preferred transglutaminase products are those with the highest specific activity and simplest co-ingredients, as they are believed (without wishing to be limited by a single hypothesis) to have the best reactivity upon application and a lower potential for undesired side effects.

In another embodiment, a transglutaminase may optionally be extracted from Streptoverticillium Baldaccii or a *Streptomyces Hygroscopicus* strain to produce enzyme variants that have been shown to function optimally at lower temperatures (approximately 37° C. and 37° C.-45° C., respectively) (Negus SS. A Novel Microbial Transglutaminase Derived From Streptoverticillium Baldaccii. PhD Thesis. School of Biomolecular and Biomedical Science. Griffith University, Queensland, Australia and Cui L et al. Purification and characterization of transglutaminase from a newly isolated *Streptomyces hygroscopicus*. 2007: 105(2). p. 612-618.). Higher specific activity at lower temperatures is desirable for achieving faster and stronger cross linking of the gelatin under ambient conditions.

According to some embodiments, transglutaminase can be used in the form of any of the above described compositions, optionally including any of the commercially available mixtures that include transglutaminase.

In another embodiment, any of the above transglutaminase mixtures may optionally be purified by means of gel filtration, cation-exchange chromatography, hollow fiber filtration, or tangential flow filtration to remove their carrier proteins and/or carbohydrates. Some of these methods have been previously described (Bertoni F, Barbani N, Giusti P, Ciardelli G. Transglutaminase reactivity with gelatine: perspective applications in tissue engineering. *Biotechnol Lett* (2006) 28:697-702) (Broderick E P, et al. Enzymatic Stabilization of Gelatin-Based Scaffolds *J Biomed Mater Res* 72B: 37-42, 2005). The filter pore size used for filtration is preferably approximately 10 kDA.

Preferably, the transglutaminase is purified in a process that includes cation-exchange chromatography, hydrophobic chromatography, and ultrafiltration, as described more fully in PCT Application No. PCT/IB2009/052605, filed on Jun. 18, 2009, owned in common with the present application and having at least some inventors in common with the present application.

Regardless, the activity of transglutaminase is preferably measured prior to use and/or manufacture of a composition according to the present invention with a transglutaminase reactivity assay. Such an assay may optionally include but is not limited to the Hydroxamate Method, Nessler's Assay, a Colorimetric Assay, or any other assay of transglutaminase activity (see for example Folk J E, Cole P W. Transglutaminase: mechanistic features of the active site as determined by kinetic and inhibitor studies. *Biochim Biophys Acta*. 1966; 122:244-64; or the Nessler Assay as described in: Bertoni F, Barbani N, Giusti P, Ciardelli G. Transglutaminase reactivity with gelatine: perspective applications in tissue engineering. *Biotechnol Lett* (2006) 28:697-702).

In general, the purity and/or quality of the gelatin and/or the transglutaminase for use in the hemostatic composition will be of an appropriate purity known to one of ordinary skill in the relevant art to lead to efficacy and stability of the protein.

One or more supplements can also be contained in the hemostatic or sealing product, e.g., drugs such as growth factors, polyclonal and monoclonal antibodies and other compounds. Illustrative examples of such supplements include, but are not limited to: antibiotics, such as tetracycline and ciprofloxacin, amoxicillin, and metronidazole; anticoagulants, such as activated protein C, heparin, prostracyclin ($PGI_2$), prostaglandins, leukotrienes, antitransglutaminase III, ADPase, and plasminogen activator; steroids, such as dexamethasone, inhibitors of prostacyclin, prostaglandins, leukotrienes and/or kinins to inhibit inflammation; cardiovascular drugs, such as calcium channel blockers, vasodilators and vasoconstrictors; chemoattractants; local anesthetics such as bupivacaine; and antiproliferative/antitumor drugs such as 5-fluorouracil (5-FU), taxol and/or taxotere; antivirals, such as gangcyclovir, zidovudine, amantidine, vidarabine, ribaravin, trifluridine, acyclovir, dideoxyuridine and antibodies to viral components or gene products; cytokines, such as alpha- or beta- or gamma-Interferon, alpha- or beta-tumor necrosis factor, and interleukins; colony stimulating factors; erythropoietin; antifungals, such as diflucan, ketaconizole and nystatin; antiparasitic agents, such as pentamidine; anti-inflammatory agents, such as alpha-1-anti-trypsin and alpha-1-antichymotrypsin; anesthetics, such as bupivacaine; analgesics; antiseptics; and hormones. Other illustrative supplements include, but are not limited to: vitamins and other nutritional supplements; glycoproteins; fibronectin; peptides and proteins; carbohydrates (both simple and/or complex); proteoglycans; antiangiogenins; antigens; lipids or liposomes; and oligonucleotides (sense and/or antisense DNA and/or RNA).

Enzyme Integration

The enzyme may optionally be integrated into a carrier, including without limitation a dry carrier (including but not limited to a powder or a matrix) or a liquid carrier (including without limitation any type of suitable solvent).

With regard to the carrier, the enzyme may optionally be integrated to one or more carrier materials, including but not limited to any type of cellulosic polymer (including but not limited to one or more of HPC (hydroxypropyl cellulose), HPMC (hydroxypropyl methylcellulose), carboxymethyl cellulose, hydroxylethyl cellulose or ethylcellulose); PVP (polyvinyl pyrrolidone); starch; microcrystalline cellulose; and the like.

Optionally the carrier may further comprise a filler. Examples of suitable fillers include microcrystalline cellulose, sodium carboxymethylcellulose, ethylcellulose, cellulose acetate, starch, lactose, glucose, fructose, sucrose, dicalcium phosphate, sorbitol, manitol, mantitol, lactitol, xylitol, isomalt, erythritol, and hydrogenated starch hydrolysates, or a mixture thereof.

In some demonstrative embodiments the enzyme may optionally be integrated into a carrier (for example, HPMC) that may then be layered or embedded into and/or on the gelatin matrix, for example, before and/or after drying of the gelatin matrix.

The carrier may also optionally comprise one or more solvents, including but not limited to ethanol and acetonitrile, optionally in combination. These solvents may optionally be used as carriers for the enzyme, which may then optionally be dripped, sprayed or otherwise combined with one or more other layers of a bandage, patch or other composition (for example, by being dripped, sprayed or otherwise combined with a gelatin layer).

Other examples of volatile solvents which may optionally be employed include but are not limited to one or more of ethyl acetate, benzene, methylene chloride, acetone, chloroform, volatile liquid silicones (hexamethyldisiloxane (HMDS), octamethylcyclotetrasiloxane, decamethylcyclopentasiloxane, octamethyltrisiloxanes), volatile alkanes (n-hexane, isooctane, octane, neopentane), volatile fluorocarbons (pentafluoropropane, perfluoroheptane, perfluoromethylcyclohexane), alcohols (including but not limited to one or more of 1-propanol, 2-propanol, ethanol) and mixtures thereof.

In some demonstrative embodiments the enzyme may optionally be provided as a powder which is then combined with a carrier such as ethanol (whether dissolved or in suspension) for spraying, dripping and so forth.

Composition Preparation

In another embodiment of the invention, gelatin in the gelatin-mTG mixture is subjected to one or more drying methods that involve the use of lyophilization prior to its mixture with the mTG. These drying methods increase the solubility of gelatin by increasing the surface area of the dry gelatin matrix. The drying methods can increase gelatin's solubility without any additives and without altering the environmental conditions under which gelatin or gelatin-mTG solutions are formed. Nonetheless, the addition of certain additives, such as plasticizers or stabilizers, or the manipulation of certain environmental factors, such as temperature, ion concentration, and osmotic pressure, of the gelatin or gelatin-mTG solutions may be used to further enhance the properties of a gelatin-mTG mixture that already incorporates gelatin dried using a lyophilization technique that reduces its melting point.

Pre-Mixed Lyophilized Gelatin-mTG

In another embodiment of the invention, the gelatin-mTG mixture is subjected to lyophilization once the gelatin and mTG have already been mixed in solution. This results in an evenly mixed, lyophilized gelatin-mTG mixture where the gelatin in dry form is in contact with the mTG in dry form. In this embodiment, the gelatin and mTG are simultaneously reconstituted from lyophilized state and immediately form a solution at the site of reconstitution. This technique can preferentially be used with gelatin or a gelatin mixture that already has a lower melting point than standard gelatin since the activity of mTG decreases exponentially at lower temperatures (below about 37° C.).

Thus, a solution consisting of reduced-melting point gelatin and mTG can be formed at a low temperature without rapid cross-linking and without the occurrence of gelation. This solution can then be lyophilized, resulting in a dried mixture of homogenously distributed gelatin and mTG. Such a mixture can be rapidly reconstituted to form a gel when put in contact with a warmer solvent. Such a technique could preferentially be used in a wound dressing, where bodily fluids at their natural temperature of 37° C. can reconstitute the gelatin and mTG.

In another embodiment of the current invention, one or more of the above-described techniques for enhancing a product containing gelatin and mTG are used in unison or in series. This can preferentially include using two or more plasticizers together in a gelatin or gelatin-mTG solution, using one or more plasticizers in a gelatin or gelatin-mTG solution prior to drying it. It can also include drying the gelatin or gelatin-mTG, dissolving the dried gelatin or gelatin-mTG in solution, and then re-drying the gelatin or gelatin-mTG.

Bandages

An exemplary embodiment of the present invention is directed to a hemostatic dressing, e.g., for treating wounded tissue in a patient, which comprises gelatin and transglutaminase, preferably separated until their interaction is required or desired for the activity of the bandage. The bandage may optionally feature a non-absorbent backing, such as a plastic backing. The bandage may also optionally feature a resorbable material layer.

Another embodiment of the present invention is directed to a hemostatic dressing for treating wounded tissue in a patient which optionally and preferably comprises: (i) a gelatin layer; (ii) a transglutaminase layer adjacent to said gelatin layer; wherein the transglutaminase layer is coextensive or non-coextensive with the gelatin layer.

Another embodiment of the present invention is directed to a hemostatic dressing for treating wounded tissue in a patient which optionally and preferably comprises: (i) a resorbable or non-resorbable material layer; (ii) a gelatin layer adjacent to said material layer; (iii) a transglutaminase layer adjacent to said gelatin layer; wherein the transglutaminase layer is coextensive or noncoextensive with the gelatin layer.

Another embodiment of the present invention is directed to a hemostatic dressing for treating wounded tissue in a patient which comprises: (i) a first gelatin layer; (ii) a resorbable material layer adjacent to the first gelatin layer; (iii) a transglutaminase layer adjacent to the resorbable material layer; and (iv) a second gelatin layer adjacent to the transglutaminase layer, wherein the transglutaminase layer is noncoextensive with the first and/or second gelatin layers.

According to some embodiments, the present invention provides a hemostatic dressing (e.g., a bandage) that includes a layer of transglutaminase sandwiched between a first and a second layer of gelatin, wherein the transglutaminase layer may be coextensive or noncoextensive with the first and/or second gelatin layer. Such a hemostatic dressing is useful for treating wounds.

According to other embodiments of the present invention, there is provided a dressing of the invention which optionally and preferably comprises: (i) a resorbable or non-resorbable matrix; (ii) gelatin; (iii) a transglutaminase; wherein the gelatin and transglutaminase are incorporated within said matrix.

In another embodiment, the hemostatic device comprises: (i) a porous resorbable or non-resorbable matrix; (ii) gelatin;

(iii) a transglutaminase; wherein the gelatin and transglutaminase are adhered to said matrix.

According to other embodiments of the present invention, there is provided a dressing of the invention which optionally and preferably comprises: (i) a resorbable gelatin matrix; (ii) a transglutaminase; wherein the transglutaminase is incorporated within said gelatin matrix.

In various embodiments, the transglutaminase layer can be configured in any of a variety of shapes and patterns. For example, and without limitation, the transglutaminase layer can be configured as an array of spots comprising transglutaminase, or as a single spot comprising transglutaminase. Alternatively, the transglutaminase layer can be configured as a plurality of lines comprising transglutaminase.

Each layer of the hemostatic dressings can also optionally contain one or more suitable fillers, binding agents and/or solubilizing agents. In addition, each of the hemostatic dressings can also optionally further comprise a release layer which contains a release agent and/or a backing material.

According to preferred embodiments, each layer of the hemostatic dressings may optionally contain one or more suitable fillers, such as sucrose. Each layer of the hemostatic dressings can also optionally contain one or more suitable binding agents, such as sucrose. Each of the hemostatic dressings can also optionally further comprise a release layer which contains a release agent. An exemplary release agent is sucrose. Each layer of the hemostatic dressings can also optionally contain one or more suitable solubilizing agents, such as sucrose.

Each layer of the hemostatic dressings can also optionally contain one or more suitable foaming agents, such as a mixture of citric acid and sodium bicarbonate.

According to some demonstrative embodiments, the gelatin layer described hereinabove may optionally be foamed, for example, by mixing the gelatin solution with pressurized air and/or other gas prior to drying. In some embodiments, the gelatin foam may be in a density range of 5 to 100 mg/cm$^3$ and preferably in the range of 10 to 50 mg/cm$^3$.

Each of the hemostatic dressings can also further comprise a backing material on the side of the dressing opposite the wound-facing side when the dressing is in use. The backing material can be affixed with a physiologically-acceptable adhesive or can be self-adhering (e.g. by having a surface static charge or mechanical attachment). The backing material can be a resorbable material or a non-resorbable material, such as a silicone patch or plastic patch, and/or a device such as a vascular catheter and/or other type of medical device which may optionally be inserted to the body.

Patch Reinforcement Methods

Integration of reinforcing back layer enhances the mechanical strength of the dressing to provide optimal force distribution across the dressing for procedures where the dressing is applied to heavy and/or actively bleeding sites. The backing also reduces the tackiness of the back of the dressing such that the dressing does not stick to hands of the surgeon.

In some demonstrative embodiments, the backing layer may include one or more suitable materials, capable, for example, of increasing the hemostatic and/or fluid control capacity upon addition to a basic gelatin-TG mixture. According to some embodiments, increasing the hemostatic and/or fluid control capacity may be achieved via slowing the fluid and allowing the gelatin-TG more time to cross-link and block fluid leakage Optionally, the dressing is reinforced by a backing comprised of gelatin.

Optionally, the gelatin backing is comprised of a non-crosslinked gelatin layer wherein the gelatin layer is formed from a lyophilized layer of gelatin solution where the gelatin solution is at an initial concentration of 1-25% w/w and preferably 5-15%.

In an alternative embodiment, the gelatin backing is comprised of a crosslinked gelatin layer wherein the gelatin layer is formed by chemical crosslinking, radiation crosslinking, or physical crosslinking.

In a preferred embodiment, the crosslinking is performed using an aldehyded sugar, by a method analogous to the crosslinking method described for collagen in U.S. Pat. No. 4,971,954, which is hereby incorporated by reference as if set forth herein to the extent necessary to provide enablement to this exemplary crosslinking embodiment of the present invention and as a non-limiting example of such a crosslinking method.

In another preferred embodiment, the crosslinking is performed using dry heat crosslinking wherein the gelatin layer is heated with dry heat under a vacuum.

In an alternative optional embodiment, the dressing backing is comprised of a resorbable hemostatic material such as cellulose or oxidized cellulose.

Any of a variety of resorbable materials known to those skilled in the art can be optionally employed in the present invention. For example, the resorbable material can be a proteinaceous substance, such as fibrin, keratin, collagen and/or gelatin, or a carbohydrate substances, such as alginates, chitin, cellulose, proteoglycans (e.g. poly-N-acetyl glucosamine), glycolic acid polymers, lactic acid polymers, or glycolic acid/lactic acid co-polymers. For example, the resorbable material can be a carbohydrate substance. Illustrative examples of resorbable materials are sold under the tradenames VICRYL™ and DEXON™.

Any of a variety of non-resorbable materials known to those skilled in the art can be optionally employed in the present invention. Non-limiting examples of non-resorbable materials include silicone, latex, polyurethane, polypropylene, polyethylene, silastic, polyethylene tecephtalate (PET), dacron, knitted dacron, velour dacron, polyglacin, nylon, polyvinyl chloride silastic elastomer, silicone rubber, PMMA [poly-(methyl methacrylate), polyofefin, cellulose, poly vinyl]alcohol (PVA), poly(hydroxyethyl Methacrylate (PHEMA), poly(glycolic acid), poly(acrylonitrile) (PAN), fluoroethylene-cohexa-fluoropropylene (FEP), teflon (PTFE), Co—Cr alloys, copolymers thereof and mixtures thereof. These backings can be porous or solid.

In an optional embodiment, a pattern is etched, engraved, laser cut, or otherwise created on the backing so as to increase the surface area of the interface between the backing and the dressing. This can have the effect of partially or fully binding the dressing matrix to the backing. Example 23 describes an example of an etched pattern on a silicone backing being used to increase its adherence to a gelatin dressing matrix.

Assembly of Hemostatic or Sealing Dressing

According to some embodiments of the present invention, the transglutaminase layer can be applied to the first gelatin layer such that it is noncoextensive with the first gelatin layer and/or will be noncoextensive with the second gelatin layer upon application of the second gelatin layer. For example, the transglutaminase layer can occupy about 5% to about 95% of the surface area of the first gelatin layer and/or about 5% to about 95% of the surface area of the second gelatin layer. The transglutaminase can be applied to the gelatin layer in a single spot or as a series of spots on the gelatin layer such that the total surface area of the transglutaminase spots occupies about 5% to about 95% of the surface area of the first gelatin layer and/or about 5% to about 95% of the surface area of the second gelatin layer.

Such a spot or spots of transglutaminase can have any geometric shape, e.g., filled or unfilled circles, rectangles, triangles, lines, amorphous shapes, or combinations thereof. Such spots can be applied to the first gelatin layer in an ordered or random pattern. A plurality of spots can form any of a variety of shapes and patterns, such as an array, a grid, a series of concentric spots (e.g., concentric circles or squares), an overlapping series of spots (e.g., overlapping circles), spokes emanating from an axis, or any other configuration, provided that the total surface area of the transglutaminase is about 5% to about 95% of the surface area of the first gelatin layer and/or about 5% to about 95% of the surface area of the second gelatin layer. In general, a large number of small spots is preferred over a small number of large spots. For example, a 20.times.20 array of spots generally is preferable over a 10.times.10 array of spots occupying the same total surface area. However, the spots can be of any size provided that the total surface area of the transglutaminase is about 5% to about 95% of the surface area of the first gelatin layer and/or about 5% to about 95% of the surface area of the second gelatin layer. For example, depending upon the overall size of the dressing, the spots can be, without limitation, at least about 0.01, 0.1, 0.5, 1, 2, 3, 4, 5, 6, 7, 8, 9, 10 mm or more in diameter, width, or length. In one embodiment, for example, 4 circular spots having a diameter of 2-3 mm each can occupy a square centimeter of a dressing. A variety of other configurations are within the scope of the invention and can readily be utilized by those skilled in the art.

The dressing can optionally be prepared as any of a variety of sizes and shapes. Typically, the dressings are of a size and shape that can readily be handled by those skilled in the art, typically less than 12" in length along any side, e.g., 1"×1", 1"×2", 4"×4", etc. The moisture level of the dressing typically is less than 8% (e.g., less than 7, 6, 5, 4, 3, 2, or 1%).

Generally, the various layers of the hemostatic dressing can be affixed to one another by any means known and available to those skilled in the art. For example, optionally and preferably the gelatin layer(s) and/or the transglutaminase layer(s) is (are) applied as a series of quick-frozen aqueous solution layers and subsequently lyophilized or freeze-dried, e.g., after application of each layer, and upon assembly of the entire dressing. The layers can be applied by any of a variety of techniques, including spraying, pipetting (e.g., with a multi-channel pipettor), sprinkling, using a mask, electrostatic deposition, using a microsyringe array system, or dispensing using a dispensing manifold that contains ports for producing a high density array.

In certain embodiments of the present invention, when the dressings are prepared using a mold, a release agent, such as sucrose, is applied to the mold before the first layer of the dressing is applied. In such embodiments, the hemostatic dressing further comprises a release layer, which contains said release agent.

Alternatively, a physiologically-acceptable adhesive can be applied to the resorbable material and/or the backing material (when present) and the gelatin layer(s) and/or the transglutaminase layer(s) subsequently affixed thereto.

In one embodiment of the dressing, the physiologically-acceptable adhesive has a shear strength and/or structure such that the resorbable material and/or backing material can be separated from the gelatin layer after application of the dressing to wounded tissue. In another embodiment, the physiologically-acceptable adhesive has a shear strength such that the resorbable material and/or backing material cannot be separated from the gelatin layer after application of the dressing to wounded tissue.

The concentration of gelatin per area of the wound depends upon a number of factors, including but not limited to the final construction of the bandage, materials employed and so forth.

According to other embodiments of the present invention, there are provided methods for preparing a hemostatic dressing by optionally and preferably providing a first layer of gelatin, applying a layer of transglutaminase to the first layer of gelatin, and applying a second layer of gelatin to the layer of transglutaminase, wherein the layer of transglutaminase is noncoextensive with the first gelatin layer and/or noncoextensive with the second gelatin layer.

Similarly, other embodiments of the invention include a method for preparing a hemostatic dressing by providing a resorbable or nonresorbable backing layer having attached thereto a first layer of gelatin; applying a layer of transglutaminase to said first layer of gelatin on a side of the gelatin layer that is opposite of the side to which the resorbable or nonresorbable backing layer is attached; and applying a second layer of gelatin to the layer of transglutaminase, wherein the layer of transglutaminase is noncoextensive with the first gelatin layer and/or noncoextensive with the second gelatin layer.

In some demonstrative embodiments, the dressings and/or patches may be prepared by various methods, including, for example, "sandwich" patch with cross-linked backing, wherein the patch may include a thin layer of foamed gelatin, an enzyme powder and at least one other layer of foamed gelatin with or without spraying on top. The enzyme may optionally be any type of cross-linking enzyme, capable of cross-linking gelatin, but preferably comprises a transglutaminase.

Non-limiting examples of other embodiments of sandwich dressing configurations may optionally include the following. Optionally, the sandwich features a foamed heat crosslinked backing layer, with powder enzyme integrated into the backing, followed by a layer of foamed lyophilized gelatin and then by a layer of sprayed enzyme. The term "foamed" is used herein to relate to foamed gelatin.

Alternatively, the sandwich may optionally feature a foamed heat crosslinked backing layer, again with powder enzyme integrated into the backing, followed by a layer of foamed lyophilized gelatin, but in this non-limiting illustrative embodiment, the next layer comprises powder enzyme, followed by a layer of foamed lyophilized gelatin and followed by a layer of sprayed enzyme.

Alternatively, the sandwich may optionally feature a backing layer of any type (for example, optionally one of the previously described backing layers comprising polyurethane, silicone, or indeed any of the previously described medical plastics and/or rubber materials), followed by a layer of foamed lyophilized gelatin, followed by a layer of enzyme in carrier (e.g. HPMC or any other cellulosic or other polymer material as previously described), followed by a layer of foamed lyophilized gelatin and followed by a layer of sprayed enzyme.

Alternatively, the sandwich may optionally feature a foamed heat crosslinked backing layer, followed by a layer of powder enzyme integrated into the backing, followed by a layer of foamed lyophilized gelatin, followed by a layer of carrier-based enzyme layer (optionally with any polymer carrier as described herein), followed by a layer of foamed lyophilized gelatin and followed by a layer of sprayed enzyme.

Methods of Producing Gelatin Matrix

In some embodiments of the hemostatic and sealing dressing described above, the gelatin layer or gelatin matrix is comprised of lyophilized foamed gelatin solution (also referred to herein as "gelatin foam" or simply as "foam"). Prior to foaming, the concentration of the gelatin solution is optionally between 0.1% and 30% w/w and is preferably between 5% and 15% w/w.

The gelatin foam may optionally be in the density range of 5 to 100 mg/cm$^3$ preferably in the range of 10 to 50 mg/cm$^3$ and most preferably in the range of 20 to 40 mg/cm$^3$.

In some demonstrative embodiments, the gelatin foam can optionally be produced using, for example, a batch mixer process. According to some embodiments, the gelatin solution may be intensively mixed in a stand mixer, for example, of the type produced by Bosch™, Kenwood™, and KitchenAid™, at speeds ranging between 100 and 10,000 RPM and preferably at speeds ranging between 1000 RPM to 6000 RPM, or 2000 to 4000 RPM. According to some embodiments, the speed is preferably adjusted according to the viscosity and other properties of the gelatin solution, so as to induce the production of foam (bubbles) but without destroying the foam structure. According to some embodiments, after mixing, resulting foam may be filled in trays and lyophilized.

In some demonstrative embodiments, the gelatin foam can optionally be produced using, for example, a continuous mixing process. According to these embodiments, the gelatin solution and pressurized air may be simultaneously streamed together through a spherical static mixer to form a gelatin foam directly into trays, which may then be lyophilized. According to some embodiments, the air pressure and/or mixing speed may preferably be adjusted according to the viscosity and other properties of the gelatin solution, so as to induce the production of foam (bubbles) but without destroying the foam structure.

In some demonstrative embodiments, the gelatin foam can optionally be produced using, for example, chemical foaming. According to these embodiments, formation of the gelatin foam may be achieved by an addition of a foaming agent.

According to some embodiments, the foaming agent may include any surfactant which is capable of facilitating the formation of a foam and/or of enhancing the colloidal stability of the foam, for example, by inhibiting the coalescence of bubbles. For example, calcium bicarbonate may be added to acidified matrix, e.g., to cause formation of gaseous carbon dioxide in gelatin solution, creating foam.

In some demonstrative embodiments, the gelatin foam can optionally be produced using, for example, Venturi foaming. According to these embodiments, —the gelatin solution may be introduced into punctured tube. The gelatin solution may flow through the tube at a high velocity, e.g., to cause negative air pressure at the puncture site. According to some embodiments, this may lead to air suction into the gelatin stream and subsequent foaming of the gelatin inside the tube (foaming enhancement can be achieved by addition of static mixing elements).

In some demonstrative embodiments, various shapes and/or sizes of foamed gelatin may be used in the preparation of a patch in accordance with some demonstrative embodiments described herein, including, for example, small pieces of foamed gelatin, gelatin in a flowing or flowable form, particulate gelatin, and/or ground gelatin pad soaked with enzyme, for example and without limitation for voids such as cavity shaped wounds.

In some demonstrative embodiments of the herein invention, discrete pieces, particles, parts, segments or granules of non crosslinked protein matrix with embedded enzyme are applied to a wound site such that they join to form a single crosslinked matrix on the wound site, for example as described for voids.

These embodiments may optionally be used for treating cavity wounds such that the matrix pieces can be fit into an irregular cavity to effect hemostasis or otherwise treat the irregular cavity wound, where a full dressing might not be able to reach all wound site surfaces.

In an optional embodiment, the protein (gelatin) matrix pieces are less than 10 cm in diameter.

Preferably, the pieces are less than 1 cm in diameter.

Most preferably, the pieces are less than 5 mm in diameter.

In an optional embodiment, the protein matrix is a porous matrix in the density range of 5 to 100 mg/cm3 and preferably in the range of 10 to 50 mg/cm3.

An example of using enzyme embedded protein matrix pieces that join to form a single crosslinked matrix to treat a simulated wound is described in Example 15.

Various shapes and/or sizes of foamed gelatin may be used in the preparation of a dressing or wound treatment composition in accordance with some demonstrative embodiments described herein.

Enzyme Incorporation Methods

In some embodiments of the hemostatic and sealing dressing described above, the transglutaminase ("the enzyme") may be incorporated, integrated, or embedded into a gelatin matrix such that (without wishing to be limited by a closed list):

Enzyme activity may be preserved throughout process

Enzyme may be equally distributed across the gelatin matrix surface

Enzyme may be embedded into the depth of the gelatin matrix (gradient or equal distribution)

Such incorporation, integration or embedding is also referred to herein as "the enzyme incorporation".

In some demonstrative embodiments, the enzyme incorporation into the gelatin matrix may be accomplished using pre-mixed enzyme incorporation. According to these embodiments, the gelatin solution may be mixed with pressurized air, e.g., to form a foam in either the batch of continuous process described above.

In some embodiments, the enzyme may be simultaneously streamed into the solution flow. With batch foaming, the enzyme may be added to gelatin solution prior to or during mixing. According to some embodiments, with continuous foaming, the enzyme may be added to the gelatin solution inline as the solution enters the static mixer. After foam containing the gelatin and the enzyme is formed, it may be cooled to slow or prevent crosslinking and then lyophilized such that majority of crosslinking only occurs when lyophilized foam comes into contact with physiological fluid upon application to a wound.

In some demonstrative embodiments, the enzyme incorporation into the gelatin matrix may be accomplished using post-lyophilization enzyme solution incorporation. According to these embodiments, the gelatin matrix may formed and lyophilized in dry foam.

According to some embodiments, the Enzyme solution may be incorporated into the matrix by spraying of the enzyme solution onto dry gelatin matrix surface, for example, where the enzyme may be dissolved in solvent or water/solvent mixture prior to spraying.

According to some embodiments, the enzyme solution may be incorporated into the matrix using Injection of the enzyme solution into the gelatin matrix, for example, through needles or matrix of needles.

According to some embodiments, the enzyme solution may be incorporated into the matrix using submersing of dry gelatin matrix into enzyme-containing solvent mixture, for example, EtOH/water, Acetonitrile/water, Acetonitrile/water/EtOh, and the like.

According to some embodiments, the enzyme solution may be incorporated into the matrix by applying an enzyme-containing solvent mixture onto the dry gelatin matrix.

Other examples of volatile solvents applicable for this purpose can additionally be selected from the group consisting of ethyl acetate, benzene, methylene chloride, acetone, chloroform, volatile liquid silicones (hexamethyldisiloxane (HMDS), octamethylcyclotetrasiloxane, decamethylcyclopentasiloxane, octamethyltrisiloxanes), volatile alkanes (n-hexane, isooctane, octane, neopentane), volatile fluorocarbons (pentafluoropropane, perfluoroheptane, perfluoromethylcyclohexane), alcohols (including but not limited to one or more of 1-propanol, 2-propanol, ethanol) and mixtures thereof.

According to some demonstrative embodiments, after the enzyme solution is applied into and/or onto gelatin matrix, the solution may be evaporated, for example, by air drying, vacuum drying, heat drying, or other method.

According to some embodiments, the enzyme solution may be incorporated into the matrix using post-lyophilization enzyme powder incorporation. According to these embodiments, the gelatin matrix may be formed and lyophilized in dry foam.

In some demonstrative embodiments, the enzyme may then be incorporated into the matrix using enzyme powder embedding into dry gelatin matrix by mechanical methods, for example, by brushing the enzyme powder over surface and/or spreading enzyme powder using a needle roller.

According to other demonstrative embodiments, the enzyme may be incorporated into the matrix using perforation and/or puncture of the gelatin matrix with mechanical needle roller prior to enzyme powder application.

According to yet other demonstrative embodiments, the enzyme may be incorporated into the matrix using pressurized air supported enzyme powder application, for example, using a method similar to sand blasting.

Optionally, after dry enzyme powder application, the powder can be sealed inside the gelatin matrix, for example, by spraying the surface of the matrix with an organic solvent/water mixture and then drying the matrix.

According to some demonstrative embodiments, two or more methods may be combined to produce enzyme integration, for example, as described hereinabove.

Enzyme Depth in Protein Matrix

In an optional but preferred embodiment of the herein invention, the enzyme is embedded into the protein matrix such that enzyme is present at a depth of at least 0.5 mm from the surface of the matrix, preferably at least 1 mm and optionally up to 20 mm in depth.

Prior art describes wound dressings comprising a tissue adhesive material on the surface of a biomaterial or protein biomaterial matrix. Examples of this are described in PCT applications WO/2011/079336A1 and WO/2010/145817. However, these solutions have significant drawbacks in that the tissue adhesive mechanism on the surface of the protein matrix is not inherently integrated into the matrix itself. Thus, additional efforts must be made to fix the tissue adhesive layer to the matrix. Furthermore, since the matrix itself does not participate in the tissue adhesive or wound closure mechanism, it can separate from the tissue adhesive layer once the dressing is applied to a tissue site or wound site.

There is significant benefit of utilizing an adhesive mechanism based on crosslinking of the protein matrix itself, as described herein, since this approach ensures that the protein matrix itself will be directly involved in the binding of the patch, device or wound dressing onto a tissue site or wound site and will not detach from the adhered top layer of the composition.

Furthermore, it is beneficial to have crosslinking enzyme present beyond the surface of the matrix to enable crosslinking of the protein matrix beyond just the surface layer of the matrix. While the surface layer can adhere to a wound or tissue site, the crosslinked surface layer of matrix alone will frequently be insufficient to close wounds or fixate the dressing to a tissue site. When enzyme is present beyond the surface of the dressing, at depths of 0.5 mm and beyond, the amount of the protein matrix being incorporated into the crosslinking adhesive reaction is greater and thus the wound closure barrier or device fixation layer can be thicker and more robust. Furthermore, the inclusion of enzyme into the depths of the protein matrix reduces the likelihood of parts of the matrix remaining uncrosslinked after application to a tissue site and becoming detached from the parts of the matrix that adhere to the tissue site.

Examples provided below describe wound dressings wherein enzyme is present up to different depths of the matrix. In all examples except for Examples 8 and 12, embedded enzyme is present from the surface of the matrix down through the maximum depth listed in the below table. In Examples 8 and 12, embedded enzyme was present in a layer underneath a layer of protein matrix with no enzyme. Maximum enzyme depth was measured using a digital caliper to measure the depth to which the blue colored enzyme solution penetrated the porous protein matrix. In all cases, the approximate matrix thickness was 15 mm.

| Example # | Maximum depth of enzyme from matrix surface |
|---|---|
| 1. | 0.5 mm |
| 2. | 7 mm |
| 3. | 0.5 mm |
| 4. | 4 mm |
| 5. | 15 mm |
| 6. | 10 mm |
| 7. | 3 mm |
| 8. | 7 mm |
| 9. | 0.5 mm |
| 10. | 3 mm |
| 11. | 3.5 mm |
| 12. | 7 mm |
| 13. | 8 mm |
| 14. | 3 mm |
| 15. | 10 mm |
| 16. | 0.5 mm |
| 17. | 3.5 mm |
| 18. | 3.5 mm |
| 19. | 0.5 mm |
| 20. | 8 mm |
| 21. | 8 mm |
| 22. | 3 mm |

In an optional embodiment, enzyme is present in the protein matrix at a depth of 0.5 to 50 mm.

Preferably, enzyme is present in protein matrix at depth of 0.5 to 10 mm.

More preferably, enzyme is present in protein matrix at depth of 0.5 to 5 mm.

In an optional embodiment, enzyme is present in the protein matrix at a depth of from 1% to 100% of the total thickness of the matrix.

In an optional embodiment, the enzyme is penetrated to a protein matrix depth of at least 0.5 mm using one or more of the enzyme embedding techniques listed above.

In another optional embodiment, the enzyme is deposited and then covered by a crosslinkable protein matrix layer such that the effective depth of the enzyme is at least 0.5 mm from the top surface of the crosslinkable protein matrix.

Embedding of Encapsulated Enzyme

In some demonstrative embodiments, the enzyme described herein may be an encapsulated enzyme.

Without wishing to be limited by a closed list, there are several benefits of encapsulating the enzyme for use with at least some embodiments of the present invention:

1. Encapsulation of an enzyme can increase the stability of the enzyme by protecting it, allowing the enzyme to be embedded in a protein matrix without being potentially damaged by the embedding process.

2. Enzyme encapsulation can shield the enzyme activity from surrounding crosslinkable substrate, thus allowing the enzyme to be embedded in the protein matrix without reacting fully with the crosslinkable matrix. Preferably, the encapsulating material is soluble or partially soluble by body fluid or saline such that the encapsulation is dissolved when it is applied to a wound site and the enzyme can then react with the protein matrix.

According to some embodiments, the encapsulated enzyme may be produced and/or incorporated into the patch described herein using various methods, including, for example, embedded enzyme spraying, dripping, coacervation of oppositely charged polymers with embedded enzyme, PLGA, Microspheres, Spray drying, Burst release and the like.

According to some demonstrative embodiments, the enzyme can be encapsulated using any method known in the art, including, for example, physical methods such as pan coating, air-suspension coating, centrifugal extrusion (co-extrusion), vibrational nozzle and spray drying, physicochemical methods such as ionotropic gelation or coaceravation, and chemical methods such as interfacial polycondensation, interfacial cross-linking, in situ polymerization and matrix polymerization.

Enzymes were demonstrated to retain their activity after being encapsulated using various techniques. For example, encapsulation of lipase in k-carrageenan using co-extrusion (Raman K., Journal of Molecular Catalysis B:Enzymatic, 58: 78-83)

In another embodiment, the enzyme may be encapsulated in liposomes.

In another embodiment, enzyme may be microencapsulated in gelatin microcapsules in a technique that has been previously documented (Burgess D. J., International Journal of Pharmaceutics, 27: 61-70) The microcapsules may be integrated into the matrix and when heated by blood or body temperature may melt and the enzyme powder trapped within may be reconstituted.

According to some embodiments, the encapsulated enzyme may be in a solid form or a liquid form.

In some demonstrative embodiments, the materials used for coating the enzyme may be polymers (polyethylene glycol, polyvinyl alcohol, cellulose ethers, polylactic acid, polyglutaric acid, PLGA etc.) or proteins (gelatin, collagen, fibrinogen, albumin etc.).

Sterilization of Enzyme-Embedded Protein Matrix

In some demonstrative embodiments, the matrices may be sterilized, using, for example, radiation sterilization and preferably electron beam ("E-beam") sterilization.

Preferably, E-beam sterilization of the matrices or dressings is performed by exposing the dressing to a dose range in the range of 10-50 kGy, and preferably 20-40 kGy.

Optionally, a radioprotectant is included to minimize changes effected by radiation sterilization. A radioprotectant can include any material with the ability to bind free radicals and can be chosen from any of the materials listed in table 4, below.

Adhesive Hemostatic & Tissue Sealing Device

Another exemplary embodiment of the present invention is directed to a hemostatic and tissue sealing device, e.g., for hemostasis in a surgical environment of a briskly bleeding patient or for sealing of other tissue in a patient, which comprises: (i) a porous resorbable or non-resorbable matrix; (ii) gelatin in powder, particle, or other solid form, and (iii) transglutaminase in powder, particle or other solid form; wherein the gelatin and transglutaminase are incorporated within said matrix.

Another embodiment of the present invention is directed to a hemostatic device, e.g., for hemostasis in a surgical environment of a briskly bleeding patient, which comprises: (i) a porous resorbable or non-resorbable matrix; (ii) gelatin; (iii) a transglutaminase; wherein the gelatin and transglutaminase are adhered to said matrix.

Another exemplary embodiment of the present invention is directed to a hemostatic device, e.g., for hemostasis in a surgical environment of a briskly bleeding patient, which comprises: (i) a porous resorbable gelatin matrix; (ii) transglutaminase in powder, particle or other solid form; wherein the transglutaminase is incorporated within said gelatin matrix.

Another exemplary embodiment of the present invention is directed to a hemostatic device, e.g., for hemostasis in a surgical environment of a briskly bleeding patient, which comprises: (i) a porous resorbable gelatin matrix; (ii) transglutaminase in powder, particle or other solid form; wherein the transglutaminase is incorporated within said gelatin matrix; (iii) mechanical backing or reinforcement.

Adhesive Hemostatic/Sealing Device Used in Conjunction with Medical Device

According to some embodiments of the present invention, a freeze drying and/or lyophilizing technique may optionally be applied to adhere or fix the sealant composition according to the present invention onto the surface of any catheters, trocars or implants, or indeed any other such medical device. This may optionally facilitate hemostasis at the penetration wound and its closure, which may optionally be useful for arterial catheters/devices for example. Hemostasis after arterial procedure is critical for patients who have been treated with anti-coagulation medication and who are more prone to bleeding complications. The hemostatic composition of the present invention is independent of blood clotting and so provides additional assistance to prevent excess bleeding.

Hemostatic Device Used for Implantable Medical Device Fixation

In another embodiment of the present invention, the hemostatic and sealing device or dressing is integrated with an implantable medical device, such as a surgical mesh such that the mesh can be adhered to a tissue surface. As a non-limiting example of such an embodiment, the device or dressing is optionally integrated with the mesh, which is then further coated with a gelatin layer as an adhesive coating. Such an adhesive coating integrated mesh could be useful for applications such as hernia mesh fixation without stapling or suturing procedure where mesh can be adhered to abdominal wall.

Such an adhesive coating to mesh may also optionally be used together with one or more of staples, tacks, or sutures to supplement mesh adhesion.

Additionally, implanting a surgical mesh into a gelatin-transglutaminase matrix can provide short term camouflage of a non-degradable hernia mesh to reduce foreign body reaction towards the mesh.

In an embodiment, the surgical mesh is incorporated into a gelatin foam matrix and enzyme is incorporated either homogeneously throughout the matrix or concentrated more in the matrix close to the mesh surface.

In some embodiments of the surgical mesh embedded in the hemostatic dressing or device, a reinforcing backing layer is incorporated.

According to some embodiments, the surgical mesh may be located at any suitable position with relation to the reinforcement layer and/or the gelatin matrix, including, for example, between the reinforcement layer and the gelatin matrix, In the middle of the gelatin matrix and/or on top of the gelatin matrix.

According to some embodiments, the enzyme may be located at any suitable position with relation to the mesh and/or the gelatin matrix, including, for example In the middle and/or on top of the gelatin matrix and/or equally dispersed inside the gelatin matrix and/or covering the mesh, e.g., before it is embedded in the gelatin matrix.

In some embodiments of the present invention, a surgical mesh is coated with an adhesive gelatin-transglutaminase composition, such that the gelatin-transglutaminase composition is optionally implemented as an adhesive coating which may optionally be used for a surgical procedure, examples of which include but are not limited to inguinal, femoral, umbilical, incisional, and other types of ventral hernia repair. Alternatively, the coated mesh may optionally be used for large diaphragmatic hernia repair, for rectopexy (rectal prolapsed) mesh fixation, for reconstruction of a prolapsed vaginal vault, or for other pelvic floor mesh reinforcement operations (gynecology procedures).

The surgical mesh for use with these non-limiting embodiments of the present invention may optionally be a synthetic mesh, a biological mesh, or a combination synthetic-biological mesh.

Non-limiting examples of suitable surgical meshes are listed below:

TABLE 2

Synthetic Surgical Meshes

| Commercial Mesh Name | Material | Manufacturer |
|---|---|---|
| 1. VICRYL ™ Woven Mesh | Polyglactin 910 (Polyglycolic Acid) | Ethicon (Somerville, NJ) |
| 2. PROLENE ™ 3D Patch Polypropylene Mesh | Polypropylene | Ethicon |
| 3. PROLENE ™ Polypropylene Mesh | Polypropylene | Ethicon |
| 4. PROLENE ™ Polypropylene Hernia System | Polypropylene | Ethicon |
| 5. MERSILENE ™ Polyester Fiber Mesh | Polyethylene Terephthalate | Ethicon |
| 6. ULTRAPRO ™ Partially Absorbable Lightweight Mesh | Monocryl (Poliglecaprone 25) and Polypropylene | Ethicon |
| 7. ULTRAPRO ™ Plug | Monocryl (Poliglecaprone 25) and Polypropylene | Ethicon |
| 8. ULTRAPRO ™ Hernia System | Monocryl (Poliglecaprone 25) and Polypropylene | Ethicon |
| 9. PVP ™ Device | Oxidized Regenerated Cellulose (ORC) and Polypropylene | Ethicon |
| 10. PROCEED ™ Surgical Mesh | Oxidized regenerated cellulose (ORC) and Polypropylene | Ethicon |
| 11. Parietex ™ Composite (PCO) Mesh | Macroporous Polyester, with a Three Dimensional Weave Material with resorbable collagen film | Covidien (Mansfield, MA) |
| 12. Parietex ™ composite open skirt (PCO OS) mesh | Macroporous Polyester, with a three Dimensional Weave Material with resorbable collagen film | Covidien |
| 13. Parietex ™ Composite (PCO) Parastomal mesh | Macroporous Polyester, monofilament material | Covidien |
| 14. Parietex ™ Composite (PCO) Hiatal mesh | Macroporous Polyester, with a three Dimensional Weave Material with resorbable collagen film | Covidien |
| 15. Parietex ™ anatomical mesh | Macroporous Polyester, 2D weave with 3D weave | Covidien |
| 16. Parietex ™ Folding mesh | Macroporous Polyester | Covidien |
| 17. Parietex Easegrip ™ mesh | Polyester, with a combination of two and three Dimensional Weave Material | Covidien |
| 18. Parietex ™ lightweight monofilament mesh | Monofilament knit, macroporous polyester | Covidien |
| 19. Parietex ™ Flat sheet mesh | Polyester, with both two and three Dimensional Weave options | Covidien |
| 20. Surgipro ™ Flat Sheet mesh | Polypropylene | Covidien |
| 21. PERFIX ™ Light Plug | Monofilament Polypropylene | Davol (Bard) (Warwick, RI) |
| 22. PerFix ™ Plug | Monofilament Polypropylene | Davol (Bard) |
| 23. Kugel ™ Patch | Monofilament Polypropylene | Davol (Bard) |
| 24. 3DMax ™ Light Mesh | Monofilament Polypropylene | Davol (Bard) |
| 25. Bard ™ Soft Mesh | Large pore monofilament polypropylene | Davol (Bard) |
| 26. Bard ™ Mesh | Monofilament Polypropylene | Davol (Bard) |
| 27. Bard ™ Visilex ™ Mesh | Monofilament Polypropylene | Davol (Bard) |
| 28. Ventrio ™ Hernia Patch | Monofilament Polypropylene and polydioxanone, with Submicronic ePTFE side | Davol (Bard) |
| 29. Composix ™ L/P Mesh | Low profile polypropylene Bard Soft Mesh and sub-micronic ePTFE side | Davol (Bard) |
| 30. Composix ™ E/X | Polypropylene Bard Soft Mesh and sub-micronic ePTFE side | Davol (Bard) |
| 31. Composix ™ Kugel ™ Patch | Self-expanding polypropylene/ePTFE mesh | Davol (Bard) |

TABLE 2-continued

Synthetic Surgical Meshes

| Commercial Mesh Name | Material | Manufacturer |
|---|---|---|
| 32. Dulex ™ Mesh | Dual-sided ePTFE mesh | Davol (Bard) |
| 33. VENTRALEX ™ Hernia Patch | Self-expanding polypropylene and ePTFE | Davol (Bard) |
| 34. Sepramesh ™ IP Composite | Polypropylene mesh with a hydrogel safety coating | Davol (Bard) |
| 35. C-QUR ™ V-Patch | Polypropylene mesh with an all natural, pharmaceutical grade Atrium Omega 3 fatty acid | Atrium (Hudson, NH) |
| 36. C-QUR ™ Mesh | Polypropylene mesh with an all natural, pharmaceutical grade Omega 3 fatty acid | Atrium |
| 37. C-QUR Lite ™ Mesh | Polypropylene mesh with a thin, 30 day omega 3 fatty acid | Atrium |
| 38. C-QUR Edge ™ | Bioabsorbable Oil (O3FA) Coated mesh features a reinforced edge design | Atrium |
| 39. ProLoop ™ Mesh | Non-absorbable, lightweight, pre-formed, three-dimensional plug constructed of knitted rows of monofilament polypropylene with multiple protruding monofilament loops | Atrium |
| 40. ProLite ™ Mesh | Polypropylene Mesh | Atrium |
| 41. ProLite ™ Ultra ™ Mesh | Thin wall polypropylene mesh | Atrium |
| 42. BIO-A ™ Tissue Reinforcement | Polyglycolic acid:Trimethylene carbonate (PGA:TMC) fibers form a non-woven web with open, highly interconnected pores | Gore Medical (Flagstaff, AZ) |
| 43. DUALMESH ™ PLUS Biomaterial | Two-surface hernia repair material with antimicrobial technology | Gore |
| 44. DUALMESH ™ Biomaterial | ePTFE material that offers two-surface design intended for minimizing tissue attachment along another surface. | Gore |
| 45. MYCROMESH ™ Biomaterial | Microporous node and fibril structure with regularly spaced macropores. | Gore |
| 46. MYCROMESH ™ PLUS Biomaterial | Includes antimicrobial technology | Gore |
| 47. GORE-TEX ™ Soft Tissue Patch | Expanded polytetrafluoroethylene (ePTFE) | Gore |
| 48. BIO-A ™ Hernia Plug | Porous fibrous structure composed of synthetic copolymer | Gore |
| 49. INFINIT ™ Mesh | 100% monofilament PTFE, large pore knitted surgical mesh | Gore |

TABLE 3

Biological Surgical Meshes

| Commercial Mesh Name | Material | Manufacturer |
|---|---|---|
| 1. FLEXHD ™ Acellular Hydrated Dermis | Acellular human skin | Ethicon |
| 2. Permacol ™ Biologic Implant | Derived from porcine dermal collagen | Covidien |
| 3. XENMATRIX ™ Surgical Graft | Non-crosslinked collagen matrix | Davol (Bard) |
| 4. COLLAMEND ™ FM Implants | All-natural porcine collagen | Davol (Bard) |
| 5. AlloMax ™ Surgical Graft | All-natural biologic implant derived from human dermal collagen. | Davol (Bard) |
| 6. Biodesign ™ (Surgisis ™) Hernia Graft | Dry, acellular porcine small intestinal submucosa | Cook Biotech (Lafayette, IN) |
| 7. Biodesign ™ (Surgisis ™) Hiatal Hernia Graft | Dry, acellular porcine small intestinal submucosa | Cook Biotech |
| 8. Biodesign ™ (Surgisis ™) Inguinal Hernia Graft | Dry, acellular porcine small intestinal submucosa | Cook Biotech |
| 9. Biodesign ™ (Surgisis ™) Umbilical Hernia Graft | Dry, acellular porcine small intestinal submucosa | Cook Biotech |
| 10. Biodesign ™ (Surgisis ™) Abdominal Lock Graft | Dry, acellular porcine small intestinal submucosa | Cook Biotech |
| 11. Biodesign ™ (Surgisis ™) 8-Layer Tissue Graft | Dry, acellular porcine small intestinal submucosa | Cook Biotech |
| 12. Strattice ™ Reconstructive Tissue Matrix | Decellularized porcine skin | LifeCell - Genzyme Corp (Branchburg, NJ) |
| 13. AlloDerm ™ | Decellularized human cadaver skin | LifeCell |

Use of Device, Composition or Bandage

During use of the hemostatic dressing, device, or agent, the gelatin and the transglutaminase can be activated at the time the dressing, device, or particle mixture is applied to the wounded tissue by the endogenous fluids (e.g., blood, air, bile, intestinal fluid) of the patient escaping from the hemorrhaging or leaking wound. Alternatively, in situations where fluid loss from the wounded tissue is insufficient to provide adequate hydration of the protein layers, the gelatin and or the transglutaminase can be activated by a application of a physiologically-acceptable liquid (e.g., water, buffer, saline), optionally containing any necessary co-factors and/or enzymes, prior to or upon application of the hemostatic dressing, device, or agent to the wounded tissue.

Additives for Use with Above Dressing and Device Compositions

In an optional embodiment of any of the above devices and/or dressings, suitable compositional additives can be utilized for modification and/or improvement of the mechanical, stability, or handling properties of the device and/or dressing. According to some demonstrative embodiments, such additives may include buffers for protein stabilization, including, for example, Sodium Acetate, HEPES, Sodium Citrate; Plasticizers and/or flexibility enhancers, including, for example Glycerol, Polyethylene Glycol (PEG), Polyvinyl Alcohol (PVA), Tween; Foaming stabilizers, including, for example, Ionic surfactants (i.e. SDS), Hydroxyl Propyl Methyl Cellulose, Hyaluronic Acid, Glycine, Dextrin, and the like; Radioprotectants, as demonstrated, for example, in table 4 below and Antioxidants, as demonstrated, for example, in table 4 below.

TABLE 4

| Ingredient | Function |
| --- | --- |
| Ascorbate | Antioxidant |
| Benzyl alcohol | Preservative |
| Benzyl benzoate | Preservative |
| Butylated Hydroxyanisole (BHA) | Antioxidant |
| Chlorobutanol | Preservative |
| Cysteine | Antioxidant |
| Ethanol | Cosolvent |
| Glycerin | Humectant |
| Mannitol | Isotonicity Adjustor |
| Methyl paraben | Preservative |
| Niacinamide | Active |
| Phenol | Preservative |
| Propylene glycol | Cosolvent |
| Propyl gallate | Antioxidant |
| Propyl paraben | Preservative |
| Sodium benzoate | Buffer (pH 7.4) |
| Sodium bisulfate | Antioxidant |
| Sodium metabisulfite | Antioxidant |
| Sodium salicylate | Active |
| Sodium thiosulfate | Active |
| Tocopherol | Antioxidant |
| Trehalose | Isotonicity Adjustor |

Modified Enzyme

The enzyme according to at least some embodiments of the present invention may be modified in a way that will affect its activity, structure, or both structure and activity.

For example, site directed mutagenesis may result in an enzyme with reduced activity, increased activity, selective activity towards a subset of substrates, increased or decreased affinity towards a subset of substrates etc.

Chemical modification of mTG may be targeted against specific active amino acids. For example, amine groups of lysine side chains may be modified using reactions such as PEGylation, acetylation, succinylation, carbamoylation, reductive alkylation etc. Thiol groups of cysteine side chains my be modified with thiol specific reagents such as iodoacetamide, N-ethylmaleimide or activated PEG-maleimide. Carboxylic groups of glutamate and aspartate side chains may be modified by carbodiimides.

The above modification may also result in an increase or decrease in the surface charge of the enzyme which in turn may affect the activity, substrate preference, mobility and other functions of the modified enzyme.

The enzyme may also be coupled to another molecule, such as albumin, carboxymethylcellulose, dextran etc. This coupling may serve to control the activity, substrate preference, mobility and other functions of the enzyme.

Non-limiting examples of a modified enzyme used for crosslinking proteins is disclosed in published PCT Application No. WO 2011/077388, having at least one inventor in common with the present application and being owned in common with the present application, which is hereby incorporated by reference as if fully set forth herein.

EXAMPLES

Test Methods

Basic Burst Pressure Test

The test is done using a materials testing instrument, Instron 3343. A wet collagen sheet (10×10 cm; Nitta, porcine collagen casing) is rehydrated with approximately 5 ml saline solution (0.15M Sodium chloride, Sigma, batch #: 078K01272) at room temperature (RT) and punctured in the middle using a 14G needle. A dry Patch (size 2×2 cm) with the enzyme containing layer or part facing towards the collagen sheet is placed on the wet collagen sheet covering the puncture centrally. Pressure on the patch is applied using a 1 kg standard weight for 3 min. After removal of the 1 kg standard weight, the collagen sheet with the downwards facing attached patch is placed on a stand as graphically shown in FIG. 1. The burst pressure cell consists of a ring stand, which allows the collagen sheet to be fixated mechanically while allowing the patch covered area to levitate in the middle of the ring. A hollow cylinder (inner diameter of 36.5 mm) is placed on top of the collagen sheet baring stand and is fixated mechanically. The hollow cylinder is filled with water at RT. The hollow cylinder is sealed with an O-ring baring piston on top of the hollow cylinder. After placing the cell onto the Instron stage the piston is moved into the seal cylinder by the load cell baring stamp of the instrument, creating an increasing pressure on the collagen sheet with the puncture and the patch located beneath the collagen sheet. The maximum measured force relates to the burst pressure of the patch.

Advanced Burst Pressure Test

The test is done using a materials testing instrument, Instron 3343.

A round hole with diameter of 3 mm is punctured in the middle of a wet collagen sheet (10×10 cm; Nitta, porcine collagen casing). The punctured collagen sheet is submerged in a saline solution (0.15M Sodium chloride, Sigma, batch #: 078K01272) at 40° C. The saline level in the petri dish is approximately 15 mm. A dry gelatin patch (size 2×2 cm) is placed on top of the puncture and pressure is applied using a 1 kg standard weight for 3 min. After removal of the 1 kg standard weight, the collagen sheet with the downwards facing attached patch is placed on a stand as graphically shown in FIG. 1. The burst pressure cell consists of a ring stand, which allows the collagen sheet to be fixated mechanically while allowing the patch covered area to levitate in the middle of the ring. A hollow cylinder (inner diameter of 36.5 mm) is placed on top of the collagen sheet baring stand and is fixated mechanically. The hollow cylinder is filled with water at RT. The hollow cylinder is sealed with an O-ring baring piston on top of the hollow cylinder. After placing the cell onto the Instron stage the piston is moved into the seal cylinder by the load cell baring stamp of the instrument, creating an increasing pressure on the collagen sheet with the puncture and the patch located beneath the collagen sheet. The maximum measured force relates to the burst pressure of the patch.

Figure 2:
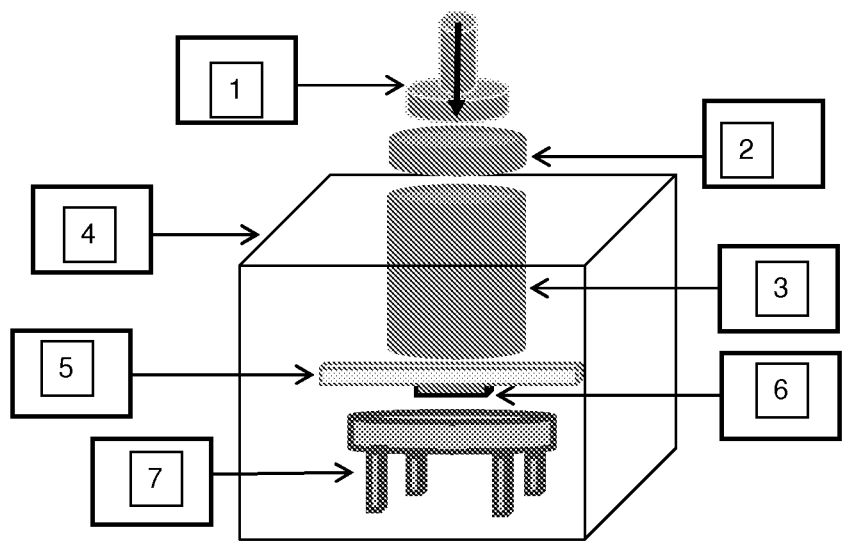
FIG. 2 shows a schematic block diagram of an exemplary Instron burst pressure testing system.
Figure 5:
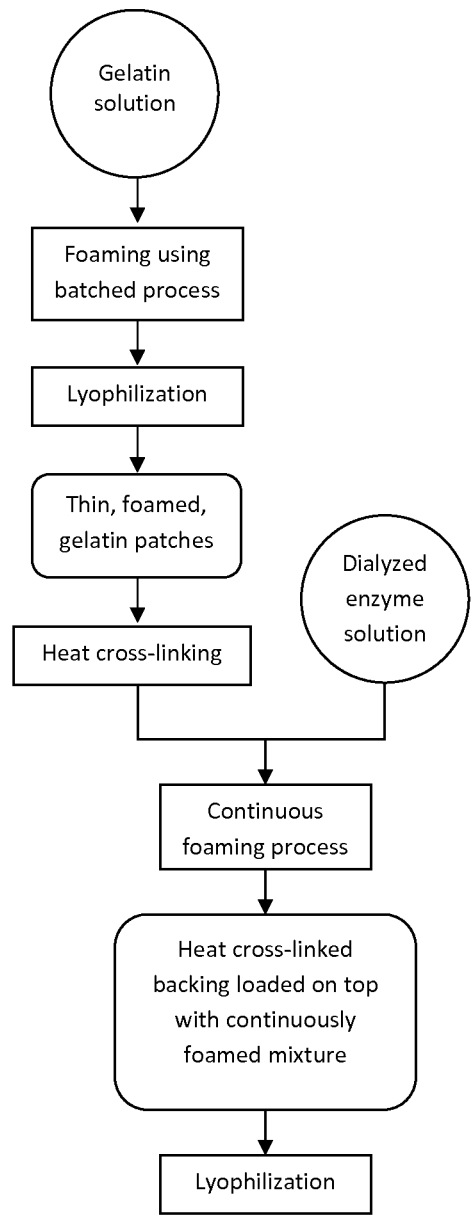
FIG. 5 shows the flowchart for example #6.

Reference is now made to FIG. 2 which demonstrates a schematic block diagram of an exemplary Instron burst pressure testing system, for example, as described hereinabove in accordance with some demonstrative embodiments.

According to some embodiments, the Instron burst pressure testing system may include an Instron connector 1; a Piston 2; a Cylinder 3; a Perspex bath 4, used for example, for collecting leaking water; a Punctured collagen sheet 5; a Patch 6 and/or a Stand 7.

Figure 12:
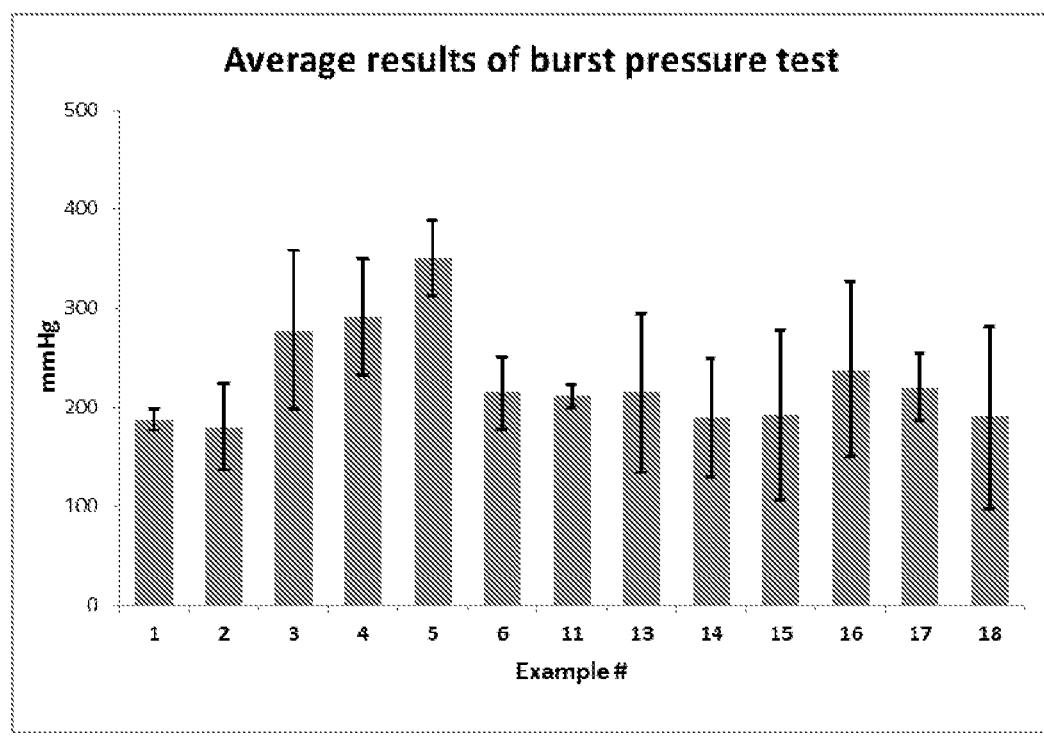
FIG. 12 is an illustrative graph showing the burst test results from Examples 1-18.

FIG. 12 is an illustrative graph showing the burst test results from Examples 1-18.

Foaming Processes

Batched Foaming Process

The gelatin solution is stabilized at 38° C. The gelatin is foamed using the mechanical mixer (Greatz, model #GR-3060A) for 2 minutes at speed #2 and 1.5 minutes at speed #5. Subsequently, the foamed gelatin is transferred into lyophilization trays (100 mm×100 mm).

Continuous Foaming Process

Air inlet, gelatin solution inlet and enzyme solution inlet are connected to a static mixer (Nordson EFD spiral mixers-24 mixing elements with a diameter of 12.7 mm each; housing length is 33.53 cm). The flow rates are 6.5 L/hr of gelatin solution, 1 L/min of air and 5 ml/min of enzyme solution. The gelatin solution temperature at the entrance into the mixer is approximately 30° C.

Materials, Solutions and Tools

Dialyzed Enzyme Solution

A 15% (w/V) enzyme solution was prepared by dissolving microbial TransGlutaminase (mTG) powder (Activa TG powder, Ajinomoto, batch #100727) in 0.1M Na—Ac (Sodium acetate trihydrate, Merck lot#A902812 014) and dialyzing twice against 0.1M Na—Ac (Sodium acetate trihydrate, Merck lot#A902812 014) it for 24 hours.

Lyophilized Enzyme Powder

2% (w/V) enzyme solution was prepared by dissolving raw mTG enzyme powder (Activa TG powder, Ajinomoto, batch #100727) in 0.01M Na—Ac (Sodium acetate trihydrate, Merck lot#A902812 014). MB solution was added to the enzyme solution in ratio of 3:100. The solution was filtrated trough a 200 micron filter and then lyophilized until dryness at 0.01 mbar and a temperature ramp from 0° C. to 20° C.

Methylene Blue Solution (MB)

The solution was prepared by dissolving methylene blue powder (Riedel-de Haen lot#23120) in 0.01M Na—Ac (Sodium acetate trihydrate, Merck lot#A902812 014).

Lyophilizer

Christ model Epsilon 2-60

Example 1

Burst Pressure Testing of Sprayed Patch

5% (w/V) gelatin (Gelita, lot #601089) was dissolved in 0.01M Na—Ac (Sodium acetate trihydrate, Merck lot#A902812 014) solution. The gelatin solution was foamed using the batched foaming process. The foam was loaded into 10×10×1.5 cm trays. The trays were lyophilized using the lyophilizer.

The dialyzed enzyme solution was mixed with ethanol (Frutarom, lot#9306482 No. 015) in ratio of 3:2. A MB solution was added to the mixture in ratio of 3:50 (MB: enzyme). The solution was sprayed on the lyophilized gelatin using a spray gun (Profxene, PR-103, Mfg SN 14200226). The sprayed patches were dried in the Christ lyophilizer at 0.01 mbar pressure and a temperature ramp from 0° C. to 20° C.

Example 2

Burst Pressure Testing of Patch with Enzyme Integrated During Batched Foaming

Two gelatin solutions were prepared: 8% (w/V) gelatin (Gelita, lot #601089) in 0.01M Na—Ac (Sodium acetate trihydrate, Merck lot#A902812 014) and 2.5% (w/V) gelatin (Gelita, lot #601089) in 0.01M Na—Ac (Sodium acetate trihydrate, Merck lot#A902812 014). The 8% gelatin solution was stabilized on 38° C. A thin layer of the non-foamed solution was loaded into each tray (about 10 ml for a 10×10 cm surface). The gelatin was cooled down to room temperature and kept for approximately 30 min. The 8% gelatin solution was foamed using the batched foaming process. About 60 ml of the foam was loaded onto the prior gelatin layer 10×10×1.5 cm trays. Subsequently, the trays were placed in the freezer for 25 minutes.

The 2.5% gelatin solution was foamed using the mechanical mixer for 30 sec at speed #5. A dialyzed enzyme solution was mixed with the MB solution at RT and cooled to 6° C. The mixture was added to the gelatin foam in ratio of 3:200. The resulting mixture was foamed for another 2 minutes at speed #5. 60 ml of the final foamed mixture was poured onto the frozen gelatin/gelatin foam layers of each lyophilization tray. The trays were lyophilized using Christ lyophilizer until dryness at 0.01 mbar pressure and a temperature ramp from 0° C. to 20° C.

Example 3

Burst Pressure Testing of Patch with Enzyme Integrated by Spraying and Chemically Cross-Linked Backing A solution of 9% (w/V) gelatin (Gelita, lot #601089) in 0.01M Na—Ac (Sodium acetate trihydrate, Merck lot#A902812 014) buffer was heated to 38° C. and foamed using the batched foaming process. A thin layer of the foam was loaded into the trays (about 4 mm thickness). The foam was lyophilized until dryness. Subsequently, the gelatin pads were cross-linked chemically.

The cross-linking solution consists of 70% ethanol (Frutarom, lot#9306482 No. 015) and 0.05% (w/V) DL-glyceraldehyde (Biosynth chemistry and biology, lot#121006/9) in purified water. Each pad was placed in a container, covered with a sufficient amount of cross-linking solution and sealed. The containers were placed in the incubator for 72 hours at 37° C.

Subsequently, the pads were washed with purified water, extensively.

A solution of 9% (w/V) gelatin (Gelita, lot #601089) in 0.01M Na—Ac (Sodium acetate trihydrate, Merck lot#A902812 014) buffer was prepared and foamed under the same conditions as the cross-linked patch. The cross linked pads were placed in the lyophilization trays and covered with the prepared foam. The pads were lyophilized until dryness at 0.01 mbar pressure and a temperature ramp from 0° C. to 20° C.

An enzyme solution was prepared by mixing purified enzyme 300 u/ml (batch#27-27) with ethanol (Frutarom, lot#9306482 No. 015), in ratio of 3:2. A MB solution was added to the mixture in ratio of 3:50 (MB:enzyme solution).

Figure 7:
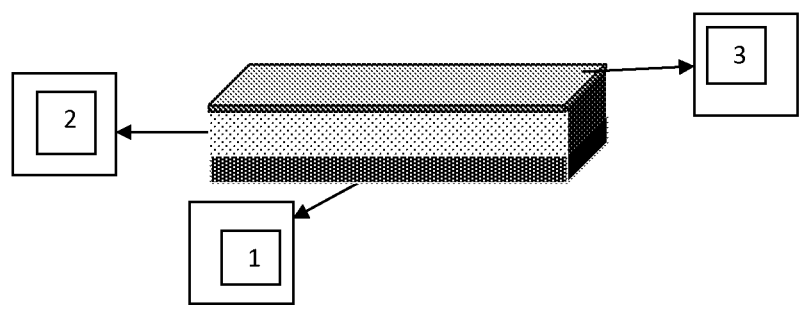
FIG. 7 shows an exemplary bandage as constructed for example #3.

The enzyme solution was sprayed equally onto the lyophilized pads. The sprayed patched were dried by lyophilization at 0.01 mbar pressure and a temperature ramp from 0° C. to 20° C. Reference is now made to FIG. 7, which shows an exemplary bandage as constructed for example#3, in accordance with some demonstrative embodiments.

According to some embodiments, the bandage of FIG. 7 may include a glyceraldehyde cross-linked foamed gelatin layer 1; a foamed gelatin 2, and a sprayed enzyme layer 3.

Example 4

Burst Pressure Testing of Patch with Dry Enzyme Powder Integrated into Punctured Patch with Cellulose Fibers Backing Oxidized cellulose fibers were added to a 9% (w/V) gelatin (Gelita, lot #601089) in 0.01M Na—Ac (Sodium acetate trihydrate, Merck lot#A902812 014) solution in ratio of 1:2. Approximately 10 ml of the slurry was poured to the lyophilization trays (10×10 cm). The trays were kept at RT for about 30 minutes until stabilization of the slurry. A 9% (w/V) gelatin (Gelita, lot #601089) in 0.01M Na—Ac (Sodium acetate trihydrate, Merck lot#A902812 014) solution was heated to 38° C. and foamed using the batched foaming process. The foam was transferred into the lyophilization trays covering of the stabilized gelatin/oxidized cellulose slurry. The loaded trays were lyophilized until dryness.

Subsequently, the dry pads were punctured from their non-cellulose containing side using a model made in 3D printer (Connex500™, Objet Geometry Ltd.). The model consists of a matrix of 1.2 mm diameter needles with 5 mm distance between them. The needles were of 3 different lengths-4 mm, 8 mm and 12 mm.

The punctured patch was covered with the raw enzyme powder and the incorporated into the foam matrix by gentle brushing.

The enzyme treated patch side was sprayed with 40% ethanol (Frutarom, lot#9306482 No. 015)/water solution in order to seal the pad surface avoiding an uncontrolled enzyme removal and lyophilized at 0.01 mbar pressure and a temperature ramp from 0° C. to 20° C.

Example 5

Burst Pressure Testing of Patch with Enzyme Integrated by Dipping the Patch in Enzyme Solution Approximately 10 ml of 9% (w/V) gelatin (Gelita, lot #601089) in 0.01M Na—Ac (Sodium acetate trihydrate, Merck lot#A902812 014) solution was poured into lyophilization trays (10×10 cm). The trays were kept in RT for about 30 minutes until the stabilization of the solution.

A foaming solution of 9% gelatin (Gelita, lot #601089) in 0.01M Na—Ac (Sodium acetate trihydrate, Merck lot#A902812 014) and 0.06M Na-ascorbate (Sigma, batch#038K0046) was prepared and heated to 38° C. The solution was foamed using the batched foaming. The foam was loaded into the trays on covering the non-foamed gelatin layer. The patch was lyophilized until dryness at 0.01 mbar pressure and a temperature ramp from 0° C. to 20° C.

An enzyme solution was prepared by mixing purified enzyme 750 u/ml (batch #27-37), ethanol (Frutarom, lot#9306482 No. 015) and acetonitrile (Sigma, lot#STBB1581K9) in ratio of 1:4:5. 25 ml of the solution were poured into lyophilization tray and the dry gelatin patch was submersed in the solution; non-foamed layer facing up. The patches were dried using the lyophilizer at 0.01 mbar pressure and a temperature ramp from 0° C. to 20° C.

Example 6

Burst Pressure Testing of Continuously Foamed Gelatin Patch with Enzyme Integrated During the Foaming Procedure with Heat Cross-Linked Gelatin Backing A 9% (w/V) gelatin (Gelita, lot #601089) in 0.01M Na—Ac (Sodium acetate trihydrate, Merck lot#A902812 014) solution was heated to 38° C. and foamed using the batched foaming. A 4 mm layer of the foam was loaded into the lyophilization trays. The foam was lyophilized until dryness at 0.01 mbar and a temperature ramp from 0° C. to 20° C. The dry patches were cross-linked by heat in vacuum (Nuve, EV 108, Mfg SN 03-0250) at 160° C. oven set temperature for 7 hours in vacuum of ~2 mbar (Ilmvac, MPC 201 TMfg SN 4ek6f56cx).

A 9% gelatin (Gelita, lot #601089) in 0.01M Na—Ac (Sodium acetate trihydrate, Merck lot#A902812 014) solution was prepared and foamed with dialyzed enzyme solution mixed with MB solution (ratio 2:1) using the continuous foaming process. The heat cross-linked pads were placed into lyophilization trays, wetted with water spray and covered with gelatin foam. The layered assembly was lyophilized until dryness at 0.01 mbar pressure and a temperature ramp from 0° C. to 20° C.

Example 7

Gelatin and Glycerol Patch with Hernia Reinforcement Mesh with Integrated Powder Enzyme and a Backing A solution of 9% (w/V) gelatin (Gelita, lot #601089) with 3% (w/V) glycerol (Frutarom, lot#26319005) in 0.01M Na—Ac (Sodium acetate trihydrate, Merck lot#A902812 014) buffer was heated to 38° C. 10 ml of the solution was loaded into each lyophilization tray and kept for 30 min at RT to stabilize the solution. The remaining gelatin solution was foamed using the batched foaming process. An approximately 5 mm layer of the foamed gelatin was poured into the trays covering the first non foamed gelatin layer. The foam was lyophilized until dryness at 0.01 mbar pressure and a temperature ramp from 0° C. to 20° C.

Lyophilized enzyme powder was equally dispersed on the dry gelatin patch and incorporated into the gelatin matrix by using a needle roller (Derma Microneedle therapy needle roller, 3.0 mm 3-row, DR30-3R).

A polypropylene mesh (Gynecare, Gynemesh*PS, Ethicon) size 8×8 cm was placed on top and overlaid with gelatin foam prepared as described above. The patch assembly was lyophilized until dryness at 0.01 mbar pressure and a temperature ramp from 0° C. to 20° C.

Example 8

Gelatin and Glycerol Patch with Hernia Reinforcement Mesh, Enzyme Embedded into the Mesh Itself A 9% (w/V) gelatin (Gelita, lot #601089) with 3% (w/V) glycerol (Frutarom, lot#26319005) in 0.01M Na—Ac (Sodium acetate trihydrate, Merck lot#A902812 014) solution was heated to 38° C. The solution was foamed using the batched foaming process. A 5 mm layer of foam was poured into the lyophilization trays. Purified enzyme 750 u/ml (lot #27-37) was mixed with 2.5% (w/V) HPMC (ShinEtsu 8025107) in ratio 1:2. The polypropylene mesh (Gynecare, Gynemesh*PS, Ethicon) was dipped into the HPMC/enzyme solution, removed and immediately placed on top of the gelatin foam. An additional of gelatin foam layer was equally dispersed on top of the polypropylene The patch assembly was lyophilized until dryness at 0.01 mbar pressure and a temperature ramp from 0° C. to 20° C.

Figure 6:
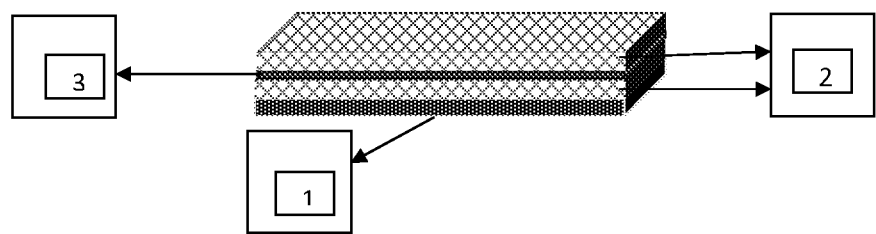
FIG. 6 shows an exemplary bandage as constructed for example #8.

Reference is now made to FIG. 6, which shows an exemplary bandage as constructed according to this Example, in accordance with some demonstrative embodiments. According to some embodiments, the bandage of FIG. 6 may include a non-foamed gelatin and glycerol backing 1; a foamed gelatin and glycerol 2, and a hernia mesh with HPMC and enzyme 3.

Example 9

Gelatin Patch with Gelatin Backing, Hernia Reinforcement Mesh and Foamed Gelatin, Spray Coated with Enzyme An 8% (w/V) gelatin (Gelita, lot #601089) in 0.01M Na—Ac (Sodium acetate trihydrate, Merck lot#A902812 014) solution was heated to 38° C. The solution was foamed using the mechanical mixer for 2 minutes at speed #2 and additional 1.5 minutes at speed #5. The foam was poured into the lyophilization trays and covered with a polypropylene mesh (Gynecare, Gynemesh*PS, Ethicon). The patch assembly was dried by lyophilization until dryness at 0.01 mbar pressure and a temperature ramp from 0° C. to 20° C.

A dialyzed enzyme solution was mixed with MB solution in ratio of 50:1 (enzyme:MB). Ethanol (Frutarom, lot#9306482 No. 015) was added to the solution in ratio of 2:3 (ethanol:enzyme solution).

The dry gelatin/polypropylene patches were sprayed with the enzyme/ethanol mixture and dried at 0.01 mbar and a temperature ramp from 0° C. to 20° C.

Example 10

Gelatin and PEG Patch with Integrated Powder Enzyme and a Heat Cross-Linked Backing A 9% (w/V) gelatin (Gelita, lot #601089) with 3% (w/V) PEG 400 (Sigma, lot#036K0046) in 0.01M Na—Ac (Sodium acetate trihydrate, Merck lot#A902812 014) solution was foamed using the batched foaming process. A 4 mm thin layer of the gelatin foam was poured into the lyophilization trays. The foam was lyophilized. The dried patches were cross-linked by heat in a vacuum oven (Nuve, EV 108, Mfg SN 03-0250) at 160° C. oven set temperature for 7 hours in vacuum of approximately 2 mbar (Ilmvac, 40017, Mfg SN 4ek6f56cx).

The cross-linked patches were equally wetted with water and placed in the lyophilization trays. The gelatin/PEG mixture was foamed in the batched foaming process and poured on top of the cross-linked patches. The patch assembly was lyophilized until dryness.

Lyophilized enzyme powder was equally dispersed on the patch and incorporated into the gelatin foam matrix using a needle roller (Derma Microneedle therapy needle roller, 3.0 mm 3-row, DR30-3R).

The patch was sprayed with water and ethanol (Frutarom, lot#9306482 No. 015) mixture in ratio of 1:9.

The patch assembly was dried at 0.01 mbar and a temperature ramp from 0° C. to 20° C.

Example 11

Burst Pressure Testing of Heat Dried Foamed Gelatin Layer with Embedded Enzyme

An enzyme solution was prepared by mixing 95% ethanol with purified water, blue color powder (Univar Limited, 37005 FD&C Blue No. 1) and purified enzyme solution (550 u/ml) to a final concentration of 80% ethanol, 30 mg/L of blue color powder and enzyme final activity of 41 u/ml.

Heat dried foamed gelatin layer of size 90×90×10 mm3 was placed in a tray and covered with 4 ml of the ethanol based enzyme solution using a syringe pump (Kd Scientific, Mfg S/N RS 232) with rate setting of 15 ml/min and syringe diameter of 26 mm. The tray with the foamed gelatin was moved under the syringe nozzle to achieve homogeneous cover.

The foamed gelatin was dried by lyophilization at 0.01 mbar pressure and a temperature ramp from 0° C. to 20° C.

Figure 10:
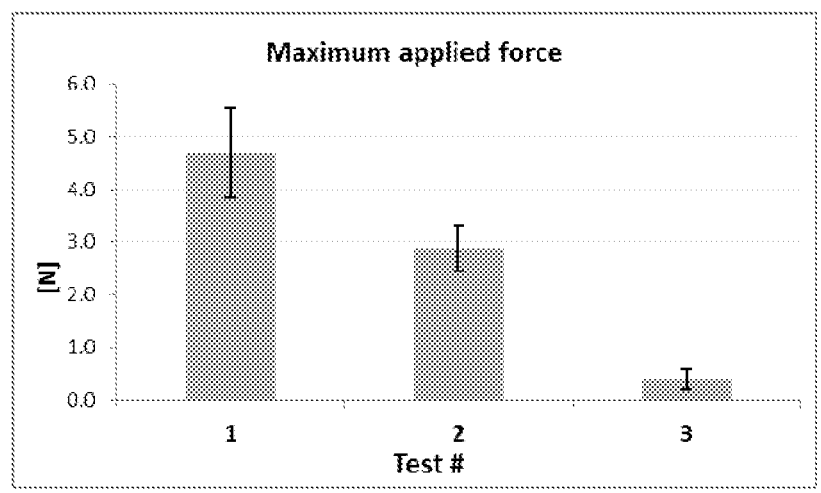
FIG. 10 is an illustrative graph demonstrating the results presented in Table #8.
Figure 11:
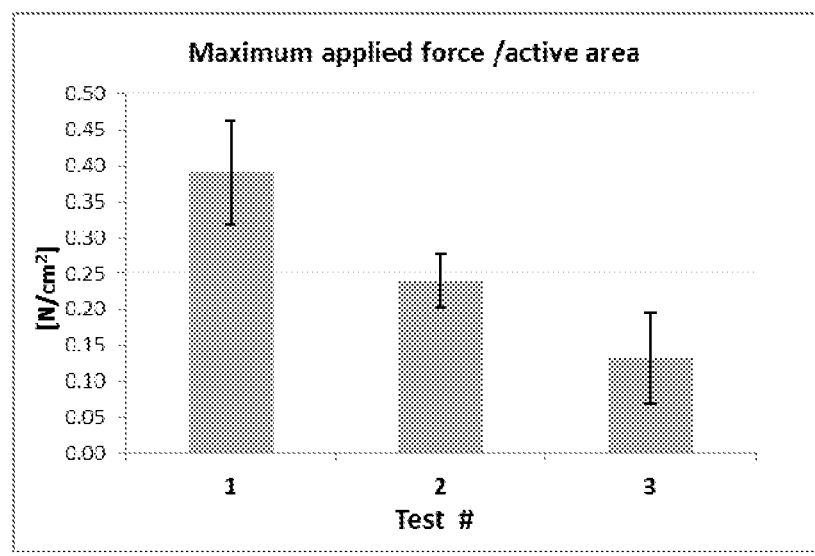
FIG. 11 is an illustrative graph demonstrating the results presented in Table #8.

Burst pressure results are shown in Table 7 for this Example and for subsequent Examples; please also see FIGS. 10-12 as appropriate.

Example 12

Gelatin "Sandwich" Patch with Integrated Powder Enzyme and Sprayed Enzyme with Heat Cross-Linked Gelatin Backing An 11% (w/v) gelatin (Gelita) solution in 0.01M Na—Ac (Sodium acetate trihydrate, Merck) solution was heated to 38° C. The gelatin solution was foamed using the batched foaming process. An approximately 3 mm layer of the foamed gelatin was poured into the trays. The foam was lyophilized until dryness at 0.01 mbar pressure and a temperature ramp from 0° C. to 20° C. The dry patches were cross-linked by heat in vacuum oven (Nuve, EV 108, Mfg SN 03-0250) at 160° C. oven set temperature for 7 hours in vacuum of ~2 mbar (Ilmvac, MPC 201 TMfg SN 4ek6f56cx).

9% (w/v) gelatin (Gelita) in 0.1M Na—Ac (Sodium acetate trihydrate, Merck) solution was heated to 38° C. The gelatin solution was foamed using the batched foaming process. The previously cross-linked gelatin pad was covered with an approximately 3 mm layer of the foamed gelatin and lyophilized using same conditions as described above. Lyophilized enzyme powder was equally dispersed on the dry gelatin patch and incorporated into the gelatin matrix by using a needle roller (Derma Microneedle therapy needle roller, 3.0 mm 3-row, DR30-3R).

The patch with the embedded enzyme powder was overlaid with 9% (w/v) gelatin foam prepared as described above. The patch assembly was lyophilized until dryness at 0.01 mbar pressure and a temperature ramp from 0° C. to 20° C. An enzyme solution was prepared by mixing purified enzyme (300 u/ml) with ethanol (Frutarom), in ratio of 3:2. A MB solution was added to the mixture in ratio of 3:50 (MB: enzyme solution).

The enzyme solution was sprayed equally onto the lyophilized pads. The sprayed patched were dried by lyophilization at 0.01 mbar pressure and a temperature ramp from 0° C. to 20° C.

Example 13

Burst Pressure Testing of Gelatin Patch with 2 Steps of Enzyme Integration and Heat Cross-Linked Double Layered Gelatin Backing 10 ml of 11% (w/V) gelatin (Gelita) in 0.01M Na—Ac (Sodium acetate trihydrate, Merck) solution was poured into lyophilization trays (10×10 cm). The trays were kept in RT for about 30 minutes until the stabilization of the solution.

Solution of 11% gelatin (Gelita) in 0.01M Na—Ac (Sodium acetate trihydrate, Merck) was prepared and heated to 38° C. The solution was foamed using the batched foaming.

The foam was loaded into the trays, covering the non-foamed gelatin layer, total thickness of 5 mm. The patch was lyophilized until dryness at 0.01 mbar pressure and a temperature ramp from 0° C. to 20° C. The dry patches were cross-linked by heat in vacuum oven (Nuve, EV 108, Mfg SN 03-0250) at 160° C. oven set temperature for 7 hours in vacuum of ~2 mbar (Ilmvac, MPC 201 TMfg SN 4ek6f56cx).

The cross-linked pads were soaked for 19 hours in 0.07% (V/V) tween20 (Merck) in water solution. The solution residues were removed from the trays. 9% (w/V) gelatin (Gelita) solution in 0.01M Na—Ac (Sodium acetate trihydrate, Merck) was heated to 38° C. The gelatin solution was foamed using the batched foaming process and poured on top of the soaked, cross-linked pads. The patch was lyophilized until dryness at 0.01 mbar pressure and a temperature ramp from 0° C. to 20° C.

An enzyme solution was prepared by mixing purified enzyme (750 u/ml), ethanol (Frutarom) and acetonitrile (Sigma) in ratio of 1:4:5. 15 ml of the solution were dripped on top of the dry pads. The patches were dried using the lyophilizer at 0.01 mbar pressure and a temperature ramp from 0° C. to 20° C.

Another enzyme solution was prepared by mixing purified enzyme (300 u/ml) with ethanol (Frutarom), in ratio of 3:2. A MB solution was added to the mixture in ratio of 3:50 (MB: enzyme solution).

The enzyme solution was sprayed equally onto the lyophilized pads. The sprayed patched were dried by lyophilization at 0.01 mbar pressure and a temperature ramp from 0° C. to 20° C.

Example 14

Burst Pressure Testing of Gelatin Patch with Integrated Enzyme Powder Sealed with Sprayed Enzyme and Chemically Cross-Linked Double Layered Gelatin Backing A 9% (w/V) gelatin (Gelita) in 0.01M Na—Ac (Sodium acetate trihydrate, Merck) was heated to 38° C. and foamed using the batched foaming process. A thin layer of the foam was loaded into the trays (about 4 mm thickness). The foam was lyophilized until dryness. Subsequently, the gelatin pads were cross-linked chemically.

The cross-linking solution consists of 70% ethanol (Frutarom) and 0.05% (w/V) DL-glyceraldehyde (Biosynth chemistry and biology) in purified water. Each pad was placed in a container, covered with a sufficient amount of cross-linking solution and sealed. The containers were placed in the incubator for 72 hours at 37° C.

Subsequently, the pads were washed with purified water, extensively.

A 9% gelatin (Gelita) in 0.01M Na—Ac (Sodium acetate trihydrate, Merck) solution was prepared and foamed under the same conditions as the cross-linked patch. The cross linked pads were placed in the lyophilization trays and covered with the prepared foam. The pads were lyophilized until dryness at 0.01 mbar pressure and a temperature ramp from 0° C. to 20° C.

Lyophilized enzyme powder was equally dispersed on the patch and incorporated into the gelatin foam matrix using a needle roller (Derma Microneedle therapy needle roller, 3.0 mm 3-row, DR30-3R).

Another enzyme solution was prepared by mixing purified enzyme (300 u/ml) with ethanol (Frutarom), in ratio of 3:2. A MB solution was added to the mixture in ratio of 3:50 (MB: enzyme solution).

The enzyme solution was sprayed equally onto the lyophilized pads. The sprayed patched were dried by lyophilization at 0.01 mbar pressure and a temperature ramp from 0° C. to 20° C.

Example 15

Burst Pressure Testing of Particulated Gelatin Pad Soaked with Enzyme, for Cavity Shaped Wounds A 9% gelatin (Gelita) in 0.01M Na—Ac (Sodium acetate trihydrate, Merck) was prepared and heated to 38° C. The solution was foamed using the batched foaming. The foam was loaded into the trays and lyophilized until dryness at 0.01 mbar pressure and a temperature ramp from 0° C. to 20° C.

The dry pads were cut to pieces of size 8×10×10 mm$^3$.

An enzyme solution was prepared by mixing 95% ethanol with purified water, blue color powder (Univar Limited, 37005 FD&C Blue No. 1) and purified enzyme solution (550 u/ml) to a final concentration of 70% ethanol, 15 mg/L of blue color powder and enzyme final activity of 87 u/ml.

The particulate gelatin was soaked in the ethanol based enzyme solution in ratio of 15 ml solution per 1 g of gelatin particles. The gelatin was dried by lyophilization at 0.01 mbar pressure and a temperature ramp from 0° C. to 20° C.

Example 16

Burst Pressure Testing of Gelatin Patch with Heat Cross Linked Reinforcement and Embedded Enzyme Heat cross-linked gelatin sponges with 1 mm thickness were lightly wetted and placed in lyophilization trays.

Solution of 9% gelatin (Gelita) in purified water was prepared and heated to 38° C. The solution was foamed using the batched foaming. The foam was loaded into the trays, covering the 1 mm gelatin sponges. The patch was lyophilized until dryness at 0.01 mbar pressure and a temperature ramp from 0° C. to 20° C.

An enzyme solution was prepared by mixing 95% ethanol with purified water, blue color powder (Univar Limited, 37005 FD&C Blue No. 1) and purified enzyme solution (550 u/ml) to a final concentration of 80% ethanol, 30 mg/L of blue color powder and enzyme final activity of 41 u/ml.

The dry gelatin patches were covered with 10 ml of the ethanol based enzyme solution using a syringe pump (Kd Scientific, Mfg S/N RS 232) with rate setting of 15 ml/min and syringe diameter of 26 mm. Each tray was moved under the syringe nozzle to achieve homogeneous cover.

The foamed gelatin was dried by lyophilization at 0.01 mbar pressure and a temperature ramp from 0° C. to 20° C.

Example 17

Burst Pressure Testing of Gelatin Patch with Enzymatic Cross-Linked Gelatin Reinforcement and Embedded Enzyme Purified enzyme solution (550 u/ml) was diluted to 50 u/ml in 0.1M Na—Ac (Sodium acetate trihydrate). The gelatin solution and enzyme solution were mixed together and 30 ml of the mixture were poured into the lyophilization trays.

Solution of 9% gelatin (Gelita) in purified water was prepared and heated to 38° C. During the mixing of the enzyme with the gelatin solution, the 9% gelatin solution was foamed using the batched foaming. The foam was loaded into the trays, covering the 30 ml of the gelatin and enzyme mixture, prior to complete curing of the gelatin. The patch was lyophilized until dryness at 0.01 mbar pressure and a temperature ramp from 0° C. to 20° C.

An enzyme solution was prepared by mixing 99.98% ethanol, with purified water, blue color powder (Univar Limited, 37005 FD&C Blue No. 1) and purified enzyme solution (550 u/ml) to a final concentration of 80% ethanol, 30 mg/L of blue color powder and enzyme final activity of 41 u/ml.

The dry gelatin patches were covered with 10 ml of the ethanol based enzyme solution using a syringe pump (Kd Scientific, Mfg S/N RS 232) with rate setting of 15 ml/min and syringe diameter of 26 mm. Each tray was moved under the syringe nozzle to achieve homogeneous cover.

The foamed gelatin was dried by lyophilization at 0.01 mbar pressure and a temperature ramp from 0° C. to 20° C.

Example 18

Burst Pressure Testing of Gelatin Patch with Non-Absorbable (Polyurethane) Reinforcement and Embedded Enzyme Polyurethane sheets of 1 mm thickness (DermaMed) were placed in lyophilization trays.

Solution of 9% gelatin (Gelita) in purified water was prepared and heated to 38° C. The solution was foamed using the batched foaming process. The foam was loaded into the trays, covering the 1 mm gelatin sponges. The patch was lyophilized until dryness at 0.01 mbar pressure and a temperature ramp from 0° C. to 20° C.

An enzyme solution was prepared by mixing 99.98% ethanol with purified water, blue color powder (Univar Limited, 37005 FD&C Blue No. 1) and purified enzyme solution (550 u/ml) to a final concentration of 80% ethanol, 30 mg/L of blue color powder and enzyme final activity of 41 u/ml.

The dry gelatin patches were covered with 10 ml of the ethanol based enzyme solution using a syringe pump (Kd Scientific, Mfg S/N RS 232) with rate setting of 15 ml/min and syringe diameter of 26 mm. Each tray was moved under the syringe nozzle to achieve homogeneous cover.

The foamed gelatin was dried by lyophilization at 0.01 mbar pressure and a temperature ramp from 0° C. to 20° C.

Example 19

In-Vivo Test of Hernia Mesh Adhesion to Abdominal Wall

3 Kinds of Hernia Mesh Incorporated Patches were Prepared According to Following Description Type 1:
An 8% (w/V) gelatin (Gelita) in 0.01M Na—Ac (Sodium acetate trihydrate) solution was heated to 38° C. The solution was foamed using the batches method. 60 ml of the foam was poured into the lyophilization trays and covered with a polypropylene mesh (Gynecare, Gynemesh*PS, Ethicon). The mesh was covered with another layer of foamed gelatin. The patch assembly was dried by lyophilization until dryness at 0.01 mbar pressure and a temperature ramp from 0° C. to 20° C.

Type 2:
An 8% (w/V) gelatin (Gelita) and 3% (V/V) glycerol (Frutarom) in 0.01M Na—Ac (Sodium acetate trihydrate) solution was heated to 38° C. 10 ml of the solution were poured into the lyophilization trays and kept for about 25 min at 10° C. for stabilization. A polypropylene mesh (Gynecare, Gynemesh*PS, Ethicon) was placed on top of the gelatin and glycerol layer. 8% (w/V) gelatin (Gelita) in 0.01M Na—Ac (Sodium acetate trihydrate, Merck) solution was heated to 38° C.

The solution was foamed using the batches method. The foam was poured into the trays on top of the hernia mesh. The patch assembly was dried by lyophilization until dryness at 0.01 mbar pressure and a temperature ramp from 0° C. to 20° C.

Type 3:
An 8% (w/V) gelatin (Gelita) and 3% (V/V) glycerol (Frutarom) in 0.01M Na—Ac (Sodium acetate trihydrate, Merck) solution was heated to 38° C. 10 ml of the solution were poured into the lyophilization trays and kept for about 25 min at 10° C. for stabilization. 8% (w/V) gelatin (Gelita) in 0.01M Na—Ac (Sodium acetate trihydrate, Merck) solution was heated to 38° C. The solution was foamed using the batches method. 60 ml of the foam was poured into the lyophilization trays and covered with a polypropylene mesh (Gynecare, Gynemesh*PS, Ethicon). The mesh was covered with another layer of foamed solution. The patch assembly was dried by lyophilization until dryness at 0.01 mbar pressure and a temperature ramp from 0° C. to 20° C.

A dialyzed enzyme solution was mixed with MB solution in ratio of 50:1 (enzyme:MB). Ethanol (Frutarom) was added to the solution in ratio of 2:3 (ethanol: enzyme solution).

All three compositions of dry gelatin/polypropylene patches were sprayed with the enzyme/ethanol mixture and dried at 0.01 mbar and a temperature ramp from 0° C. to 20° C.

The patches were tested in-vivo. The three types of patches were applied on swine abdominal wall, in open surgery. The patches were covered with small amount of saline and the abdominal wall was covered back with the fat tissue. Pressure was applied on the patches for 4 minutes. After pressure removing, the adhesion of the hernia mesh to both abdominal wall and the fat tissue was tested.

TABLE 5

|  | Adhesion to abdominal wall | Adhesion to fat tissue |
| --- | --- | --- |
| Type 1 | Good adhesion. Force was applied to peel the mesh of the tissue | Little adhesion |
| Type 2 | Medium adhesion to the tissue | Little adhesion |
| Type 3 | Poor adhesion to the tissue | Very little adhesion |

Example 20

Burst Pressure Testing of Gelatin Patch with 2 Steps of Enzyme Integration and Heat Cross-Linked Gelatin Backing Solution of 20% gelatin (Gelita) in 0.01M Na—Ac (Sodium acetate trihydrate, Merck) was prepared and heated to 38° C. The solution was foamed using the batched foaming. The foam was loaded into the trays, creating a 3 mm thickness layer. The patch was lyophilized until dryness at 0.01 mbar pressure and a temperature ramp from 0° C. to 20° C. The dry patches were cross-linked by heat in vacuum oven (Nuve, EV 108, Mfg SN 03-0250) at 160° C. oven set temperature for 7 hours in vacuum of ~2 mbar (Ilmvac, MPC 201 TMfg SN 4ek6f56cx).

The cross-linked pads were soaked for 19 hours in 0.07% (V/V) tween20 (Merck) in water solution. The solution residues were removed from the trays. 9% (w/V) gelatin (Gelita) in 0.01M Na—Ac (Sodium acetate trihydrate, Merck) solution was heated to 38° C. The gelatin solution was foamed using the batched foaming process and poured on top of the soaked, cross-linked pads. The patch was lyophilized until dryness at 0.01 mbar pressure and a temperature ramp from 0° C. to 20° C.

An enzyme solution was prepared by mixing purified enzyme (750 u/ml), ethanol (Frutarom) and acetonitrile (Sigma) in ratio of 1:4:5. 15 ml of the solution were dripped on top of the dry pads. The patches were dried using the lyophilizer at 0.01 mbar pressure and a temperature ramp from 0° C. to 20° C.

Another enzyme solution was prepared by mixing purified enzyme (300 u/ml) with ethanol (Frutarom), in ratio of 3:2. A MB solution was added to the mixture in ratio of 3:50 (MB: enzyme solution).

The enzyme solution was sprayed equally onto the lyophilized pads. The sprayed patched were dried by lyophilization at 0.01 mbar pressure and a temperature ramp from 0° C. to 20° C.

Example 20

Ebeam Sterilization of Patches

Different patches were sterilized using E-beam radiation.

Three doses of radiation were tested-25kGy, 30kGy, 35kGy. Materials that were prepared according to example #20 were radiated at 35kGy and tested afterwards. The materials were tested using the advanced burst pressure test before radiation, immediately after radiation and once a month afterwards.

TABLE 6

| Time point | # of repetitions | Burst pressure result |
|---|---|---|
| Control (wasn't radiated) | 5 | 204 ± 83 mmHg |
| t = 0 (immediately after radiation) | 6 | 230 ± 103 mmHg |
| t = 1 month | 6 | 276 ± 108 mmHg |
| t = 2 months | 5 | 201 ± 97 mmHg |
| t = 3 months | 5 | 220 ± 54 mmHg |

Example 21

Gelatin Patch with Enzyme Integrated into Carrier (HPMC) that is Layered or Embedded into Gelatin Matrix Solution of 9% gelatin (Gelita) in purified water was prepared and heated to 38° C. The solution was foamed using the batched foaming. The foam was loaded into the lyophilization trays. Purified enzyme (550 u/ml) was diluted to 40 u/ml in a 1.5% HPMC solution. Color was added to the enzyme solution-14 mg/L solution of blue color powder (Univar Limited, 37005 FD&C Blue No. 1). 15 ml of the enzyme solution were spread on the foamed gelatin surface. The patch was lyophilized until dryness at 0.01 mbar pressure and a temperature ramp from 0° C. to 20° C.

TABLE 7

| Example # | Test model | # of repetitions | Result |
|---|---|---|---|
| 1 | Basic burst pressure | 5 | 187 ± 11 mmHg |
| 2 | Advanced burst pressure test | 8 | 180 ± 44 mmHg |
| 3 | Advanced burst pressure test | 8 | 278 ± 80 mmHg |
| 4 | Advanced burst pressure test | 7 | 291 ± 59 mmHg |

TABLE 7-continued

| Example # | Test model | # of repetitions | Result |
|---|---|---|---|
| 5 | Advanced burst pressure test | 10 | 350 ± 38 mmHg |
| 6 | Advanced burst pressure test | 6 | 214 ± 36 mmHg |
| 11 | Advanced burst pressure test | 4 | 211 ± 12 mmHg |
| 13 | Advanced burst pressure test | 7 | 214 ± 80 mmHg |
| 14 | Advanced burst pressure test | 6 | 189 ± 60 mmHg |
| 15 | Advanced burst pressure test | 5 | 192 ± 86 mmHg |
| 16 | Advanced burst pressure test | 3 | 238 ± 88 mmHg |
| 17 | Advanced burst pressure test | 4 | 220 ± 34 mmHg |
| 18 | Advanced burst pressure test | 4 | 190 ± 92 mmHg |

Example 22

In-Vitro Test of Hernia Mesh Adhesion to Abdominal Wall

Figure 8:
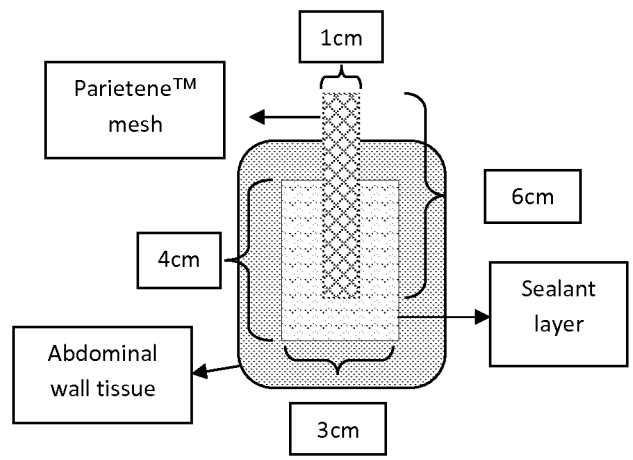
FIG. 8 demonstrates a parietene mesh, as used in example #22, in accordance with some demonstrative embodiments.
Figure 9:
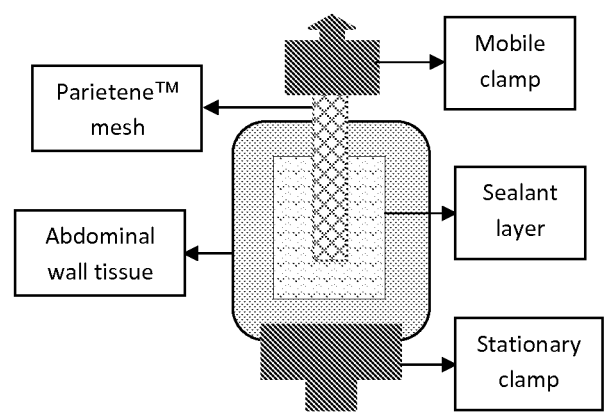
FIG. 9 demonstrates a parietene mesh attached to a mobile clamp, as used in example #22, in accordance with some demonstrative embodiments.

Used Materials and Tools:
Parietene™ (Covidien)—Polypropylene mesh cut into stripes the size of 1×6 cm$^2$
Parietene™ ProGrip™ (Covidien)—Polypropylene and polylactic acid mesh cut into stripes the size of 1×6 cm$^2$
Sealant Components:
  25% (w/V) gelatin (Gelita) solution
  Microbial transglutaminase PEGylated solution (60 u/ml)
Three way stopcocks ("SURUWAY")
3 ml luer lock syringes ("Medi-Plus")
Rat abdominal wall, kept at −20° C. after harvesting the tissue. Prior to use the tissue was defrosted and kept at 37° C.
Material Preparation:
The gelatin solution was filled in the syringes—2 ml in each syringe
The enzyme solution was filled in the syringes—1 ml in each syringe
The syringes were kept in a circulating bath at 25° C. for temperature stabilization prior to use.
Each set of materials (gelatin syringe and enzyme syringe) was connected to the three way stopcock and mixed syringe to syringe 9 times, immediately before application.
Test Method:
3 tests were done to test the adhesive abilities of the meshes.
Test 1:
The Parietene mesh was covered with sealant in an area of 4×3 cm$^2$, as demonstrated in FIG. 8. Sealant amount used for this test is 0.2 ml/cm$^2$. 7 minutes after application the tissue was placed in the tensile testing machine (Instron Tensile Testing System, model 3343). The tissue set in a stationary clamp and the mesh is attached to a mobile clamp (As shown in FIG. 9). The mobile clamp was moved up at a steady rate of 100 mm/min.
Test 2:
The Parietene mesh was covered with sealant in an area of 4×3 cm$^2$, as demonstrated in FIG. 8. Sealant amount used for this test is 0.2 ml/cm$^2$. Immediately after application a silicone sheet with total weight of 65 g was placed on top of the sealant layer. 7 minutes after application the tissue was placed in the tensile testing machine Instron Tensile Testing System, model 3343), the tissue is stationary, and the mesh is attached to a mobile clamp (as shown in FIG. 9). The mobile clamp was moved up at a steady rate of 100 mm/min.
Test 3:
The Parietene ProGrip mesh and the abdominal wall tissue were wet with saline and then manually attached for optimal adherence. After application the tissue was placed in the tensile testing machine, the tissue is stationary, and the mesh is attached to a mobile clamp. The mobile clamp was moved up at a steady rate of 100 mm/min.

TABLE 8

Test results:

| Test # | Repetitions # | Maximum applied force [N] | Maximum applied force/Active area [N/cm$^2$] |
|---|---|---|---|
| 1 | 8 | 4.69 ± 0.86 | 0.39 ± 0.07 |
| 2 | 5 | 2.88 ± 0.44 | 0.24 ± 0.04 |
| 3 | 10 | 0.4 ± 0.19 | 0.13 ± 0.06 |

FIGS. 10 and 11 show the test results graphically.

Example 23

Pattern-Etched Silicone Backing with Dried Foamed Gelatin Matrix

Figure 13:
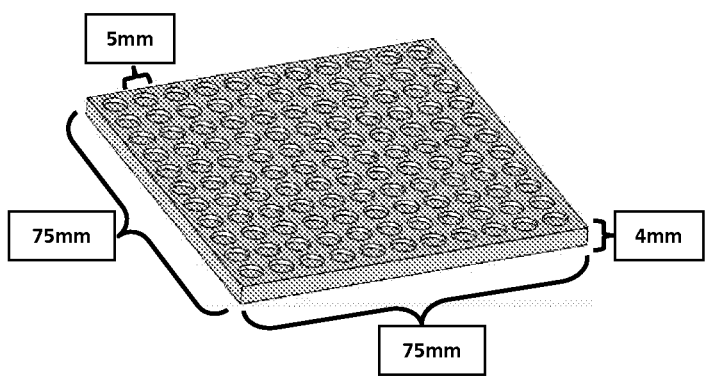
FIG. 13 shows a pattern etched into a silicone sheet.

A pattern was etched into a silicone sheet of 4 mm thickness and 20 shore using a laser (Universal Laser Systems. PLS6.150D; shore is a unit of measurement for hardness of rubber). Round holes of 1 mm depth and 5 mm diameter with 1.6 mm distance from each other were engraved (shown in FIG. 13). The engraved silicone sheets were placed in lyophilization trays. Solution of 9% gelatin (Gelita) in purified water was prepared and heated to 38° C. The solution was foamed using the batched foaming. The foam was loaded into the trays, on top of engraved silicone sheet size of 75 mm×75 mm. The patch was lyophilized. After lyophilization, the gelatin matrix was very well attached to the silicone backing. The gelatin matrix and silicone backing could be bent together without dehiscence and considerable manual force had to be exerted in order to separate the gelatin matrix from the silicone backing.

When experiment was repeated with identical silicone sheet without pattern, the silicone sheet did not adhere well to the gelatin matrix. Upon mild handling, the silicone sheet and gelatin matrix fell apart.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shah not be construed as an admission that such reference is available as prior art to the present invention.

What is claimed is:

1. A patch comprising an implantable surgical mesh, a cross-linkable protein matrix and a protein cross-linking enzyme in contact with said matrix for cross-linking said cross-linkable protein, wherein said matrix is incorporated into, layered on or surrounding said mesh, with the proviso that said enzyme is not thrombin, wherein said cross-linkable protein comprises gelatin, wherein said gelatin is present in a protein matrix and wherein said matrix has a density in a range of from 5 to 100 mg/cm$^3$, wherein said cross-linkable protein matrix comprises porous gelatin foam.

2. The patch of claim 1, wherein said enzyme is present at a depth of at least 0.5 mm in said protein layer, wherein said enzyme is a non-blood derived enzyme.

3. The patch of claim 1, wherein said enzyme is incorporated either homogeneously throughout the matrix or present in the matrix at a depth of at least one of 0.5 mm, 1 mm or up to 20 mm from the matrix surface.

4. The patch of claim 1, wherein said gelatin foam comprises dried or lyophilized foamed gelatin solution.

5. The patch of claim 1, further comprising a reinforcing backing layer, wherein said surgical mesh is located at one or more of between the reinforcement layer and the gelatin matrix; in the middle of the gelatin matrix; or on top of the gelatin matrix; or a combination thereof.

6. The patch of claim 5, wherein said enzyme is present in an enzymatic layer and wherein said gelatin is positioned in one or more of the following locations: within said patch, on said enzymatic layer, in said enzymatic layer, on said reinforcing back layer, in said reinforcing back layer, or between said an enzymatic layer and said reinforcing back layer.

7. The patch of claim 1, wherein said gelatin has a density in a range of from 10 to 50 mg/cm$^3$.

8. The patch of claim 1, wherein said enzyme comprises transglutaminase (TG), and wherein the gelatin is incorporated into a gelatin matrix with said transglutaminase such that one or more of the following occur: a majority of enzyme activity is preserved throughout a process of preparation; enzyme is equally distributed across the gelatin matrix surface; and/or enzyme is embedded into the depth of the gelatin matrix (gradient or equal distribution).

9. The patch of claim 8, wherein said transglutaminase is incorporated into said gelatin matrix according to one or more of mixing before drying said matrix or after drying said matrix, optionally wherein said matrix is dried to comprise no more than 10% moisture content.

10. The patch of claim 8, wherein transglutaminase is present at a concentration of from 0.05 to 2 mg transglutaminase/cm$^3$ gelatin matrix.

11. The patch of claim 1, wherein the gelatin includes a plurality of moieties, and wherein more than 50% of said moieties are non-cross linked.

12. The patch according to claim 1, wherein said patch can close a tissue wound having burst pressure of at least 200 mmHg.

13. The patch of claim 1 adapted for surgical mesh fixation where mesh can be adhered to an organ surface, tissue surface, or cavity.

14. The patch of claim 13, wherein said mesh comprises any of a synthetic mesh, a biological mesh, or a combination synthetic-biological mesh.

15. The patch of claim 1, wherein said transglutaminase comprises a microbial transglutaminase.

16. The patch of claim 1, wherein the patch comprises a plurality of gelatin layers and wherein optionally each of said gelatin layers has a different percentage concentration of gelatin.

17. The patch of claim 1, wherein said cross-linkable protein is provided as a protein matrix, further comprising a reinforcing back layer, wherein said reinforcing back layer is mechanically modified so as to increase surface area of protein matrix interface with back layer, and wherein said mechanical modification comprises one or more of being etched, carved, cut, engraved, or textured.

18. The patch of claim 1, wherein the enzyme is encapsulated prior to incorporation in the patch, and wherein the enzyme is encapsulated in a material selected from the group consisting of: PLA, PGA, PLGA, k-carrageenan, liposomes, gelatin, collagen, fibrinogen, albumin, polyethylene glycol, polyvinyl alcohol, cellulose ethers.

19. The patch of claim 1, wherein the enzyme is chemically modified prior to incorporation in the patch or pressing.

20. The patch of claim 1, wherein the patch is sterilized to a sterility assurance level of $10^{-6}$ through exposure to electron beam radiation, wherein the radiation dosage is in the range of 20-40 kGy.

21. The patch of claim 20, further incorporating a radioprotectant selected from the group consisting of Ascorbate, Benzyl alcohol, Benzyl benzoate, Butylated Hydroxyanisole (BHA), Chlorobutanol, Cysteine, Mannitol, Methyl paraben, Niacinamide, Phenol, Propylene glycol, Propyl gallate, Propyl paraben, Sodium bisulfate, Sodium metabisulfite, Sodium salicylate, Sodium thiosulfate, Tocopherol, Trehalose.

* * * * *